US009173669B2

(12) United States Patent
Mathis et al.

(10) Patent No.: US 9,173,669 B2
(45) Date of Patent: Nov. 3, 2015

(54) ENHANCED EFFICACY LUNG VOLUME REDUCTION DEVICES, METHODS, AND SYSTEMS

(75) Inventors: Mark L. Mathis, Fremont, CA (US); David Thompson, San Jose, CA (US); Patrick Wu, Pleasanton, CA (US)

(73) Assignee: PneumRx, Inc., Mountain View, CA (US)

( * ) Notice: Subject to any disclaimer, the term of this patent is extended or adjusted under 35 U.S.C. 154(b) by 330 days.

(21) Appl. No.: 12/558,206

(22) Filed: Sep. 11, 2009

(65) Prior Publication Data
US 2010/0070050 A1 Mar. 18, 2010

Related U.S. Application Data

(60) Provisional application No. 61/096,550, filed on Sep. 12, 2008, provisional application No. 61/096,559, filed on Sep. 12, 2008.

(51) Int. Cl.
*A61F 2/04* (2013.01)
*A61M 15/00* (2006.01)
(Continued)

(52) U.S. Cl.
CPC ............ *A61B 17/24* (2013.01); *A61B 17/12022* (2013.01); *A61B 17/12104* (2013.01); *A61B 17/12131* (2013.01); *A61B 17/12145* (2013.01); *A61B 17/12172* (2013.01); *A61B 19/00* (2013.01); *A61M 16/04* (2013.01); *A61M 16/0406* (2014.02); *A61B 17/1285* (2013.01);
(Continued)

(58) Field of Classification Search
CPC ................ A61B 17/12104; A61B 17/1285; A61B 17/24; A61B 2017/242; A61B 2017/00809; A61B 17/12022; A61B 17/12131; A61B 17/1245; A61B 17/12172; A61B 19/00; A61B 17/0406; A61M 16/0406; A61M 16/04
USPC ........ 623/23.64–23.65, 23.67–23.7; 606/151, 606/157; 128/898
See application file for complete search history.

(56) References Cited

U.S. PATENT DOCUMENTS 3,559,652 A 2/1971 Banitt et al.
4,013,080 A 3/1977 Froning
(Continued)

FOREIGN PATENT DOCUMENTS

CN 1753703 A 3/2006
FR 2840796 12/2003
(Continued)

OTHER PUBLICATIONS

O'Brien et al. "Improvements in Lung Function, Exercise, and Quality of Life in Hypercapnic COPD Patients After Lung Volume Reduction Surgery". Chest 115(1999): 75-84.*
(Continued)

*Primary Examiner* — Andrew Iwamaye
(74) *Attorney, Agent, or Firm* — Kilpatrick Townsend and Stockton LLP

(57) ABSTRACT

A lung volume reduction system is disclosed comprising an implantable device adapted to be delivered to a lung airway of a patient in a delivery configuration and to change to a deployed configuration to bend the lung airway. The invention also discloses a method of bending a lung airway of a patient comprising inserting a device into the airway in a delivery configuration and bending the device into a deployed configuration, thereby bending the airway.

18 Claims, 50 Drawing Sheets

(51) Int. Cl.

| | | |
|---|---|---|
| *A61M 16/00* | (2006.01) | |
| *A62B 7/00* | (2006.01) | |
| *A62B 9/00* | (2006.01) | |
| *A62B 18/00* | (2006.01) | |
| *A61B 5/08* | (2006.01) | |
| *A61B 17/24* | (2006.01) | |
| *A61B 17/12* | (2006.01) | |
| *A61M 16/04* | (2006.01) | |
| *A61B 19/00* | (2006.01) | |
| *A61B 17/128* | (2006.01) | |
| *A61B 17/00* | (2006.01) | |

(52) U.S. Cl.
CPC ............ *A61B 2017/00477* (2013.01); *A61B 2017/00809* (2013.01); *A61B 2017/12054* (2013.01); *A61B 2019/461* (2013.01); *A61B 2019/5466* (2013.01); *A61M 2205/0266* (2013.01)

(56) References Cited

U.S. PATENT DOCUMENTS

| | | | |
|---|---|---|---|
| 4,153,058 A | 5/1979 | Nehme | |
| 4,233,984 A | 11/1980 | Walling | |
| 4,245,624 A | 1/1981 | Komiya | |
| 4,479,792 A | 10/1984 | Lazarus et al. | |
| 4,494,531 A | 1/1985 | Gianturco | |
| 4,532,935 A | 8/1985 | Wang | |
| 4,702,260 A | 10/1987 | Wang | |
| 4,739,760 A | 4/1988 | Chin et al. | |
| 4,766,906 A | 8/1988 | Wang | |
| 4,769,017 A | 9/1988 | Fath et al. | |
| 4,821,722 A | 4/1989 | Miller et al. | |
| 4,880,015 A | 11/1989 | Nierman | |
| 5,056,529 A | 10/1991 | de Groot | |
| 5,084,012 A | 1/1992 | Kelman | |
| 5,108,368 A | 4/1992 | Hammerslag et al. | |
| 5,165,420 A | 11/1992 | Strickland | |
| 5,186,167 A | 2/1993 | Kolobow | |
| 5,190,546 A | 3/1993 | Jervis | |
| 5,219,895 A | 6/1993 | Kelman | |
| 5,240,011 A | 8/1993 | Assa | |
| 5,261,889 A | 11/1993 | Laine et al. | |
| 5,303,714 A | 4/1994 | Abele et al. | |
| 5,312,329 A | 5/1994 | Beaty et al. | |
| 5,312,331 A | 5/1994 | Knoepfler | |
| 5,315,992 A | 5/1994 | Dalton | |
| 5,334,183 A | 8/1994 | Wuchinich | |
| 5,354,287 A | 10/1994 | Wacks | |
| 5,385,606 A | 1/1995 | Kowanko | |
| 5,423,830 A | 6/1995 | Schneebaum et al. | |
| 5,472,017 A | 12/1995 | Kovalcheck | |
| 5,479,938 A | 1/1996 | Weier | |
| 5,484,401 A | 1/1996 | Rodriguez et al. | |
| 5,514,536 A | 5/1996 | Taylor | |
| 5,522,819 A | 6/1996 | Graves et al. | |
| 5,526,821 A | 6/1996 | Jamshidi | |
| 5,549,551 A | 8/1996 | Peacock, III et al. | |
| 5,549,904 A | 8/1996 | Juergensen et al. | |
| 5,599,294 A | 2/1997 | Edwards et al. | |
| 5,660,175 A | 8/1997 | Dayal | |
| 5,660,185 A | 8/1997 | Shmulewitz et al. | |
| 5,697,365 A | 12/1997 | Pell | |
| 5,735,264 A | 4/1998 | Siczek et al. | |
| 5,736,132 A | 4/1998 | Juergensen et al. | |
| 5,750,657 A | 5/1998 | Edwardson et al. | |
| 5,762,070 A | 6/1998 | Nagamatsu | |
| 5,846,235 A | 12/1998 | Pasricha et al. | |
| 5,875,692 A | 3/1999 | Lin | |
| 5,895,417 A | 4/1999 | Pomeranz et al. | |
| 5,916,210 A | 6/1999 | Winston | |
| 5,916,212 A | 6/1999 | Baust et al. | |
| 5,938,635 A | 8/1999 | Kuhle | |
| 5,954,636 A | 9/1999 | Schwartz et al. | |
| 5,957,919 A | 9/1999 | Laufer | |
| 5,964,770 A | 10/1999 | Flomenblit et al. | |
| 5,972,026 A | 10/1999 | Laufer et al. | |
| 5,978,697 A | 11/1999 | Maytal et al. | |
| 6,066,090 A | 5/2000 | Yoon | |
| 6,080,113 A | 6/2000 | Heneveld et al. | |
| 6,083,255 A | 7/2000 | Laufer et al. | |
| 6,123,665 A | 9/2000 | Kawano | |
| 6,174,323 B1 | 1/2001 | Biggs et al. | |
| 6,183,498 B1 | 2/2001 | DeVore et al. | |
| 6,196,966 B1 | 3/2001 | Kerin et al. | |
| 6,200,333 B1 | 3/2001 | Laufer | |
| 6,245,090 B1 | 6/2001 | Gilson et al. | |
| 6,258,100 B1 | 7/2001 | Alferness et al. | |
| 6,267,732 B1 | 7/2001 | Heneveld et al. | |
| 6,273,907 B1 | 8/2001 | Laufer | |
| 6,283,988 B1 | 9/2001 | Laufer et al. | |
| 6,283,989 B1 | 9/2001 | Laufer et al. | |
| 6,287,290 B1 | 9/2001 | Perkins et al. | |
| 6,287,304 B1 | 9/2001 | Eggers et al. | |
| 6,293,951 B1 | 9/2001 | Alferness et al. | |
| 6,299,633 B1 | 10/2001 | Laufer | |
| 6,306,141 B1 | 10/2001 | Jervis | |
| 6,310,166 B1 | 10/2001 | Hickey et al. | |
| 6,312,428 B1 | 11/2001 | Eggers et al. | |
| 6,315,737 B1 | 11/2001 | Skinner | |
| 6,328,689 B1 | 12/2001 | Gonzalez et al. | |
| 6,328,701 B1 | 12/2001 | Terwilliger | |
| 6,352,503 B1 | 3/2002 | Matsui et al. | |
| 6,379,373 B1 | 4/2002 | Sawhney et al. | |
| 6,387,044 B1 | 5/2002 | Tachibana et al. | |
| 6,390,967 B1 | 5/2002 | Forman et al. | |
| 6,398,775 B1 | 6/2002 | Perkins et al. | |
| 6,402,701 B1 | 6/2002 | Kaplan et al. | |
| 6,402,754 B1 | 6/2002 | Gonzalez | |
| 6,402,781 B1 | 6/2002 | Langberg et al. | |
| 6,411,852 B1 | 6/2002 | Danek et al. | |
| 6,416,554 B1 | 7/2002 | Alferness et al. | |
| 6,443,944 B1 | 9/2002 | Doshi et al. | |
| 6,447,534 B2 | 9/2002 | Cragg et al. | |
| 6,464,648 B1 | 10/2002 | Nakamura | |
| 6,474,340 B1 | 11/2002 | Vaska et al. | |
| 6,478,730 B1 | 11/2002 | Bala et al. | |
| 6,485,407 B2 | 11/2002 | Alferness et al. | |
| 6,485,436 B1 | 11/2002 | Truckai et al. | |
| 6,488,673 B1 * | 12/2002 | Laufer et al. | 604/516 |
| 6,491,706 B1 | 12/2002 | Alferness et al. | |
| 6,494,844 B1 | 12/2002 | Van Bladel et al. | |
| 6,494,897 B2 | 12/2002 | Sterman et al. | |
| 6,509,031 B1 | 1/2003 | Miller et al. | |
| 6,514,290 B1 | 2/2003 | Loomas | |
| 6,514,522 B2 | 2/2003 | Domb | |
| 6,527,761 B1 * | 3/2003 | Soltesz et al. | 604/516 |
| 6,537,195 B2 | 3/2003 | Forman | |
| 6,537,314 B2 | 3/2003 | Langberg et al. | |
| 6,540,694 B1 | 4/2003 | Van Bladel et al. | |
| 6,540,716 B1 | 4/2003 | Holm | |
| 6,549,800 B1 | 4/2003 | Atalar et al. | |
| 6,551,255 B2 | 4/2003 | Van Bladel et al. | |
| 6,551,302 B1 | 4/2003 | Rosinko et al. | |
| 6,552,172 B2 | 4/2003 | Marx et al. | |
| 6,558,337 B2 | 5/2003 | Dvorak et al. | |
| 6,568,387 B2 | 5/2003 | Davenport et al. | |
| 6,569,166 B2 | 5/2003 | Gonzalez | |
| 6,577,893 B1 | 6/2003 | Besson et al. | |
| 6,585,639 B1 | 7/2003 | Kotmel et al. | |
| 6,589,161 B2 | 7/2003 | Corcoran | |
| 6,592,559 B1 | 7/2003 | Pakter et al. | |
| 6,592,594 B2 | 7/2003 | Rimbaugh et al. | |
| 6,599,311 B1 | 7/2003 | Biggs et al. | |
| 6,610,043 B1 | 8/2003 | Ingenito | |
| 6,622,731 B2 | 9/2003 | Daniel et al. | |
| 6,629,951 B2 | 10/2003 | Laufer et al. | |
| 6,632,222 B1 | 10/2003 | Edwards et al. | |
| 6,632,239 B2 | 10/2003 | Snyder et al. | |
| 6,632,243 B1 | 10/2003 | Zadno-Azizi et al. | |
| 6,634,363 B1 | 10/2003 | Danek et al. | |
| 6,638,275 B1 | 10/2003 | McGaffigan et al. | |
| 6,652,516 B1 | 11/2003 | Gough | |

(56) References Cited

U.S. PATENT DOCUMENTS

| | | |
|---|---|---|
| 6,652,520 B2 | 11/2003 | Moorman et al. |
| 6,653,525 B2 | 11/2003 | Ingenito et al. |
| 6,663,624 B2 | 12/2003 | Edwards et al. |
| 6,679,264 B1 | 1/2004 | Deem et al. |
| 6,682,520 B2 | 1/2004 | Ingenito |
| 6,685,626 B2 | 2/2004 | Wironen |
| 6,689,072 B2 | 2/2004 | Kaplan et al. |
| 6,690,976 B2 | 2/2004 | Fenn et al. |
| 6,692,494 B1 | 2/2004 | Cooper et al. |
| 6,694,977 B1 | 2/2004 | Federowicz et al. |
| 6,694,979 B2 | 2/2004 | Deem et al. |
| 6,695,791 B2 | 2/2004 | Gonzalez |
| 6,709,401 B2 | 3/2004 | Perkins et al. |
| 6,709,408 B2 | 3/2004 | Fisher |
| 6,709,456 B2 | 3/2004 | Langberg et al. |
| 6,712,812 B2 | 3/2004 | Roschak et al. |
| 6,716,180 B2 | 4/2004 | Fontenot |
| 6,723,095 B2 | 4/2004 | Hammerslag |
| 6,730,044 B2 | 5/2004 | Stephens et al. |
| 6,736,822 B2 | 5/2004 | McClellan et al. |
| 6,749,606 B2 | 6/2004 | Keast et al. |
| 6,752,767 B2 | 6/2004 | Turovskiy et al. |
| 6,752,812 B1 | 6/2004 | Truwit |
| 6,758,824 B1 | 7/2004 | Miller et al. |
| 6,768,425 B2 | 7/2004 | Flaherty et al. |
| 6,770,066 B1 | 8/2004 | Weaver et al. |
| 6,770,070 B1 | 8/2004 | Balbierz |
| 6,789,545 B2 | 9/2004 | Littrup et al. |
| 6,790,172 B2 | 9/2004 | Alferness et al. |
| 6,790,185 B1 | 9/2004 | Fisher et al. |
| 6,797,001 B2 | 9/2004 | Mathis et al. |
| 6,807,446 B2 | 10/2004 | Fenn et al. |
| 6,808,525 B2 | 10/2004 | Latterell et al. |
| 6,814,778 B1 | 11/2004 | Farnworth |
| 6,817,973 B2 | 11/2004 | Merril et al. |
| 6,825,091 B2 | 11/2004 | Bae et al. |
| 6,827,086 B2 | 12/2004 | Shuman |
| 6,827,683 B2 | 12/2004 | Otawara |
| 6,830,756 B2 | 12/2004 | Hnojewyj |
| 6,840,243 B2 | 1/2005 | Deem et al. |
| 6,840,948 B2 | 1/2005 | Albrecht et al. |
| 6,840,952 B2 | 1/2005 | Saker et al. |
| 6,843,767 B2 | 1/2005 | Corcoran et al. |
| 6,849,262 B2 | 2/2005 | Ollerenshaw et al. |
| 6,852,108 B2 | 2/2005 | Barry et al. |
| 6,860,847 B2 | 3/2005 | Alferness et al. |
| 6,863,676 B2 | 3/2005 | Lee et al. |
| 6,875,209 B2 | 4/2005 | Zvuloni et al. |
| 6,878,106 B1 | 4/2005 | Herrmann |
| 6,878,141 B1 | 4/2005 | Perkins et al. |
| 6,886,558 B2 | 5/2005 | Tanaka |
| 6,901,927 B2 | 6/2005 | Deem et al. |
| 6,902,526 B2 | 6/2005 | Katzman |
| 6,902,536 B2 | 6/2005 | Manna et al. |
| 6,904,909 B2 | 6/2005 | Andreas et al. |
| 6,907,881 B2 | 6/2005 | Suki et al. |
| 6,908,440 B2 | 6/2005 | Fisher |
| 6,918,881 B2 | 7/2005 | Miller et al. |
| 6,929,637 B2 | 8/2005 | Gonzalez et al. |
| 6,936,014 B2 | 8/2005 | Vetter et al. |
| 6,941,950 B2 | 9/2005 | Wilson et al. |
| 6,942,627 B2 | 9/2005 | Huitema |
| 6,945,942 B2 | 9/2005 | Van Bladel et al. |
| 6,962,587 B2 | 11/2005 | Johnson et al. |
| 6,964,662 B2 | 11/2005 | Kidooka |
| 6,967,673 B2 | 11/2005 | Ozawa et al. |
| 6,979,344 B2 | 12/2005 | Jones et al. |
| 6,986,737 B2 | 1/2006 | Suzuki et al. |
| 6,997,189 B2 | 2/2006 | Biggs et al. |
| 6,997,918 B2 | 2/2006 | Soltesz et al. |
| 7,011,094 B2 | 3/2006 | Rapacki et al. |
| 7,022,088 B2 | 4/2006 | Keast et al. |
| 7,033,387 B2 | 4/2006 | Zadno-Azizi et al. |
| 7,036,509 B2 | 5/2006 | Rapacki et al. |
| 7,063,682 B1 | 6/2006 | Whayne et al. |
| 7,100,616 B2 | 9/2006 | Springmeyer |
| 7,112,225 B2 | 9/2006 | Ginn |
| 7,128,747 B2 | 10/2006 | Ginn |
| 7,141,046 B2 | 11/2006 | Perkins et al. |
| 7,165,548 B2 | 1/2007 | Deem et al. |
| 7,175,619 B2 | 2/2007 | Koblish et al. |
| 7,195,017 B2 | 3/2007 | Tanaka |
| 7,198,635 B2 * | 4/2007 | Danek et al. ................... 607/96 |
| 7,300,428 B2 | 11/2007 | Ingenito |
| 7,351,202 B2 | 4/2008 | Long |
| 7,393,330 B2 | 7/2008 | Keast et al. |
| 7,393,363 B2 | 7/2008 | Ginn |
| 7,445,010 B2 | 11/2008 | Kugler et al. |
| 7,451,765 B2 | 11/2008 | Adler |
| 7,503,931 B2 | 3/2009 | Kowalsky et al. |
| 7,517,320 B2 | 4/2009 | Wibowo et al. |
| 7,549,984 B2 | 6/2009 | Mathis |
| 7,608,579 B2 | 10/2009 | Gong et al. |
| 7,662,181 B2 | 2/2010 | Deem et al. |
| 7,670,282 B2 | 3/2010 | Mathis |
| 7,731,651 B2 | 6/2010 | Pearce et al. |
| 7,757,691 B2 | 7/2010 | Reynolds et al. |
| 7,766,891 B2 | 8/2010 | McGurk et al. |
| 7,766,895 B2 | 8/2010 | Soltesz et al. |
| 7,766,938 B2 | 8/2010 | McGurk et al. |
| 7,775,968 B2 | 8/2010 | Mathis |
| 7,896,008 B2 | 3/2011 | Tanaka |
| 8,142,455 B2 | 3/2012 | Thompson et al. |
| 8,157,823 B2 | 4/2012 | Aronson et al. |
| 8,157,837 B2 | 4/2012 | Thompson et al. |
| 8,282,660 B2 | 10/2012 | Thompson et al. |
| 8,632,605 B2 | 1/2014 | Thompson et al. |
| 8,668,707 B2 | 3/2014 | Thompson et al. |
| 8,721,734 B2 | 5/2014 | Mathis et al. |
| 8,740,921 B2 | 6/2014 | Mathis et al. |
| 2001/0051799 A1 * | 12/2001 | Ingenito ....................... 604/516 |
| 2002/0007831 A1 | 1/2002 | Davenport et al. |
| 2002/0026188 A1 | 2/2002 | Balbierz et al. |
| 2002/0042564 A1 | 4/2002 | Cooper et al. |
| 2002/0042565 A1 | 4/2002 | Cooper et al. |
| 2002/0062120 A1 | 5/2002 | Perkins et al. |
| 2002/0077593 A1 | 6/2002 | Perkins et al. |
| 2002/0091379 A1 | 7/2002 | Danek et al. |
| 2002/0111620 A1 | 8/2002 | Cooper et al. |
| 2002/0112729 A1 | 8/2002 | DeVore et al. |
| 2002/0128647 A1 * | 9/2002 | Roschak et al. ................ 606/41 |
| 2002/0138074 A1 | 9/2002 | Keast et al. |
| 2002/0161392 A1 | 10/2002 | Dubrul |
| 2002/0161399 A1 | 10/2002 | Cruise et al. |
| 2002/0176893 A1 | 11/2002 | Wironen et al. |
| 2002/0183244 A1 | 12/2002 | Ollerenshaw et al. |
| 2002/0183838 A1 | 12/2002 | Liddicoat et al. |
| 2002/0188171 A1 | 12/2002 | Alferness et al. |
| 2003/0018318 A1 | 1/2003 | Melsky |
| 2003/0029452 A1 | 2/2003 | Suki et al. |
| 2003/0050648 A1 | 3/2003 | Alferness et al. |
| 2003/0051733 A1 * | 3/2003 | Kotmel et al. ............ 128/207.14 |
| 2003/0055331 A1 | 3/2003 | Kotmel et al. |
| 2003/0069488 A1 | 4/2003 | Alferness et al. |
| 2003/0070676 A1 | 4/2003 | Cooper et al. |
| 2003/0070682 A1 | 4/2003 | Wilson et al. |
| 2003/0070683 A1 | 4/2003 | Deem et al. |
| 2003/0075170 A1 | 4/2003 | Deem et al. |
| 2003/0083671 A1 | 5/2003 | Rimbaugh et al. |
| 2003/0088195 A1 | 5/2003 | Vardi et al. |
| 2003/0100921 A1 | 5/2003 | Addis et al. |
| 2003/0109866 A1 | 6/2003 | Edwards et al. |
| 2003/0127090 A1 | 7/2003 | Gifford et al. |
| 2003/0130657 A1 | 7/2003 | Tom et al. |
| 2003/0154988 A1 | 8/2003 | DeVore et al. |
| 2003/0158515 A1 | 8/2003 | Gonzalez et al. |
| 2003/0159700 A1 | 8/2003 | Laufer et al. |
| 2003/0181356 A1 | 9/2003 | Ingenito |
| 2003/0181922 A1 | 9/2003 | Alferness |
| 2003/0183235 A1 | 10/2003 | Rimbaugh et al. |
| 2003/0191496 A1 | 10/2003 | Edwards et al. |
| 2003/0192551 A1 | 10/2003 | Deem et al. |
| 2003/0195385 A1 | 10/2003 | DeVore |
| 2003/0195511 A1 | 10/2003 | Barry |

(56) References Cited

U.S. PATENT DOCUMENTS

| | | |
|---|---|---|
| 2003/0212337 A1 | 11/2003 | Sirokman |
| 2003/0212412 A1 | 11/2003 | Dillard et al. |
| 2003/0233099 A1 | 12/2003 | Danaek et al. |
| 2004/0010209 A1 | 1/2004 | Sirokman |
| 2004/0010289 A1 | 1/2004 | Biggs et al. |
| 2004/0024356 A1 | 2/2004 | Tanaka |
| 2004/0030262 A1 | 2/2004 | Fisher et al. |
| 2004/0031494 A1 | 2/2004 | Danek et al. |
| 2004/0038868 A1 | 2/2004 | Ingenito |
| 2004/0040555 A1 | 3/2004 | Tanaka |
| 2004/0049187 A1 | 3/2004 | Burnett et al. |
| 2004/0052850 A1 | 3/2004 | Schankereli |
| 2004/0055606 A1 | 3/2004 | Hendricksen et al. |
| 2004/0059263 A1 | 3/2004 | DeVore et al. |
| 2004/0063613 A1 | 4/2004 | Rolke et al. |
| 2004/0072756 A1 | 4/2004 | Wilkie et al. |
| 2004/0073155 A1 | 4/2004 | Laufer et al. |
| 2004/0073191 A1 | 4/2004 | Soltesz et al. |
| 2004/0073201 A1 | 4/2004 | Cooper et al. |
| 2004/0073207 A1* | 4/2004 | Ginn ................ 606/41 |
| 2004/0073241 A1 | 4/2004 | Barry et al. |
| 2004/0078054 A1* | 4/2004 | Biggs et al. ............ 606/232 |
| 2004/0081676 A1 | 4/2004 | Schankereli et al. |
| 2004/0120849 A1 | 6/2004 | Stewart et al. |
| 2004/0133168 A1 | 7/2004 | Salcudean et al. |
| 2004/0134487 A1 | 7/2004 | Deem et al. |
| 2004/0154621 A1 | 8/2004 | Deem et al. |
| 2004/0158228 A1 | 8/2004 | Perkins |
| 2004/0172058 A1 | 9/2004 | Edwards et al. |
| 2004/0176801 A1 | 9/2004 | Edwards et al. |
| 2004/0176833 A1 | 9/2004 | Pavcnik et al. |
| 2004/0210248 A1 | 10/2004 | Gordon et al. |
| 2004/0211434 A1 | 10/2004 | Loomas et al. |
| 2004/0220556 A1 | 11/2004 | Cooper et al. |
| 2004/0225254 A1 | 11/2004 | Tanaka et al. |
| 2004/0231674 A1 | 11/2004 | Tanaka |
| 2004/0234575 A1 | 11/2004 | Horres et al. |
| 2004/0237966 A1 | 12/2004 | Tanaka |
| 2004/0244802 A1 | 12/2004 | Tanaka |
| 2004/0244803 A1 | 12/2004 | Tanaka |
| 2004/0267277 A1 | 12/2004 | Zannis et al. |
| 2005/0004599 A1 | 1/2005 | McNally-Heintzelman et al. |
| 2005/0015106 A1 | 1/2005 | Perkins et al. |
| 2005/0016530 A1* | 1/2005 | McCutcheon et al. ... 128/200.24 |
| 2005/0033310 A1* | 2/2005 | Alferness et al. .......... 606/108 |
| 2005/0033344 A1 | 2/2005 | Dillard et al. |
| 2005/0043751 A1 | 2/2005 | Phan et al. |
| 2005/0043752 A1 | 2/2005 | Phan et al. |
| 2005/0049615 A1 | 3/2005 | Cooper et al. |
| 2005/0051163 A1 | 3/2005 | Deem et al. |
| 2005/0056292 A1 | 3/2005 | Cooper |
| 2005/0060041 A1 | 3/2005 | Phan et al. |
| 2005/0060042 A1 | 3/2005 | Phan et al. |
| 2005/0060044 A1 | 3/2005 | Roschak et al. |
| 2005/0061322 A1 | 3/2005 | Freitag |
| 2005/0085801 A1 | 4/2005 | Cooper et al. |
| 2005/0096529 A1 | 5/2005 | Cooper et al. |
| 2005/0101836 A1 | 5/2005 | Onuki et al. |
| 2005/0103340 A1 | 5/2005 | Wondka |
| 2005/0107783 A1 | 5/2005 | Tom et al. |
| 2005/0119614 A1 | 6/2005 | Mesky |
| 2005/0131339 A1 | 6/2005 | Makin et al. |
| 2005/0137518 A1 | 6/2005 | Biggs et al. |
| 2005/0137611 A1 | 6/2005 | Escudero et al. |
| 2005/0137712 A1 | 6/2005 | Biggs et al. |
| 2005/0137715 A1 | 6/2005 | Phan et al. |
| 2005/0145253 A1 | 7/2005 | Wilson et al. |
| 2005/0148902 A1 | 7/2005 | Minar et al. |
| 2005/0166925 A1 | 8/2005 | Wilson et al. |
| 2005/0171396 A1 | 8/2005 | Pankratov et al. |
| 2005/0177144 A1 | 8/2005 | Phan et al. |
| 2005/0178389 A1 | 8/2005 | Shaw et al. |
| 2005/0192526 A1 | 9/2005 | Biggs et al. |
| 2005/0196344 A1 | 9/2005 | McCutcheon et al. |
| 2005/0244401 A1 | 11/2005 | Ingenito |
| 2005/0281739 A1 | 12/2005 | Gong et al. |
| 2005/0281740 A1 | 12/2005 | Gong et al. |
| 2005/0281796 A1 | 12/2005 | Gong et al. |
| 2005/0281797 A1 | 12/2005 | Gong et al. |
| 2005/0281798 A1 | 12/2005 | Gong et al. |
| 2005/0281799 A1 | 12/2005 | Gong et al. |
| 2005/0281800 A1 | 12/2005 | Gong et al. |
| 2005/0281801 A1 | 12/2005 | Gong et al. |
| 2005/0281802 A1 | 12/2005 | Gong et al. |
| 2005/0282748 A1 | 12/2005 | Gong et al. |
| 2005/0288549 A1 | 12/2005 | Mathis |
| 2005/0288550 A1 | 12/2005 | Mathis |
| 2005/0288684 A1 | 12/2005 | Aronson et al. |
| 2005/0288702 A1 | 12/2005 | McGurk et al. |
| 2006/0004305 A1 | 1/2006 | George et al. |
| 2006/0004388 A1 | 1/2006 | Whayne et al. |
| 2006/0004400 A1 | 1/2006 | McGurk et al. |
| 2006/0009748 A1 | 1/2006 | Mathis |
| 2006/0009801 A1 | 1/2006 | McGurk et al. |
| 2006/0020243 A1 | 1/2006 | Speck et al. |
| 2006/0025815 A1 | 2/2006 | McGurk et al. |
| 2006/0029548 A1* | 2/2006 | Pelleg et al. .................. 424/9.1 |
| 2006/0030863 A1 | 2/2006 | Fields et al. |
| 2006/0032497 A1 | 2/2006 | Doshi |
| 2006/0076023 A1 | 4/2006 | Rapacki et al. |
| 2006/0095002 A1 | 5/2006 | Soltesz et al. |
| 2006/0100666 A1 | 5/2006 | Wilkinson et al. |
| 2006/0116749 A1 | 6/2006 | Willink et al. |
| 2006/0118126 A1 | 6/2006 | Tanaka |
| 2006/0124126 A1 | 6/2006 | Tanaka |
| 2006/0135947 A1 | 6/2006 | Soltesz et al. |
| 2006/0135984 A1 | 6/2006 | Kramer et al. |
| 2006/0162731 A1 | 7/2006 | Wondka et al. |
| 2006/0167416 A1 | 7/2006 | Mathis et al. |
| 2006/0184016 A1 | 8/2006 | Glossop |
| 2006/0200076 A1 | 9/2006 | Gonzalez et al. |
| 2006/0206147 A1 | 9/2006 | DeVore et al. |
| 2006/0235432 A1 | 10/2006 | DeVore et al. |
| 2006/0235467 A1 | 10/2006 | DeVore et al. |
| 2006/0249164 A1 | 11/2006 | Springmeyer |
| 2006/0264772 A1 | 11/2006 | Aljuri et al. |
| 2006/0276807 A1 | 12/2006 | Keast et al. |
| 2006/0280772 A1 | 12/2006 | Roschak et al. |
| 2006/0280773 A1 | 12/2006 | Roschak et al. |
| 2006/0283462 A1 | 12/2006 | Fields et al. |
| 2007/0005083 A1 | 1/2007 | Sabanathan et al. |
| 2007/0096048 A1 | 5/2007 | Clerc |
| 2007/0221230 A1 | 9/2007 | Thompson et al. |
| 2008/0036763 A1 | 2/2008 | Chen et al. |
| 2008/0063693 A1 | 3/2008 | Cook et al. |
| 2008/0161865 A1 | 7/2008 | Hagen |
| 2008/0183204 A1 | 7/2008 | Greenhalgh et al. |
| 2008/0200797 A1* | 8/2008 | Kotmel et al. ................ 600/411 |
| 2008/0262473 A1 | 10/2008 | Kornblau et al. |
| 2009/0012626 A1 | 1/2009 | Thompson et al. |
| 2009/0076622 A1 | 3/2009 | Thompson et al. |
| 2009/0076623 A1 | 3/2009 | Mathis et al. |
| 2009/0104183 A1 | 4/2009 | Gong et al. |
| 2009/0221967 A1 | 9/2009 | Thommen et al. |
| 2009/0306644 A1* | 12/2009 | Mayse et al. ................... 606/33 |
| 2010/0100196 A1 | 4/2010 | Thompson et al. |
| 2010/0305715 A1 | 12/2010 | Mathis et al. |
| 2012/0172909 A1 | 7/2012 | Mathis et al. |
| 2013/0096603 A1 | 4/2013 | Mathis et al. |
| 2013/0102887 A1 | 4/2013 | Thompson et al. |
| 2013/0103059 A1 | 4/2013 | Mathis et al. |
| 2013/0217956 A1 | 8/2013 | Thompson et al. |
| 2014/0188246 A1 | 7/2014 | Aronson et al. |

FOREIGN PATENT DOCUMENTS

| | | |
|---|---|---|
| GB | 2324729 | 1/2002 |
| JP | H04-22908 | 2/1992 |
| JP | H101998-5343 | 1/1998 |
| JP | 2004-516067 A | 6/2004 |
| JP | 2005-503881 A | 2/2005 |
| JP | 2005-287568 | 10/2005 |
| JP | 2007-513721 A | 5/2007 |
| WO | WO 94/01508 A1 | 1/1994 |

(56) References Cited

FOREIGN PATENT DOCUMENTS

| | | |
|---|---|---|
| WO | WO 98/01084 A1 | 1/1998 |
| WO | WO 98/23227 | 6/1998 |
| WO | WO 00/13592 | 3/2000 |
| WO | WO 01/13839 | 3/2001 |
| WO | WO 01/54618 A1 | 8/2001 |
| WO | WO 02/00270 | 1/2002 |
| WO | WO 02/00275 | 1/2002 |
| WO | WO 02/02158 | 1/2002 |
| WO | WO 02/49554 A1 | 6/2002 |
| WO | WO 03/028522 A2 | 4/2003 |
| WO | WO 03/077768 | 9/2003 |
| WO | WO 2004/062505 | 7/2004 |
| WO | 2004/080347 A2 | 9/2004 |
| WO | WO 2004/086977 | 10/2004 |
| WO | 2004/080347 A3 | 6/2005 |
| WO | WO 2005/058206 A1 | 6/2005 |
| WO | WO 2005/122870 | 12/2005 |
| WO | WO 2008/036763 A2 | 9/2006 |
| WO | WO 2007/016409 A1 | 2/2007 |
| WO | WO 2007/106495 | 9/2007 |

OTHER PUBLICATIONS

Quint et al. "Diaphragmetic Shape Change After Lung Volume Reduction Surgery". Journal of Thoracic Imaging 16(2001):149-155.*
Yusen et al. "A Prospective Evaluation of Lung Volume Reduction Surgery in 200 Consecutive Patients." Chest 123(2003): 1026-1037.*
Wikipedia. "Medical ventilator". Downloaded from <http://en.wikipedia.org/wiki/Medical_ventilator> on Jan. 16, 2015.*
Hermanson, Greg T. Bioconjugate Techniques. San Diego: Academic Press, Inc. 1996. (Table of contents only).
Lam, et al. X-Ray Diagnosis: A Physician's Approach. Singapore: Springer. 1998. (Table of contents only).
Rowe, et al. Handbook of Pharmaceutical Excipients. 4th Edition. London: Pharmaceutical Press. 2003. (Table of contents only).
Slone, et al. Body CT: A Practical Approach. New York: McGraw-Hill. 2000. (Table of contents only).
Stout, et al. X-Ray Structure Determination: A Practical Guide. 2nd Edition. New York: John Wiley & Sons. 1989. (Table of contents only).
The United States Pharmacopeia. 29th Revision. 2006. The United States Pharmacopeia Convention. Rockville, MD. (Table of contents only).
U.S. Appl. No. 60/885,305, filed Jan. 17, 2007; first named inventor: David Thompson.
U.S. Appl. No. 14/134,977, filed Dec. 19, 2013 by Aronson et al. (Unpublished).
U.S. Appl. No. 14/162,124, filed Jan. 23, 2014 by Thompson et al. (Unpublished).
Supplementary European Search Report of EP Application No. 07752999.8, mailed Sep. 22, 2009, 12 pages.
International Search Report and Written Opinion of PCT Application No. PCT/US2009/056839, mailed on Jan. 4, 2010, 15 pages.
International Search Report of PCT Application No. PCT/US07/06339, dated May 14, 2008, 5 pages.
International Search Report and Written Opinion of PCT Application No. PCT/US2010/035297, mailed Jul. 20, 2010, 14 pages.
International Written Opinion of PCT Application No. PCT/US07/06339, dated May 21, 2008, 12 pages.
O'Brien et al. "Improvements in Lung Function, Exercise, and Quality of Life in Hypercapnic COPD Patients After Lung Volume Reduction Surgery". Chest 115 (1999): 75-84.
Quint et al. "Diaphragmetic Shape Change After Lung Volume Reduction Surgery". Journal of Thoracic Imaging 16 (2001):149-155.
Yusen et al. "A Prospective Evaluation of Lung Volume Reduction Surgery in 200 Consecutive Patients." Chest 123 (2003):1026-1037.
Office Action for Japanese Patent Application No. 2009-500440, May 11, 2012, 3 pages.
English Translation of Office Action for corresponding Japanese Application No. 2012-511968 mailed on Nov. 21, 2013, 5 pages.
English Translation of Office Action for corresponding Chinese Application No. 201080030290.4 mailed on Jan. 26, 2014, 11 pages.
U.S. Appl. No. 14/260,644, filed Apr. 24, 2014 by Mathis et al. (Unpublished).
U.S. Appl. No. 14/453,372, filed Aug. 6, 2014 by Thompson et al. (Unpublished).
Restriction Requirement for U.S. Appl. No. 13/618,902 mailed on Sep. 18, 2014, 12 pages.
Extended European Search Report for corresponding European Patent Application No. 14188364.5 dated May 29, 2015, 12 pages.

* cited by examiner

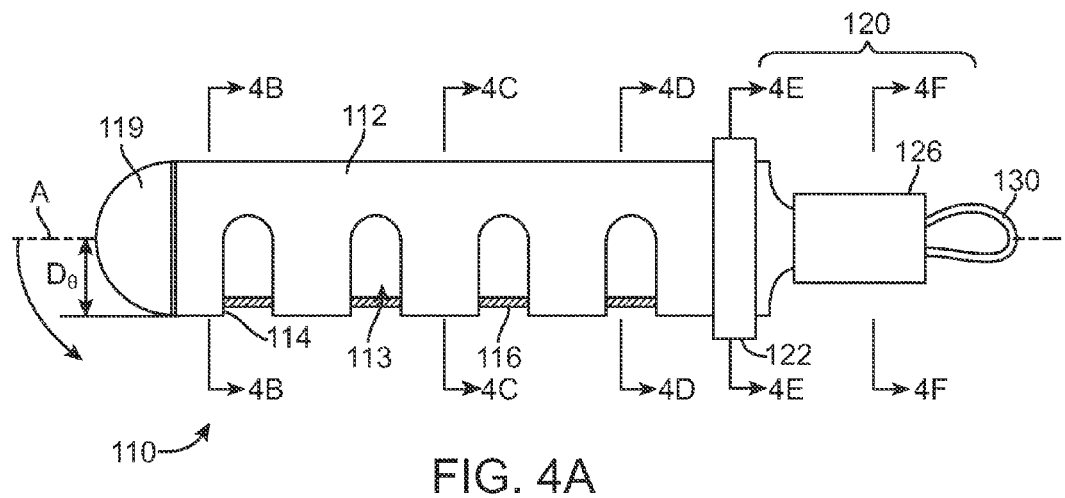
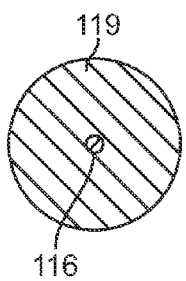
FIG. 4B
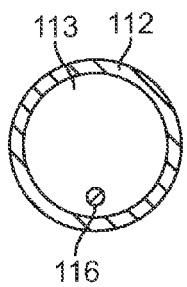
FIG. 4C
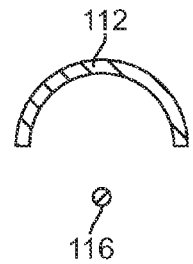
FIG. 4D
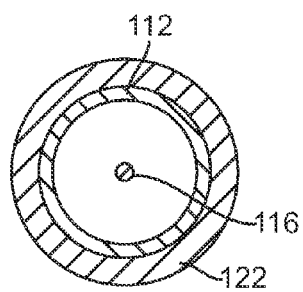
FIG. 4E
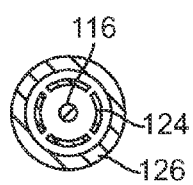
FIG. 4F

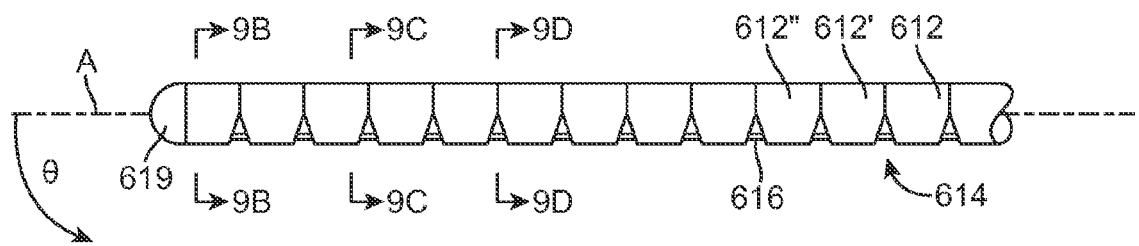
FIG. 9A
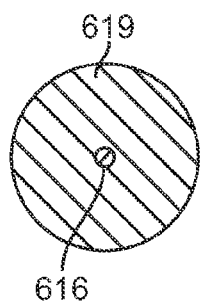
FIG. 9B
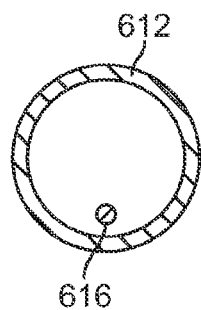
FIG. 9C
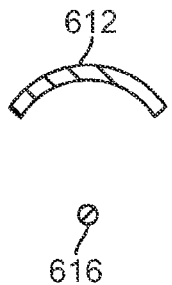
FIG. 9D
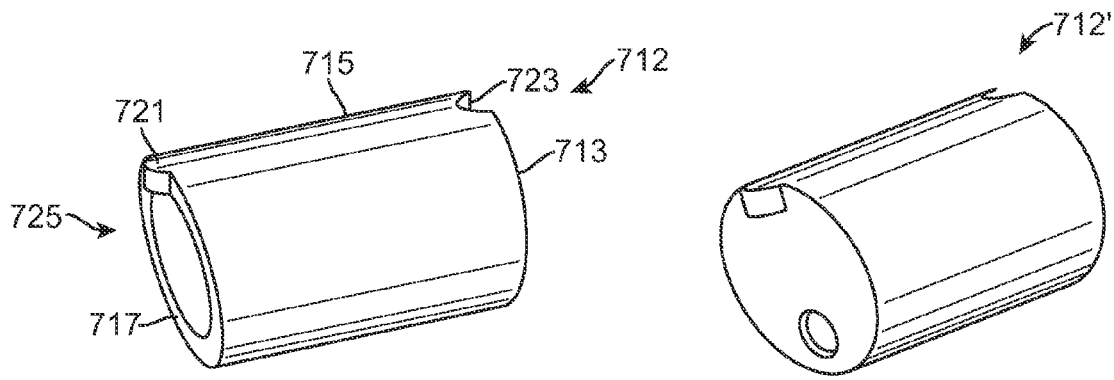
FIG. 10A
FIG. 10B

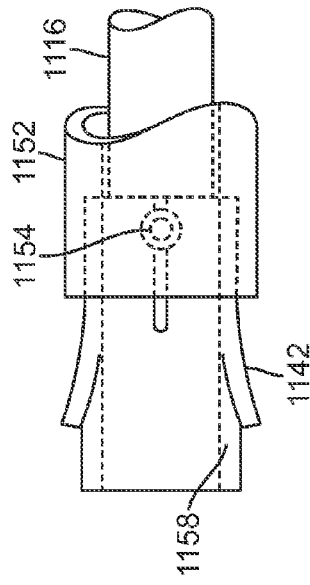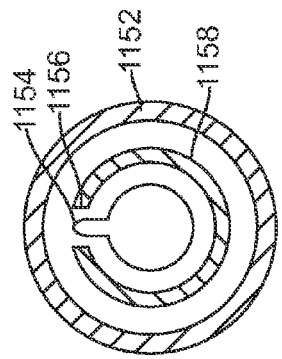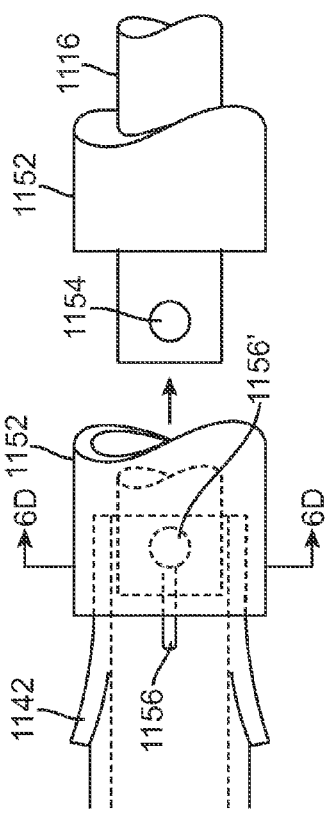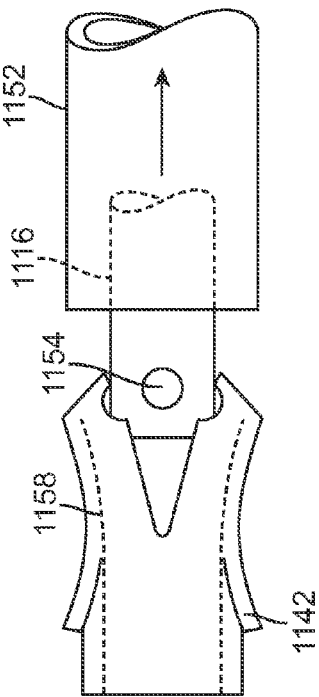
FIG. 15A
FIG. 15B
FIG. 15C
FIG. 15D

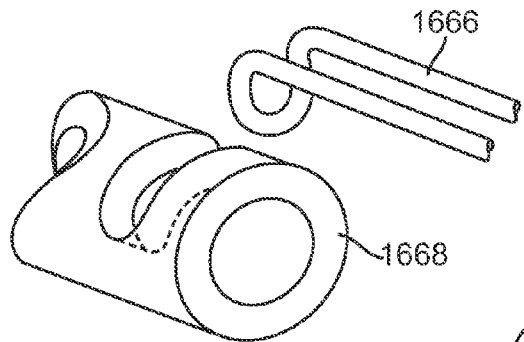
FIG. 20C
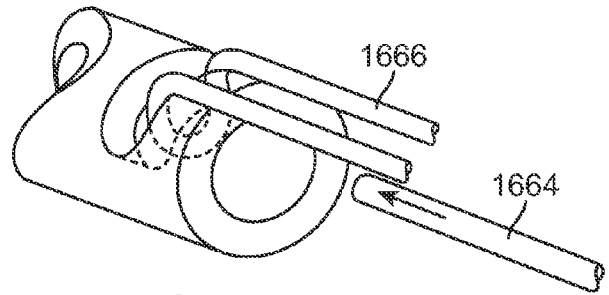
FIG. 20D
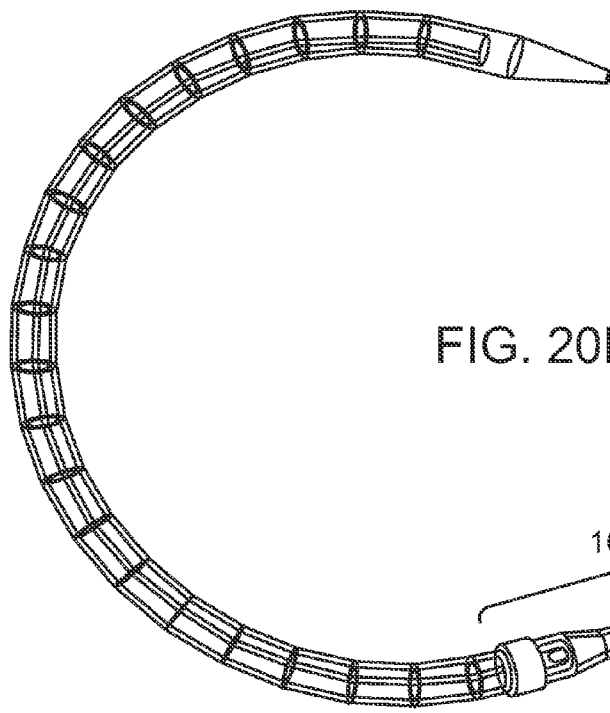
FIG. 20E
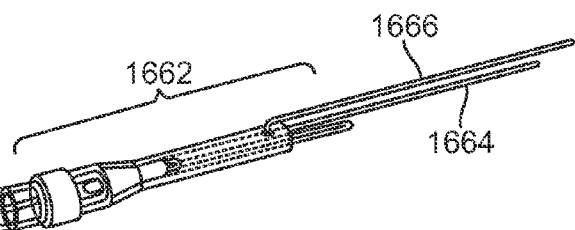

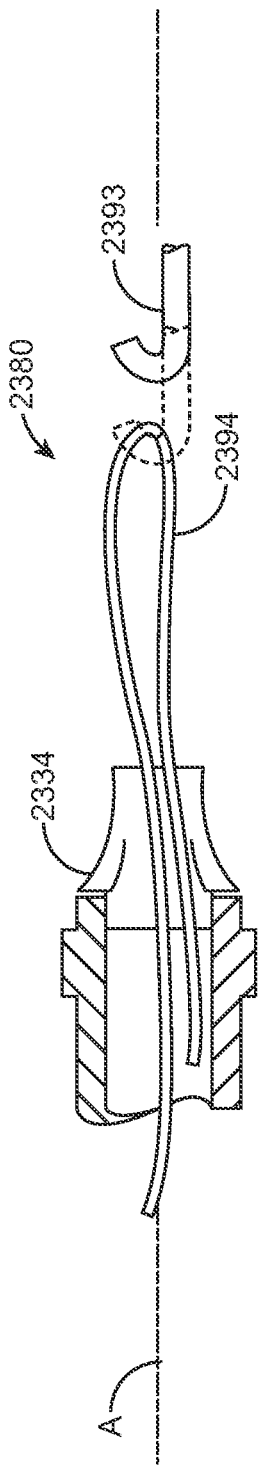
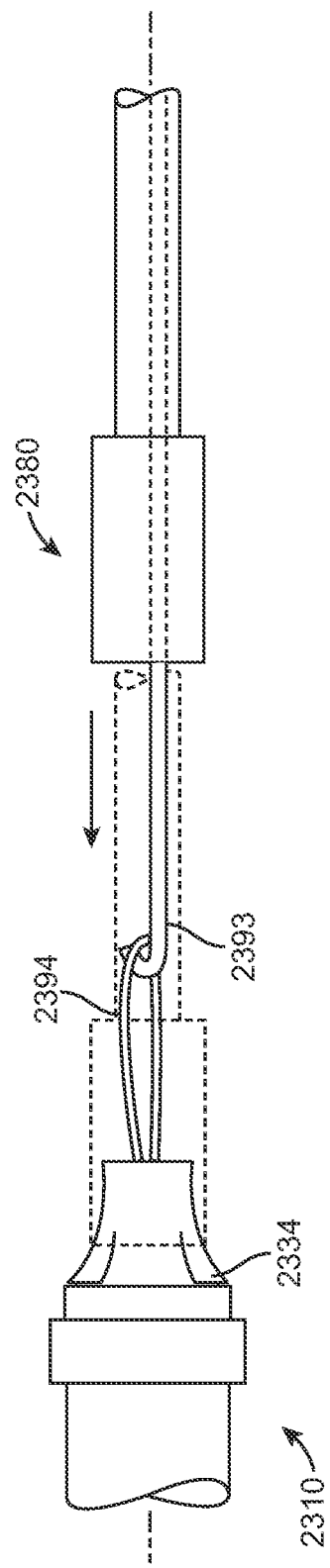

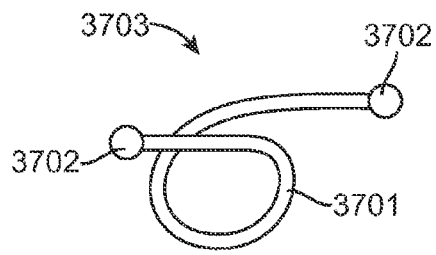
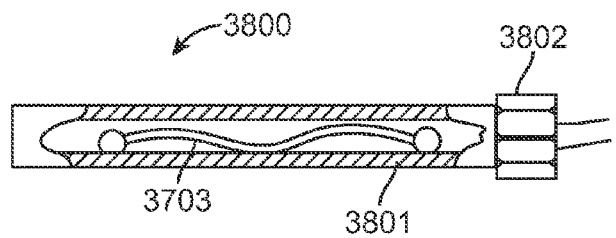
FIG. 37  FIG. 38
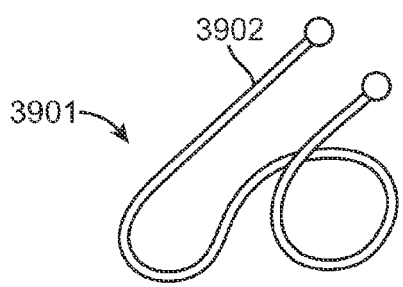
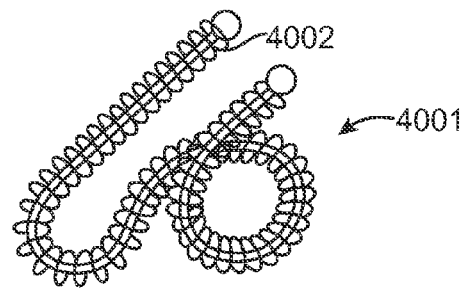
FIG. 39  FIG. 40
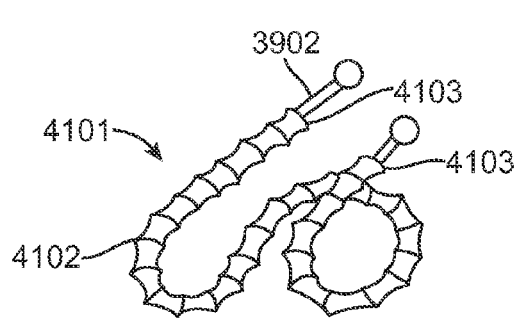
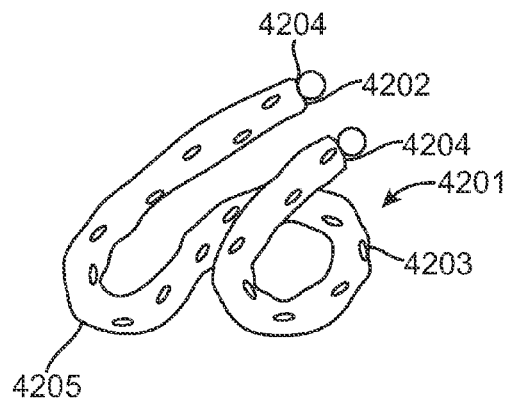
FIG. 41  FIG. 42

ENHANCED EFFICACY LUNG VOLUME REDUCTION DEVICES, METHODS, AND SYSTEMS

CROSS-REFERENCES TO RELATED APPLICATIONS

The present application claims the benefit under 35 USC 119(e) of U.S. Provisional Application Nos. 61/096,550 filed Sep. 12, 2008, entitled Enhanced Efficacy Lung Volume Reduction Devices, Methods, and Systems; and 61/096,559 filed Sep. 12, 2008, entitled Elongated Lung Volume Reduction Devices, Methods, and Systems.

This application is related to U.S. patent application Ser. Nos. 12/209,631 filed Sep. 12, 2008, entitled Delivery of Minimally Invasive Lung Volume Reduction Devices U.S. Pat. No. 8,142,455 B2; and 12/209,662 filed Sep. 12, 2008, entitled Lung Volume Reduction Devices, Methods, and Systems U.S. Pat. No. 8,157,823 B2.

All publications and patent applications mentioned in this specification are herein incorporated by reference to the same extent as if each individual publication or patent application was specifically and individually indicated to be incorporated by reference.

BACKGROUND OF THE INVENTION

Field of the Invention

Devices, systems and methods are described for treating lungs. The exemplary devices, systems and methods may, for example, improve the quality of life and restore lung function for patients suffering from emphysema. Embodiments of the systems include an implant and a delivery catheter that can be advanced through tortuous anatomy. The advanced implants can then be actuated to retain a pre-determined shape. The actuated implant modifies the shape of the airways and locally compresses lung parenchyma to cause volume reduction and thereby tensions other lung parenchyma to restore elastic recoil. Systems and devices are also included that deploy and actuate the implantable devices, as well as systems and devices designed for recapture of the implanted device.

Current medical literature describes emphysema as a chronic (long-term) lung disease that can get worse over time. It's usually caused by smoking Having emphysema means some of the air sacs in your lungs are damaged, making it hard to breathe. Some reports indicate that emphysema is the fourth largest cause of mortality in the U.S., affecting an estimated 16-30 million U.S. citizens. Each year approximately 100,000 sufferers die of the disease. Smoking has been identified as a major cause, but with ever increasing air pollution and other environmental factors that negatively affect pulmonary patients, the number of people affected by emphysema is on the rise.

A currently available solution for patients suffering from emphysema is a surgical procedure called Lung Volume Reduction (LVR) surgery whereby diseased lung is resected and the volume of the lung is reduced. This allows healthier lung tissue to expand into the volume previously occupied by the diseased tissue and allows the diaphragm to recover. High mortality and morbidity may be associated with this invasive procedure. Several minimally invasive investigational therapies exist that aim at improving the quality of life and restoring lung function for patients suffering from emphysema. The underlying theory behind many of these devices is to achieve absorptive atelectasis by preventing air from entering diseased portion of the lung, while allowing air and mucous to pass through the device out of the diseased regions. Unfortunately, collateral ventilation (interlobar and intralobar—porous flow paths that prevent complete occlusion) may prevent atelectasis, so that not all patients actually achieve measurable atelectasis. The lack of atelectasis or lung volume reduction may drastically reduce the effectiveness of such devices. Biological treatments utilize tissue engineering aimed at causing scarring at specific locations. Unfortunately, it can be difficult to control the scarring and to prevent uncontrolled proliferation of scarring. Hence, improved and/or alternative lung treatment techniques would be desirable.

BRIEF SUMMARY OF THE INVENTION

The present invention provides improved medical devices, systems, and methods, particularly for treatment of one or both lungs of a patient. Embodiments of the invention often make use of elongate implant structures which can be introduced into an airway system to a target airway axial region. The target axial region may or may not include branches, and the implants can be deployed within the airway by allowing the implant to bend so that the implant compresses adjacent lung tissue. Although it is counterintuitive, the overall treatment may benefit from use of an implant which is longer than the length of the target axial region of the airway in which the implant is deployed. This may, for example, help limit excessive axially stress against distal airway tissues too close to a surface of the lung. Additionally, the use of such an elongate implant may increase the total volume of lung tissue compressed by the implant, and may help keep a proximal end of the implant near (such as within a field of view of) a delivery structure, thereby facilitating retrieval of the implant if the deployment does not appear to be desirable. Many embodiments of the invention employ multiple implant systems for locally compressing lung tissue from within airways of the lung, thereby providing beneficial tension in other (often healthier) portions of the lung. At least some of the implants may be deployed within the lung sequentially, and the effectiveness of the therapy can be monitored and evaluated qualitatively and/or quantitatively during the treatment. Evaluation of lung function during a lung treatment may employ direct measurements by intermittently using a ventilator or the like, or function may be indirectly evaluated from imaging, blood oxygen measurements or the like.

Exemplary lung volume reduction systems includes an implantable device having an elongate body that is sized and shaped for delivery via the airway system to a lung airway of a patient. The implant is inserted and positioned while the implant is in a delivery configuration, and is reconfigured to a deployed configuration so as to locally compress adjacent tissue of the lung. During reconfiguring or deployment of the implant, portions of the elongate body generally move laterally within the airway so as to laterally compress lung tissue, ideally with the diseased lung tissue being compressed between two or more axially separated portions of the elongate body, the elongate body often being resiliently biased so as to bend the lung airway. A plurality of such implants will often be used to treat a lung of a patient. Methods of compressing lung tissue are also provided, with the lung tissue often being compressed between airway axial regions from within the airway axial regions, typically using elongate structures extending along those axial regions and often by bending an elongate body inserted of a device inserted into the airway system in a relatively straight delivery configuration into a deployed configuration, thereby bending the airway system.

Another aspect of the invention provides a method for treating a lung of a patient. The lung includes an airway system having a plurality of branching airways. A first portion of the lung is compressed from within the airway system while permitting airflow into the compressed first portion from the first uncompressed portion. Lung characteristics of the patient are evaluated with the first portion compressed. A second portion of the lung from within the airway system is compressed in response to the evaluation of the lung characteristics while permitting airflow into the compressed second portion from the second uncompressed portion.

The evaluation of the lung characteristics and the compression of the second portion of the lung may both occur within 6 hours of the compressing of the first portion of the lung. In many embodiments, the compression of the second portion of the lung may be completed in the same procedure as the compression of the first portion of the lung so that the patient is not relocated therebetween. In fact, evaluation of the lung characteristic may be initiated within a few breathing cycles of completion of the compressing of the first tissue. The evaluation indicates enhanced lung function induced at least in part by mechanical compression within the lung and without requiring other tissue response-induced delay for effective determination of efficacy.

A variety of systems and methods may be used to evaluate the lungs during treatment. The evaluation of the lung characteristic may optionally comprise identifying a change in density of lung tissue by remotely imaging the lung tissue in situ, typically using X-ray imaging, fluoroscopy, computed tomography (CT), or the like, and optionally using magnetic resonance imaging (MRI), ultrasound, or other imaging modalities.

Additional implants may be deployed whenever the evaluation of the lung characteristic indicates an improvement of less than about 5%, 8%, or even 10% from a pre-treatment forced expiratory volume in one second (FEV1) to an FEV1 after compression of the first portion of the lung. Note that this may result in additional implants being deployed after greater improvements than are available using other treatments, and those other treatment improvements may (in at least some cases) not be apparent for a significant time after the treatment. Note also that FEV 1 may be measured directly or the effective improvement in lung function may be indicated indirectly by other lung characteristics.

In some embodiments, additional implants may be deployed whenever the evaluation of the lung characteristic indicates an improvement of less than about 6%, 10%, or even 20% from a pre-treatment residual volume to a residual volume after compression of the first portion of the lung.

The evaluation of the lung characteristic may indicate an improvement of less than about 8%, 10%, or 12% from a pre-treatment six minute walk distance to a six minute walk distance after compression of the first portion of the lung.

The evaluation of the lung characteristic may comprise an increase of less than about 1% from a pre-treatment measurement of blood oxygen to a measurement of blood oxygen after compression of the first part of the lung.

The evaluation of the lung characteristic may indicate that airways of the lung outside the first portion remain subject to collapse due to lack of tension in adjacent lung tissue.

The evaluation of the lung characteristic may comprise imaging of an uncompressed region of distributed disease after compression of the first portion of the lung. The uncompressed diseased region may comprise the second portion of the lung and is separated from the first portion such that the treatment effects localized compression of diseased regions separated within the lung so as to increase pre-expiration tension in distributed tissue of the lung that is healthier than the diseased regions. The evaluation of the lung characteristic can comprise identifying a change in shape of a diaphragm along a lower surface of the lung from an overall convex shape bulging outwardly away from the lung before treatment to a surface which is not yet curving sufficiently inwardly into the lung after compression of the first portion of the lung by remotely imaging the lung tissue in situ.

Another aspect of the invention provides a system for treating a lung of a patient. The lung includes an airway system having a plurality of branching airways. The system comprises a first implant, a lung evaluation system and a second implant. The first implant is deployable from a first configuration to a second configuration when the first implant extends axially along the airway system. Deployment of the implant laterally compresses a first portion of the lung from within the airway system. The lung evaluation system is coupleable to the lung. The lung evaluation system outputs lung characteristics responsive to compression of the first portion of the lung. The second implant, in response to the lung characteristics, is positionable axially along the airway system and deployable from a first configuration to a second configuration such that the second implant laterally compresses a second portion of the lung from within the airway system.

The evaluation system may output the lung characteristics so as to enable the compression of the second portion of the lung within 6 hours of the compressing of the first portion of the lung. Each implant may have a plurality of elongate body portions coupled together so as to laterally compress the associated lung tissue portions, for example, by bending between the implant body portions when released from a catheter.

In many embodiments, the system further comprises an implant delivery system insertable into the patient while the patient is positioned for treatment. The lung evaluation system is coupleable to the lung while the patient is positioned for treatment such that compression of the second portion of the lung can be completed in the same procedure as the compression of the first portion of the lung when the patient is not relocated therebetween.

The lung characteristic from the lung evaluation system may be responsive to compression of the first portion of the lung within a few breathing cycles of completion of the compressing of the first portion of the lung to indicate enhanced lung function effected by mechanical changes within the lung.

The lung evaluation system may comprise a remote imaging system indicating at least one of changes in lung tissue density or that airways of the lung outside the first portion remain subject to collapse due to lack of tension in adjacent lung tissue in situ.

Another aspect of the invention provides a system for treating a lung of a patient. The lung includes an airway system having a plurality of branching airways. The system comprises means for compressing a first portion of the lung from within the airway system, means for evaluating lung characteristics of the patient with the first portion compressed, and means for compressing a second portion of the lung from within the airway system in response to the evaluation of the lung characteristics.

In another aspect the invention provides a method for treating a lung of a patient. The lung including an airway system having a plurality of branching airways. The method comprises advancing an implant through the airway system. The implant may have an elongate length, and a distal portion of the implant may be deployed within the airway system so that the distal portion engages an airway. The implant can be progressively deployed proximally of the distal portion, preferably while a proximal end of the implant advances distally relative to the adjacent airway system. This advancement of the proximal end can help to inhibit axial loading between the implant and the airway, particularly when the implant compresses lung tissue along the length of the implant.

The distal portion of the implant will often be deployed near a surface of the lung. The proximal end of the implant can be allowed to advance by at least 10% of the length of the implant so as to inhibit localized strain near the surface of the lung. Allowing this movement of the proximal end may help to avoid rupture of the lung surface (which might otherwise occur in light of the relatively small amount of tissue potentially available to provide strain relief between the end of the implant and the lung surface). Preferably, the implant will be between 10% and 30% longer than the airway tissue engaged by the proximal and distal ends of the implants (where measurements are taken along central axes of each prior to the treatment).

In some embodiments, the implant advances through a lumen of a bronchoscope. During compression of the lung the proximal end is allowed to advance within the bronchoscope, and making use of a longer implant than the airway axial region facilitates viewing the proximal end of the implant using the bronchoscope before mechanically decoupling the implant from the bronchoscope.

Another aspect of the invention provides a method for treating a lung of a patient. The lung includes an airway system having a plurality of branching airways. A target axial region of the airway system is identified. The target axial region has a proximal end and a distal end with a length therebetween. In response to the length of the target axial region, an implant is selected. The implant has an elongate body with a body length greater than the length of the target axial region. A distal end of the selected implant is advanced through the airway system toward the distal end of the target axial region. The implant within the target system is deployed so that the elongate body laterally compresses a portion of the lung.

In many embodiments, a length of the target axial region is measured. The implant is selected so that the elongate body has a length of at least 10% more that the measured target axial region. The length of the target axial region may be measured by advancing a measurement, body distally from a distal end of a bronchoscope until a distal end of the measurement body is sufficiently engaged by a surrounding lumen of the airway system to inhibit further distal advancement, and measuring a length between the distal end of the advanced measurement body and the distal end of the bronchoscope. The implant may be deployed by advancing a catheter over the measurement body so that a distal end of the catheter is adjacent the distal end of the measurement body, withdrawing the measurement body, advancing the distal end of the elongate body through a lumen of the catheter to adjacent the distal end of the catheter, and withdrawing the catheter proximally from the advanced implant.

The proximal end of the elongate body may be disposed within a lumen of the bronchoscope when the withdrawing of the catheter is initiated. The elongate body may bend laterally during the withdrawing of the catheter so as to laterally compress a portion of the lung. A distal released portion of the elongate body is axially coupled to the airway system without perforating the airway while a proximal end portion of the elongate body adjacent the proximal end remains within the lumen of the catheter. The proximal end of the elongate body may move distally during withdrawal of the implant. The proximal end of the catheter body remains within a field of view of the bronchoscope when the implant is mechanically decoupled from the catheter and bronchoscope.

In another aspect, the invention provides a system for treating a lung of a patient. The lung includes an airway system having a plurality of branching airways. The system comprises a catheter having a distal end that can be advanced into the airway system. An implant can be received by a lumen of the catheter, and the implant comprises an elongate body having a distal portion and a proximal portion adjacent a proximal end. The distal portion can engage the airway upon retraction of the distal end of the catheter from the distal portion. The proximal end of the implant may be advanceable distally relative to the catheter and surrounding airway while the catheter is withdrawn proximally from the proximal portion of the implant.

Optionally, the catheter may comprise a bronchoscope or be included in a delivery system including a bronchoscope. The implant may have a length of over 110 mm, often having a length in a range from about 120 mm to about 250 mm.

In another aspect, the invention provides an implant for treating a lung of a patient. The lung including an airway system having a plurality of branching airways, and the implant comprises an elongate body advanceable through the airway system. The body has a proximal end and a distal end, and autramatic surfaces are disposed adjacent the distal and proximal ends of the elongate body so as to engage the surrounding airway system and inhibit penetration through the airway system when the elongate body compresses lung tissue between the ends from within the airway. The implant has a length of over 110 mm between the atraumatic surfaces.

In many embodiments, the autramatic ends will have cross-sectional diameters of over about 1 mm, often being in a range from about 1 to about 3 mm, and ideally being substantially spherical with a diameter of about 1.5 mm.

In another aspect, the invention provides a method for delivering an implant to a lung of a patient. The lung has an airway system including an airway, and the method comprises advancing a distal end of a guidewire distally within the airway system. The guidewire has indicia of lengths to the distal end of the guidewire. An implant length is selected using the indicia, and an implant having the selected length is advanced into the lung via the airway system so that an elongate body of the implant extends axially along the airway. The implant is deployed so that the implant compresses adjacent lung tissue from within the airway.

In another aspect, the invention provides a system for treating a lung of a patient. The lung has an airway system including an airway, and the system comprises an elongate catheter body having a proximal end and a distal end, the distal end being advanceable through the airway system to the airway. An implant is positionable near the distal end of the catheter, the implant having an elongate body deployable from a delivery configuration to a deployed configuration so as to compress adjacent lung tissue from within the airway. An elongate measurement body can extend distally along the catheter. The measurement body has indicia of a distal length of the measurement body between the catheter and a distal end of the measurement body suitable for selecting a length of the elongate body of the implant. Optionally, the catheter may comprise a bronchoscope or be included in a delivery system including a bronchoscope.

In yet another aspect, the invention provides a system for delivering an implant to a lung of a patient. The lung has an airway system including an airway. The system comprises an elongate catheter body having a proximal end and a distal end, the distal end being advanceable through the airway system to the airway. A plurality of alternatively selectable implants are included, each implant comprising an elongate body that is stored sufficiently uconstrained so as limit strain of the elongate body. The lengths of the elongate bodies typically vary. Each implant, if or when selected, can be loaded into the catheter by straightening the associated elongate body toward the axis and inserting the elongate body into the lumen so that the catheter maintains the elongate body in the delivery configuration. An elongate measurement body can extend distally along the catheter, the measurement body having indicia of a distal length of the measurement body suitable for selecting a length of the elongate body of the implant.

Another aspect of the invention provides a method for treating a lung of a patient. The lung includes a first airway axial region and a second airway axial region. A lung tissue volume is compressed by urging the first airway axial region laterally toward the second airway axial region using an implant system extending into the first and second airway axial regions.

Each airway axial region extends along an associated axial region central axis, and the airway axial regions may each comprise elongate lengths of the airway system (such that they are significantly longer along the airway axis than they are wide). The compressed volume of lung tissue is often disposed at least in part between the first airway axial region and the second airway axial region. The volume of lung tissue is compressed by laterally urging the airway axial regions together using elongate implant portions extending axially within the airway axial regions. For example, the implant system may comprise an elongate body having a proximal portion and a distal portion. The distal portion of the elongate body often passes through the first airway axial region and engages the second airway axial region, as the first and second airway axial regions are coupled together axially. The proximal portion of the elongate body engages the first airway axial region. The lung tissue volume may be compressed by bending of the elongate body between the proximal portion and the distal portion. The bending of the elongate body within the airway axial regions urges a bearing surface of the elongate body laterally against an airway lumen surface so as to impose a bend in the airway system between the airway axial regions. The bearing surface may not penetrate through the airway surface during deployment of the elongate body. A portion of the implant, particularly near an end of the elongate body, may over time penetrate into and/or through a engaged airway lumen wall. Efficacy of the implant may, at least in part, be independent of collateral flow so that the implant may continue to provide therapeutic benefits despite such penetration.

The implant may benefit from a three-dimensional or nonplanar geometry so as to provide a desired level of compression on a desired volume of lung tissue. For example, a surface can generally be defined between the first and second airway region axes. A similar surface can be defined between local axes of the elongate body portions of the implant. Regardless, in many embodiments, a third airway axial region may be urged toward the surface from within the third airway axial region so that the compressed volume of lung tissue is disposed at least in part between the surface and the third airway axial region. In some embodiments, a fourth airway axial region may be urged toward the first, second, and third airway axial regions, the compressed lung tissue volume being disposed therebetween, optionally with a continuous elongate body that extends through each of the airway axial regions.

In many embodiments, a third airway axial region is urged laterally toward a fourth airway axial region from within third and forth airway axial regions, respectively. These airway axial regions may be manipulated by additional portions of the same elongate body, or by using a separate elongate body implanted within the lung. Advantageously, the compressed volume of lung tissue may be sufficiently large and may be compressed sufficiently to increase tension in an uncompressed volume of the lung such that lung function of the lung is increased.

Another aspect of the invention provides a method for treating a lung of a patient. The lung includes an airway system. The method comprises increasing tension within a portion of a lung by pushing against elongate luminal surface regions of the airway system from within the airway system sufficiently to compress another portion of the lung.

Another aspect of the invention provides an implant for treating a lung of a patient. The lung includes a first airway axial region and a second airway axial region. The implant comprises a first elongate body portion having a first local axis and a second elongate body portion having a second local axis. The elongate body portions are coupled together so that the implant is deployable from a first configuration to a second configuration when the first elongate body portion extends axially along the first airway axial region and the second elongate body portion extends axially along the second airway axial region. The elongate body portions in the second configuration compress a lung tissue volume laterally between the first airway axial region and the second airway axial region.

An intermediate elongate body portion may couple the first elongate body portion to the second elongate body portion Hence, these elongate body portions may be included within a continuous elongate body. The elongate body can be biased to bend from the first configuration to the second configuration so as to compress the lung tissue volume. Advantageously, compression can be effected atraumatically by urging an elongate bearing surface of the elongate body laterally against an airway lumen surface so as to impose a bend in the airway system between (and optionally along) the airway axial regions. The bearing surface need not be continuous, and may have an overall size sufficient to inhibit penetration through the airway surface during deployment of the elongate body. A third elongate body portion may be coupled to the first and second body portions. Analogous to the description above regarding three-dimensional compression of the lung tissue, a surface can be defined between the first and second local axes when the implant is in the second configuration. The implant in the second configuration is configured to urge a third airway axial region toward the surface from within the third airway axial region so that the compressed volume of lung tissue is disposed at least in part between the surface and the third airway axial region. In some embodiments, the implant comprises a fourth elongate body portion coupled to the third body portion so as to urge a fourth airway axial region toward the first, second, and third airway axial regions when the implant is in the second configuration. The compressed lung tissue volume is disposed therebetween, with some or all of the remaining tissue of the lung thereby gaining therapeutically beneficial tension.

The compressed volume of lung tissue may be sufficiently large and may be compressed sufficiently to increase tension in an uncompressed volume of the lung such that lung function of the lung is increased.

Embodiments of the lung volume reduction system can be adapted to provide an implant that is constrained in a first configuration to a relatively straighter delivery configuration and allowed to recover in situ to a second configuration that is less straight configuration. Devices and implants can be made, at least partially, of spring material that will fully recover after having been strained at least 1%, suitable material includes a metal, such as metals comprising Nickel and Titanium. In some embodiments, the implant of the lung volume reduction system is cooled below body temperature in the delivered configuration. In such an embodiment, the cooling system can be controlled by a temperature sensing feedback loop and a feedback signal can be provided by a temperature transducer in the system. The device can be configured to have an Af temperature adjusted to 37 degrees Celsius or colder. Additionally, at least a portion of the metal of the device can be transformed to the martensite phase in the delivery configuration and/or can be in an austenite phase condition in the deployed configuration.

In another embodiment of the invention, a lung volume reduction system comprising an implantable device that is configured to be deliverable into a patient's lung and configured to be reshaped to make the lung tissue that is in contact with the device more curved. In some embodiments, The device is configured to be reshaped to a permanent second configuration. Additionally, or alternatively, the device can be adapted and configured to have a first shape and is configured to be strained elastically to a deliverable shape. Additionally, in some embodiments, the implantable device has a first shape and is adapted to be elastically constrained by a delivery device to a deliverable configuration whereby removal of the delivery device allows the implant to recoil and be reshaped closer to its first shape. In still other embodiments, the tissue that is in contact with the device is that of blood vessel, airway, lung dissection fissure or a combination of these. The delivered device can be reshaped into a shape that is shorter in length than the deliverable implant configuration. Additionally, the implant can be adapted and configured to provide a distal end and a proximal end and the distance between the two ends is reduced when the implant is reshaped. Further, the implant can be configured to occupy less than the entire lumen cross section area of a lung airway; less than the entire lumen cross section area of a blood vessel; and/or have a deliverable shape that fits within a cylindrical space that is 18 mm in diameter or smaller. In some embodiments, the surface area of the implant that comes into contact with tissue is larger than 0.000001 or 1.0-6 square inches per linear inch of length of the implant. In other embodiments, the implant is coated with material that reduces the rate of wound healing, tissue remodeling, inflammation, generation of granular tissue or a combination of these. In still other embodiments, the reshaped implant is adapted and configured to lie within a single plane. Additionally, the reshaped implant can take on a variety of shapes, including, for example, the shape of a C, the shape of an S, or any other suitable shape. In still other embodiments, the reshaped implant is adapted and configured to lie within more than a single plane. In multi-planar embodiments, the reshaped implant is adapted and configured to take on a variety of shapes, including, for example, the shape of a baseball seam, or the shape of a coil. In some embodiments, the reshaped implant has more than one radius of curvature. Additionally, systems are provided wherein more than one implant is delivered and reshaped. In such systems, the devices can be delivered to separate locations. Alternatively, the devices can be coupled, either before or after delivery. Additionally, the implants can be deployed to partially occupy a common region in the lung. In still further embodiments, the lung volume reduction system can provide implantable devices made of a resiliently bendable material. The system can further be adapted to comprise an actuator adapted to be operated from outside the patient to reshape the implant. Suitable mechanisms for actuating the device include, catheters. Additionally, the catheter can be further adapted and configured to constrain the implant in a deliverable configuration. In some embodiments, the system further comprises a pusher adapted to deliver the implant into a patient's lung. Additionally, the implant can be adapted and configured to have blunt distal and proximal ends, such as with the use of balls positioned thereon. Additionally, a central wire can be provided that spans the length of the device. A pusher can be provided that is releasably coupled to the device.

In another embodiment, the system provides a recapture device adapted and configured to remove the implant from a patient's lungs. The recapture device can be adapted to couple at an end of the device. Additionally, the recapture device can be configured to operate within a catheter or bronchoscope working channel lumen. A resilient wire can also be provided to guide a delivery catheter. In still other embodiments, the system further comprises a resilient dilator device that fits in the catheter lumen. The dilator device can be further adapted and configured to provide a lumen that accommodates a resilient wire. In at least some embodiments, the lung volume reduction system implant has an arc length that remains constant.

In yet another embodiment of the invention, a lung volume reduction device is provided that comprises an elongate body adapted to be inserted into a lumen adjacent lung tissue, the device having a delivery configuration and a deployed configuration more curved than the delivery configuration. In some embodiments, the elongate body is more rigid in the deployment configuration than in the delivery configuration. In still other embodiments, at least a portion of the elongate body comprises a rigid arc when in the deployment configuration having rigidity greater than that of lung tissue. In some embodiments, the rigid arc extends from a point in a proximal half of the device to a point in the distal half of the device. In still other embodiments, the elongate body comprises a plurality of rigid arcs when in the deployment configuration. The plurality of rigid arcs can also be positioned such that the arcs are not at the proximal or distal ends of the elongate body.

In many embodiments, a lung volume reduction system is provided comprising an implantable device that is configured to be deliverable into a patient's lung and configured to reshape lung tissue while allowing fluid to flow both directions past the implant.

In still another embodiment of the invention, a lung volume reduction system is provided comprising an implantable device that is configured to be deliverable into a patient's lung configured to be reshaped to a shape that is not axi-symmetric to bend lung tissue.

Pursuant to another method of the invention, a method of bending a lung airway of a patient is provided comprising inserting a device into the airway in a delivery configuration and bending the device into a deployed configuration to reduce the radius of curvature of at least a portion the airway.

Still another method of the invention provides a method of bending a lung airway of a patient comprising inserting an implantable device into the airway in a delivery configuration and bending the device into a deployed configuration to reduce the radius of curvature of at least a portion the airway. In an embodiment, the step of bending can further comprise operating an actuator outside the patient, the actuator being operatively connected to the device. In yet another embodiment, the step of bending further comprising locking the device into the deployed configuration. In still another embodiment, the step of bending further comprises unlocking the device to permit it to return to the delivery configuration. Additionally, in some embodiments, the step of bending can further comprise disconnecting the actuator from the device. Suitable devices for the methods of the invention include devices that comprise a plurality of asymmetric segments, inserting comprises delivering the plurality of asymmetric segments to the airway as well as devices comprising shape memory material. Additionally, the step of bending can further comprise rotating at least one asymmetric segment with respect to at least another asymmetric segment. An additional step of some embodiments of the method can further comprise delivering a catheter and delivering a shape memory element through the catheter. After delivery of the device, according to the methods provided, the device can then bend into a substantially C shape, S shape, spiral shape, coil shape of one or more radiuses, as well as any shape that is within one or more planes. In an additional embodiment of the method, the step of inserting further comprises delivering the device through a working channel of a bronchoscope. In yet another step of the method, the method further comprises retrieving the device from the airway. Embodiments of the method can further provide the step of providing strain relief to an end of the device during deployment. The delivery configuration of the device can be achieved by transforming metal to a martensite phase or by cooling the implant, such as by delivering liquids or gas. Cooled liquids or gases can be at delivered at temperatures that are at or below body temperature, are 37 degrees Celsius or lower in temperature, or at or below zero degrees Celsius. In some methods of the invention, the implant and surrounding tissues are cooled below zero degrees Celsius, or at or below minus fifteen degrees Celsius.

In another method of the invention, a method is provided for reducing lung volume in a patient comprising inserting a device into an airway and causing bending of the airway. The method can further include the step of inserting a second device into a second airway; connecting the first and second devices to each other; bending the first device to a the first device to a deployed condition to bend or deform the airway at a first location; and bending the second device to a deployed condition to bend the airway at a second location. Additionally, the method can include connecting two or more devices, such as connecting the devices to a common airway. An additional step of the method can include applying pressure on the junction where the airways join. Still another step of the method can include connecting bending elements that are individually placed into one or more airways. Yet another step can include bending one or more bending elements that are placed in one or more airways. An additional step includes configuring the device to make the airway conform to the shape of the implant in a deployed condition.

The method may further comprise selecting the elongate body from among a plurality of alternative elongate bodies and loading the selected elongate body into the catheter body. The plurality of elongate bodies are allowed to bend toward the bent configuration so as to limit strain of the elongate bodies during storage and prior to the selection. The selected elongate body is loaded into the catheter body by straightening the elongate body toward the axis and inserting the elongate body into the catheter so that the catheter maintains the elongate body in the delivery configuration.

Inserting of the selected elongate body may comprise loading the selected elongate body into a tubular loading cartridge and advancing the elongate body from the loading cartridge into the lumen of the catheter. In certain embodiments, the method can further comprise attaching the loading cartridge to the catheter so that a lumen of the loading cartridge is coaxial with the lumen of the catheter and so that the loading cartridge is axially affixed relative to the catheter. A distal end of the loading cartridge may be affixed to a proximal hub of the catheter so that the lumen of the loading cartridge extends smoothly to the lumen of the catheter. The method may further comprise pushing the elongate body from within the attached loading catheter to within the catheter with a pusher. The pusher effects deployment of the implant from a distal end of the catheter by extending the pusher through the loading cartridge.

The method may further comprise axially restraining the proximal end of the elongate body within the lung and withdrawing the catheter proximally from over the distal end of the elongate body.

In many embodiments, the method further comprises grasping the proximal end of the elongate body using a grasper, determining that the deployment of the implant is less than ideal, and retrieving the implant back into a lumen of the catheter using the grasper. The grasper extends distally within the catheter before deploying the implant. The grasper grasps the implant during and after deployment. Retrieving the implant may comprise tensioning the grasper proximally and pushing the catheter distally so that the catheter straightens the elongate body of the implant axially within the airway so as to facilitate withdrawing the implant axially from the airway system.

In many embodiments, the method further comprises advancing the catheter body using a guidewire extending distally through a lumen of the catheter. A tip of the guidewire angles from an axis of the catheter so as to facilitate steering. The guidewire has a cross-section significantly smaller than a lumen of the catheter. A dilator atraumatically expands openings of the airway system as the catheter advances distally. The dilator tapers radially outward proximally of the guidewire tip between a distal end of the catheter and the tip of the guidewire. The method further comprises withdrawing the dilator proximally from the catheter before deploying the implant.

In many embodiments, the method further comprises deploying the catheter and advancing the catheter body distally under guidance of a remote imaging modality, and without optical imaging of at least a distal portion of the implant during deployment. The method may further comprise advancing the catheter body into the lung using a bronchoscope, advancing a distal end of the catheter distally beyond a viewing field of the bronchoscope, and deploying at least the distal portion of the implant distally beyond the viewing field of the bronchoscope.

In many embodiments, the method further comprises advancing a guidewire distally of the catheter toward a distal end of the airway system, the guidewire having an indicia of lengths to the distal end of the guidewire, and selecting a length of the elongate body using the indicia.

In some embodiments, the elongate body is biased to bend to a bent deployed configuration. The lumen maintains the elongate body in the delivery configuration by restraining the elongate body within the catheter. The system may further comprise a plurality of alternatively selectable implants. Each implant comprises an elongate body and can be released toward the bent configuration so as limit strain of the elongate body during storage. Each implant can be loaded into the catheter by straightening the associated elongate body toward the axis and inserting the elongate body into the lumen so that the catheter maintains the elongate body in the delivery configuration. In certain embodiments, the system may further comprise a tubular loading cartridge having a proximal end and a distal end. The loading cartridge releasably receives a selected elongate body from among the plurality of elongate bodies. The loading cartridge can be coupled to the catheter body so that the selected elongate body is advanceable from within the loading cartridge distally into the lumen of the catheter. A distal end of the loading cartridge may be affixed to a proximal hub of the catheter so that a lumen of the loading cartridge extends smoothly to the lumen of the catheter. And, the system may further comprise a pusher axially movable within the loading cartridge and the catheter so as to push the elongate body from within the attached loading catheter to within the catheter. The pusher has a pusher surface distally engageable against the implant and a shaft extending proximally from the pusher surface to facilitate deployment of the implant from the distal end of the catheter.

In many embodiments, the system further comprises a grasper extending distally along the catheter. The grasper is axially coupled to the implant so as to facilitate retrieving the implant into a lumen of the catheter when the elongate body is distal of the catheter. The grasper is articulatable from the proximal end of the catheter so as release the elongate body. In some embodiments, tensioning the grasper proximally and pushing the catheter distally effects retrieving of the implant when the elongate body is distal of the catheter, the grasper is axially coupled to the grasper, and the catheter straightens the elongate body of the implant axially so as to facilitate withdrawing the implant axially from the airway system.

In many embodiments, the system further comprises a guidewire and a dilator. The guidewire is extendable distally through a lumen of the catheter for advancing the catheter body through the airway system. A steering tip of the guidewire angles from an axis of the catheter. The guidewire has a cross-section significantly smaller than a lumen of the catheter. The dilator is advanceable distally through the lumen of the catheter so that the dilator is disposed axially between the guidewire tip and the distal end of the catheter. The dilator tapers radially outwardly proximally of the guidewire tip to atraumatically expand openings of the airway system as the catheter advances distally. In some embodiments, the system further comprises one or more radiopaque markers positionable adjacent the distal end of the catheter to facilitate positioning of the implant.

In many embodiments, the system further comprises a bronchoscope and an image signal transmitter. The bronchoscope has a proximal end, a distal end, and a lumen therebetween. The distal end of the catheter is receivable into the lumen and advanceable distally beyond a viewing field of the bronchoscope so as to deploy the implant distally beyond the viewing field of the bronchoscope. In some embodiments, the system further comprises a guidewire receivable through a lumen of the catheter when the guidewire extends to a distal end of the airway. The guidewire has indicia of a distal length of the guidewire between the catheter or bronchoscope and a distal end of the guidewire. The indicia may optionally comprise radiopaque scale markings along the distal length of the guidewire.

In another embodiment, the invention provides a method for treating a lung of a patient. The lung including an airway system, and the method comprises deploying an implant into an axial region of the airway having a first end and a second end. The implant is deployed so that a proximal end of the implant engages the first end of the axial region, so that a distal end of the implant engages the second end of the axial region, and so that the implant bends the airway between the first end of the axial region and the second end of the axial region. Optionally, the proximal end of the implant, the distal end of the implant, and the implant between the proximal and distal ends press laterally against the airway so as to compress adjacent lung tissue from within the airway system.

In yet another aspect, the invention provides an implant for treating a lung of a patient. The lung includes an airway system, and the implant comprises an elongate body having a proximal end and a distal end. The implant has an insertion configuration suitable for insertion of the implant into an axial region of the airway so that a proximal end of the implant is adjacent the first end of the axial region and so that a distal end of the implant is adjacent the second end of the axial region, wherein the inserted implant is reconfigurable to a deployed configuration imposing a bend in the airway between the first end of the axial region and the second end of the axial region.

BRIEF DESCRIPTION OF THE DRAWINGS

A better understanding of the features and advantages of the present invention will be obtained by reference to the attached documents that set forth illustrative embodiments, in which the principles of the invention are utilized, and the accompanying drawings of which:

FIGS. 4A-4F illustrate a lung volume reduction device according to an aspect of the invention;

FIGS. 9A-9D illustrate a lung volume reduction device according to another aspect of the invention;

FIGS. 10A-10B illustrate segments suitable for use in configuring a lung volume reduction device according to an aspect of the invention;

FIGS. 15A-15D illustrate a decoupler system;

FIGS. 20A-20E illustrate a hitch pin configuration useful in decoupling the delivery device;

FIGS. 29A-29C illustrate another retrieval mechanism;

FIG. 37 illustrates a device configuration;

FIG. 38 illustrates a device in a loading cartridge;

FIG. 39 illustrates a long device configuration;

FIG. 40 illustrates a device configuration with a wire support frame;

FIG. 41 illustrates a device configuration with a covering;

FIG. 42 illustrates a device configuration with a perforated covering;

DETAILED DESCRIPTION OF THE INVENTION

Figure 1A:
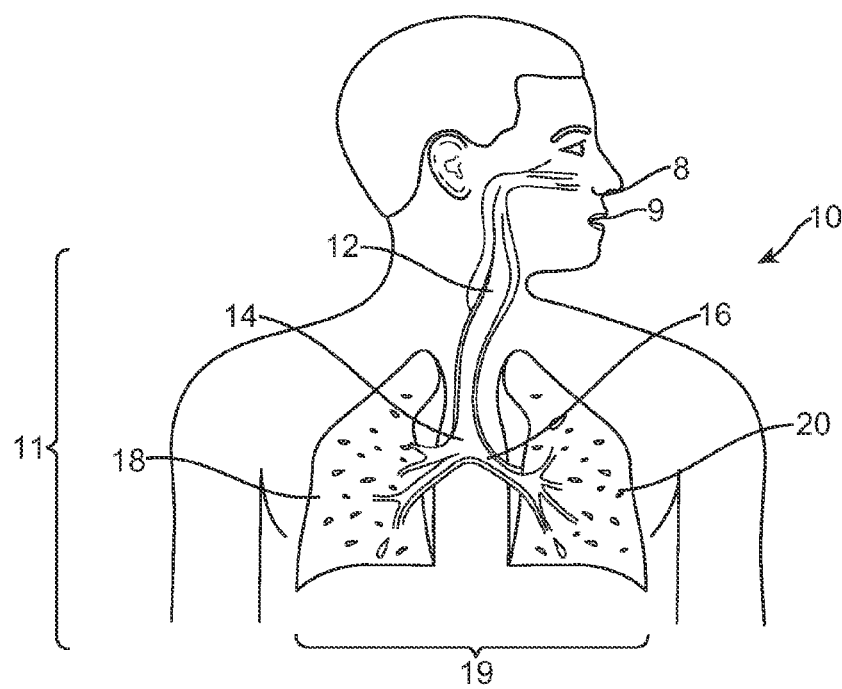
FIGS. 1A-1C illustrates the anatomy of the respiratory system.

By way of background and to provide context for the invention, FIG. 1A illustrates the respiratory system 10 located primarily within a thoracic cavity 11. This description of anatomy and physiology is provided in order to facilitate an understanding of the invention. Persons of skill in the art, will appreciate that the scope and nature of the invention is not limited by the anatomy discussion provided. Further, it will be appreciated there can be variations in anatomical characteristics of an individual, as a result of a variety of factors, which are not described herein. The respiratory system 10 includes the trachea 12, which brings air from the nose 8 or mouth 9 into the right primary bronchus 14 and the left primary bronchus 16. From the right primary bronchus 14 the air enters the right lung 18; from the left primary bronchus 16 the air enters the left lung 20. The right lung 18 and the left lung 20, together comprise the lungs 19. The left lung 20 is comprised of only two lobes while the right lung 18 is comprised of three lobes, in part to provide space for the heart typically located in the left side of the thoracic cavity 11, also referred to as the chest cavity.

Figure 1B:
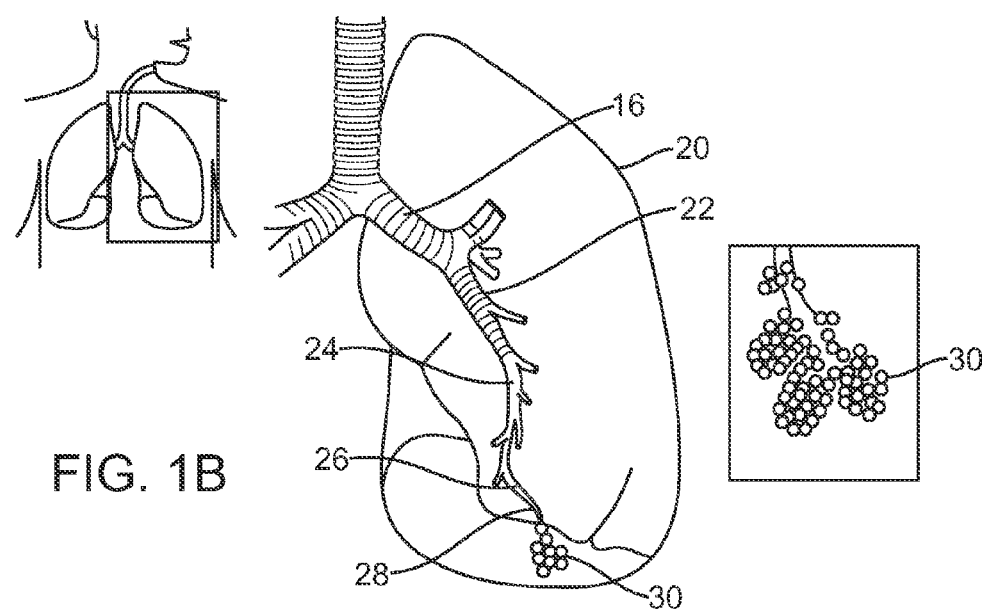
Figure 1C:
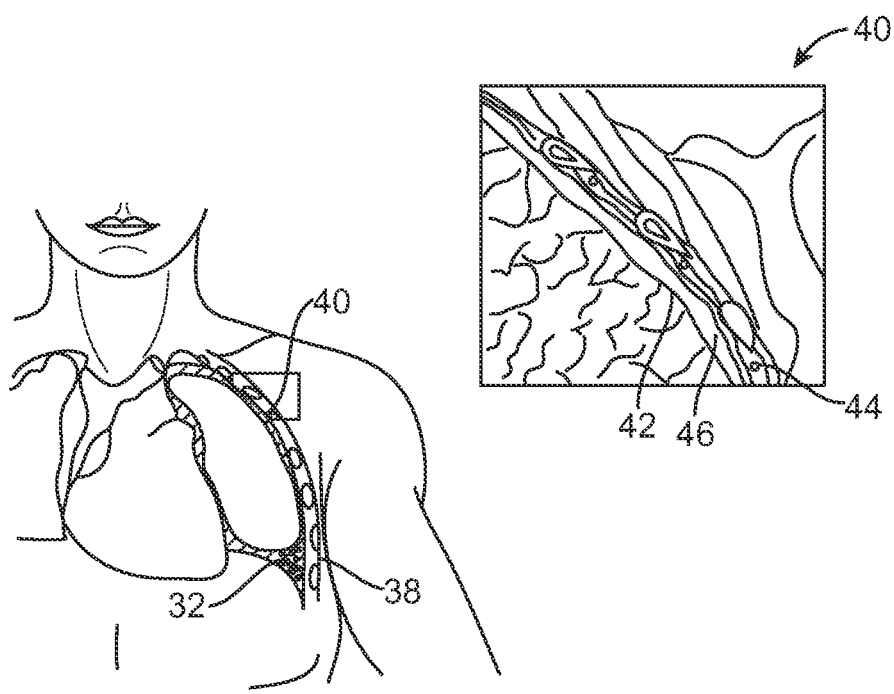
Figure 2A:
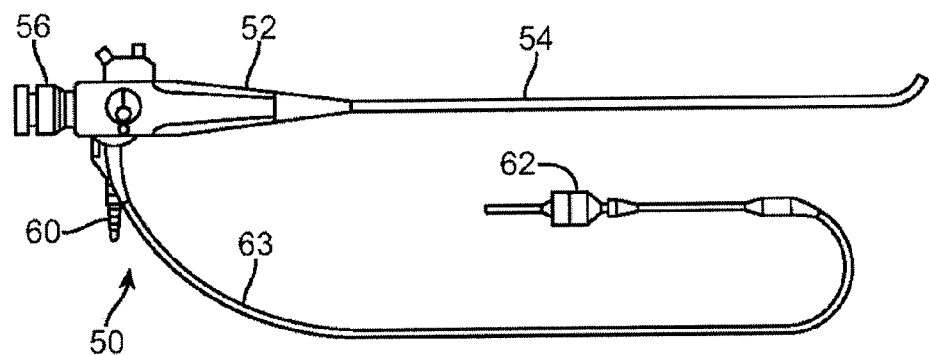
FIGS. 2A-2D illustrate a bronchoscope.
Figure 2B:
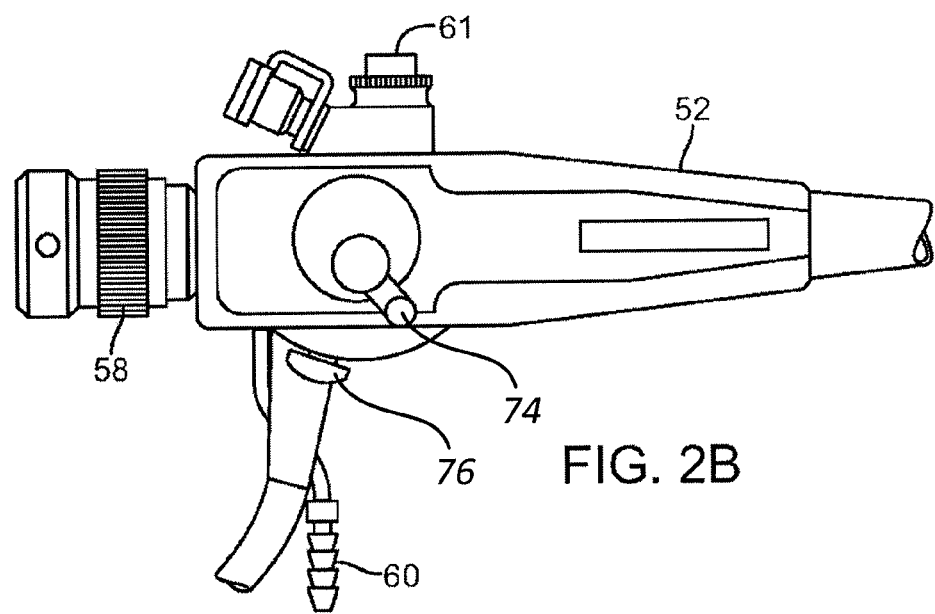
Figure 2C:
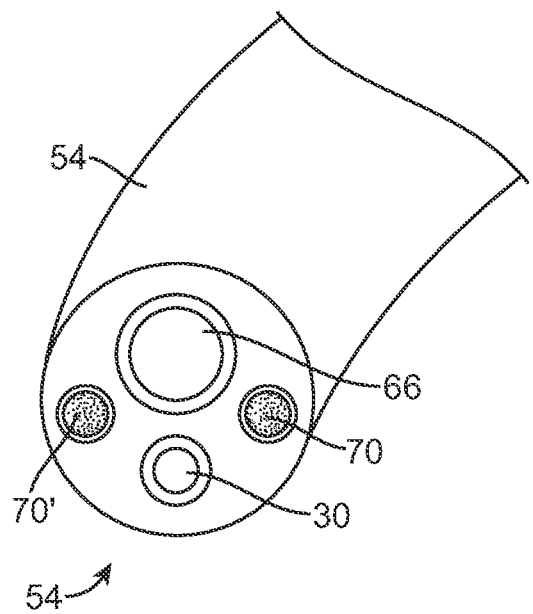
Figure 2D:
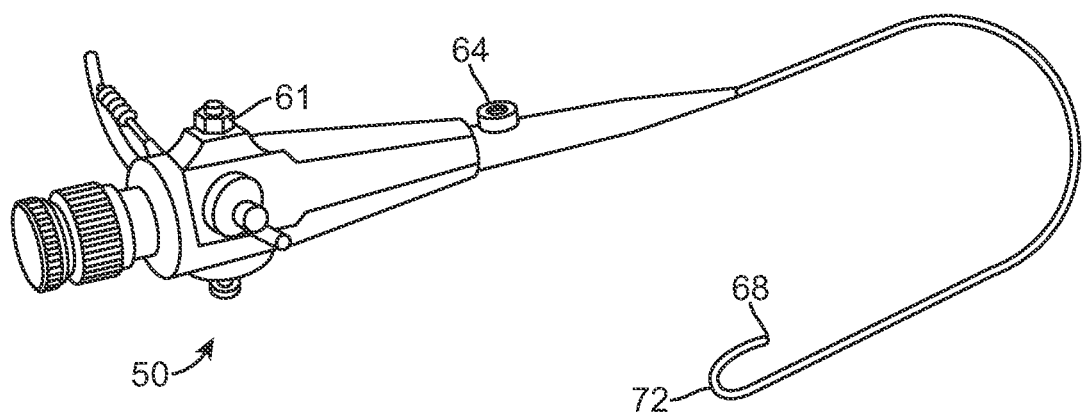

As shown in more detail in FIG. 1B, the primary bronchus, e.g. left primary bronchus 16, that leads into the lung, e.g. left lung 20, branches into secondary bronchus 22, and then further into tertiary bronchus 24, and still further into bronchioles 26, the terminal bronchiole 28 and finally the alveoli 30. The pleural cavity 38 is the space between the lungs and the chest wall. The pleural cavity 38 protects the lungs 19 and allows the lungs to move during breathing. As shown in FIG. 1C, the pleura 40 defines the pleural cavity 38 and consists of two layers, the visceral pleurae 42 and the parietal pleurae 44, with a thin layer of pleural fluid therebetween. The space occupied by the pleural fluid is referred to as the pleural space 46. Each of the two pleurae layers 42, 44, are comprised of very porous mesenchymal serous membranes through which small amounts of interstitial fluid transude continually into the pleural space 46. The total amount of fluid in the pleural space 46 is typically slight. Under normal conditions, excess fluid is typically pumped out of the pleural space 46 by the lymphatic vessels.

The lungs 19 are described in current literature an elastic structure that float within the thoracic cavity 11. The thin layer of pleural fluid that surrounds the lungs 19 lubricates the movement of the lungs within the thoracic cavity 11. Suction of excess fluid from the pleural space 46 into the lymphatic channels maintains a slight suction between the visceral pleural surface of the lung pleura 42 and the parietal pleural surface of the thoracic cavity 44. This slight suction creates a negative pressure that keeps the lungs 19 inflated and floating within the thoracic cavity 11. Without the negative pressure, the lungs 19 collapse like a balloon and expel air through the trachea 12. Thus, the natural process of breathing out is almost entirely passive because of the elastic recoil of the lungs 19 and chest cage structures. As a result of this physiological arrangement, when the pleura 42, 44 is breached, the negative pressure that keeps the lungs 19 in a suspended condition disappears and the lungs 19 collapse from the elastic recoil effect.

When fully expanded, the lungs 19 completely fill the pleural cavity 38 and the parietal pleurae 44 and visceral pleurae 42 come into contact. During the process of expansion and contraction with the inhaling and exhaling of air, the lungs 19 slide back and forth within the pleural cavity 38. The movement within the pleural cavity 38 is facilitated by the thin layer of mucoid fluid that lies in the pleural space 46 between the parietal pleurae 44 and visceral pleurae 42. As discussed above, when the air sacs in the lungs are damaged 32, such as is the case with emphysema, it is hard to breathe. Thus, isolating the damaged air sacs to improve the elastic structure of the lung improves breathing.

A conventional flexible bronchoscope is described in U.S. Pat. No. 4,880,015 to Nierman for Biopsy Forceps. As shown in FIGS. 2A-D, bronchoscope 50 can be configured to be of any suitable length, for example, measuring 790 mm in length. The bronchoscope 50 can further be configured from two main parts, a working head 52 and an insertion tube 54. The working head 52 contains an eyepiece 56; an ocular lens with a diopter adjusting ring 58; attachments for the suction tubing 60 and a suction valve 61 and for the cold halogen light source 62 and 63; and an access port or biopsy inlet 64, through which various devices and fluids can be passed into the working channel 66 and out the distal end of the bronchoscope. The working head is attached to the insertion tube, which typically measures 580 mm in length and 6.3 mm in diameter. The insertion tube can be configured to contain fiberoptic bundles (which terminate in the objective lens 30 at the distal tip 68), two light guides 70, 70' and the working channel 66. The distal end of the bronchoscope has the ability to bend 72 anterior and posterior only, with the exact angle of deflection depending on the instrument used. A common range of bending is from 160 degrees forward to 90 degrees backward, for a total of 250 degrees. Bending is controlled by the operator by adjusting an angle lock lever 74 and angulation lever 76 on the working head. See also, U.S. Patent Pub. US 2005/0288550 A1 to Mathis for Lung Access Device and US 2005/0288549 A1 to Mathis for Guided Access to Lung Tissue.

Figure 3:
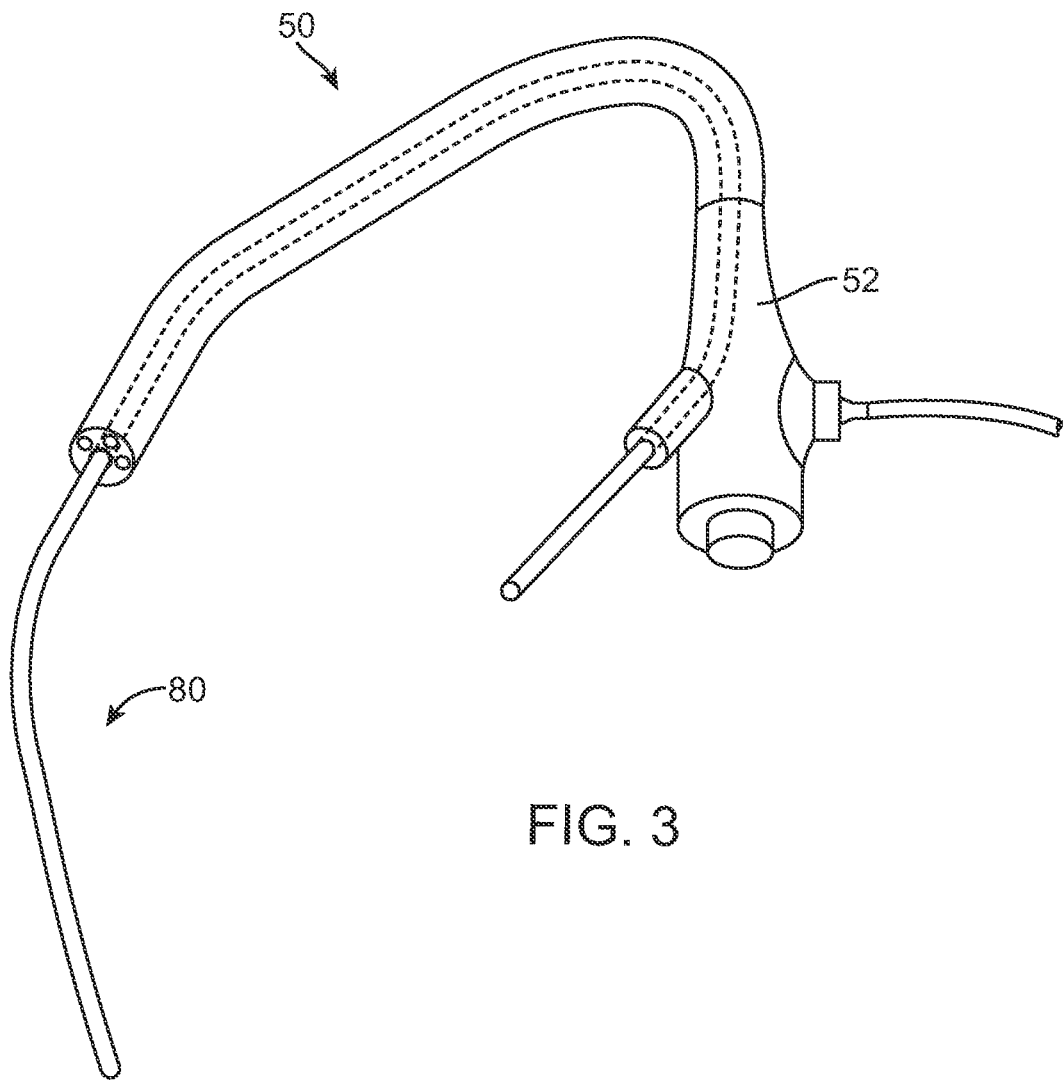
FIG. 3 illustrates a bronchoscope in combination with a delivery device for a lung volume reduction device according to the invention.

FIG. 3 illustrates the use of a lung volume reduction delivery device 80 for delivering a lung volume reduction device comprising an implantable device with the bronchoscope SO. The lung volume reduction system, as described in further detail below, is adapted and configured to be delivered to a lung airway of a patient in a delivered configuration and then changed to a deployed configuration. By deploying the device, tension can be applied to the surrounding tissue which can facilitate restoration of the elastic recoil of the lung. The device is designed to be used by an interventionalist or surgeon.

FIGS. 4A-F illustrate a lung volume reduction device 110 according to an aspect of the invention, with FIGS. 4B-F being cross-sections taken along the lines B-B, C-C, D-D, E-E and F-F of FIG. 4A, respectively. The lung volume reduction device 110 includes a member, such as tubular member 112, which has c-cuts 114, or notches, along its length to provide flexibility such that the device can be deflected off a longitudinal axis A when deployed. For example, where the cuts are oriented parallel each other along the length of the tubular member and are of the same or similar depth D, the device will tend to uniformly curve around an axis point when deployed (depicted below). As a result, the device preferentially curls or bends in a direction as determined by the shape of the slots. Different types (width, depth, orientation, etc.) of notches or slots can be used to achieve different operational effects and configurations of the deployed device without departing from the scope of the invention.

Positioned within a lumen 113 of the tubular member 112 is an actuation element .116 or pull-wire. The actuation element can have a circular circumference in cross-section, as depicted, or can have any other suitable cross-section. The actuation element 116 is anchored at one end of the device 110, e.g. the distal end, by a cap 119. The cap 119 can be bonded to the catheter and a distal crimp can be provided to crimp the cap into the pull wire. The rounded cap can also be provided to make the tip of the device atraumatic. The opposing end, e.g. proximal end, is adapted and configured to engage a mechanism 120. The mechanism enables the device to be deployed. The mechanism can further be adapted and configured to enable the device to lock into a deployed configuration once the device 110 is deployed or unlocked to retrieve the device. The device 110 is configured to be detachable from a delivery catheter adapted to deliver the lung volume reduction device (discussed below).

Mechanism 120, at the proximal end of the device, can be adapted to include a retainer ring 122 that engages a ratchet 124 that can be used to lock the device in place. The coupler 126 retains the ratchet 124 such that the ratchet locks the device in place once deployed. At the proximal end a retrieval adapter 130 is provided, such as a pull-wire eyelid. The retrieval adapter 130 is adapted and configured to enable the device to be retrieved at a later point during the procedure or during a subsequent procedure. The ratchet device has flanges that extend away from a central axis when deployed to lock the device in place.

Figure 5A:
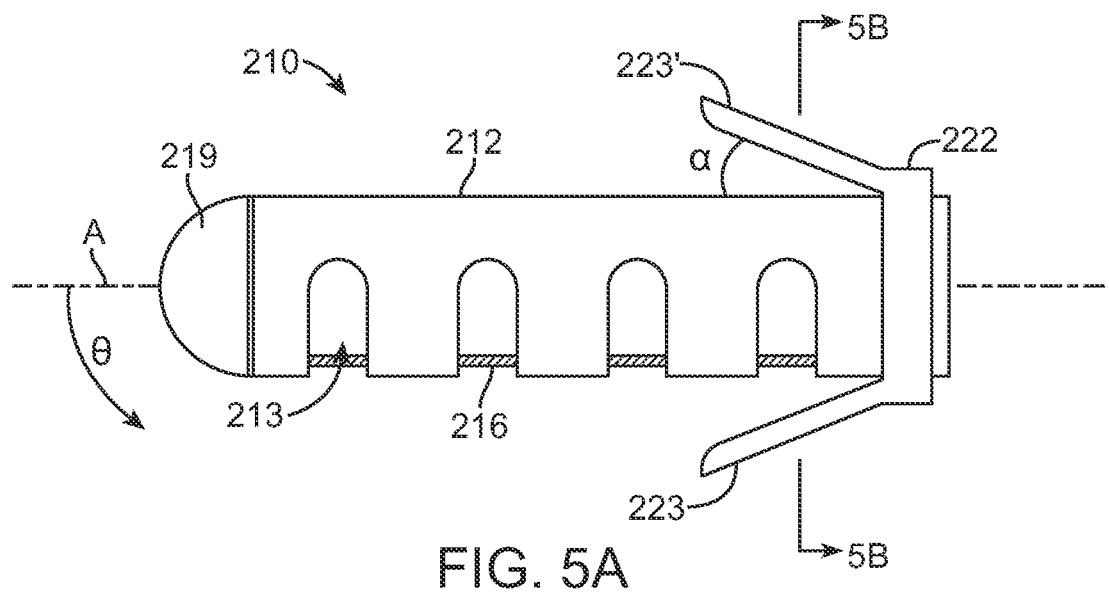
FIGS. 5A-5B illustrate a lung volume reduction device according to another aspect of the invention.
Figure 5B:
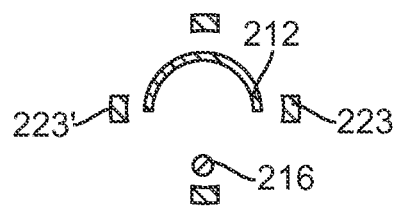

Turning to FIGS. 5A-B, a lung volume reduction device 210 according to another aspect of the invention is depicted, with FIG. 5B being a cross-section taken along the lines B-B of FIG. 5A. Positioned within a lumen 213 of the tubular member 212 is an actuation element 216 or pull-wire. As described above, the actuation element can have a circular circumference in cross-section, as depicted, or can have any other suitable cross-section. The actuation element 216 is anchored at one end of the device 210, e.g. the distal end, by a cap 219. In this embodiment, the retainer ring 222 is configured to provide anchors 223, 223' or teeth that are adapted to deploy by retracting the retaining sheath of a delivery catheter. When deployed, the anchors 223 contact the airway and affix the device in place. The anchor 223 can be configured to be self-expanding such that the anchors extend away from a central axis A of the device 210 when deployed until the anchors approach or extend through (e.g., hook) the airway. The amount of expansion of the anchors will be controlled by the design and the materials used. For example, where a shape memory material is used, the anchors can be configured to extend away from the longitudinal wall of the tubular member by a predetermined angle $\alpha$, as depicted ~10 degrees. The design of the anchor can further be driven by the length of the device. The anchors can be configured to catch on the airway when deployed in a manner similar to the way a stent catches within the vasculature, or the anchor can be designed to cause friction. Prior to deployment, the anchors are retrained by a retaining sheath (illustrated below.).

Figure 6A:
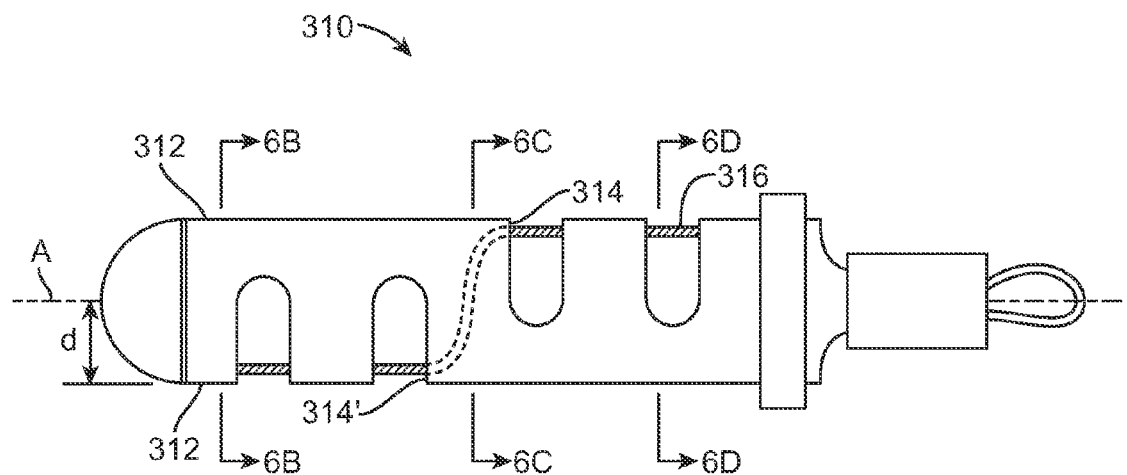
FIGS. 6A-6D illustrate a lung volume reduction device according to another aspect of the invention.
Figure 6B:
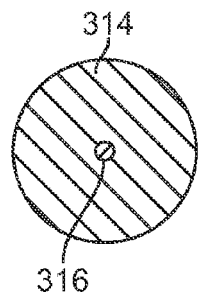
Figure 6C:
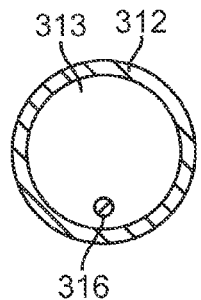
Figure 6D:
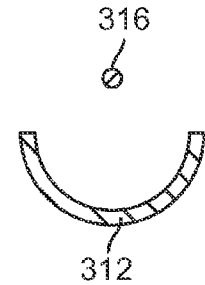

FIGS. 6A-C illustrate yet another lung volume reduction device according to another aspect of the invention, with FIGS. 6B-C being cross-sections taken along the lines B-B, and C-C of FIG. 6A, respectively. As depicted in this embodiment, the lung volume reduction device 310 includes a member, such as tubular member 312, which has c-cuts 314, 314', or notches, along its length to provide flexibility such that the device can be deflected in more than one direction off a longitudinal axis A when deployed. In this embodiment, the notches are positioned on the member 312 on opposing sides of the member when the member is lying within a plane. For example, where the cuts are oriented parallel each other along the length of the tubular member and are of the same or similar depth D, the device will tend to uniformly curve around an axis point when deployed. In this embodiment, when deployed, the configuration of the notches would result in a deployed configuration that is "s"-shaped when the actuator element 316 is pulled proximally (i.e., toward the user).

Figure 7:
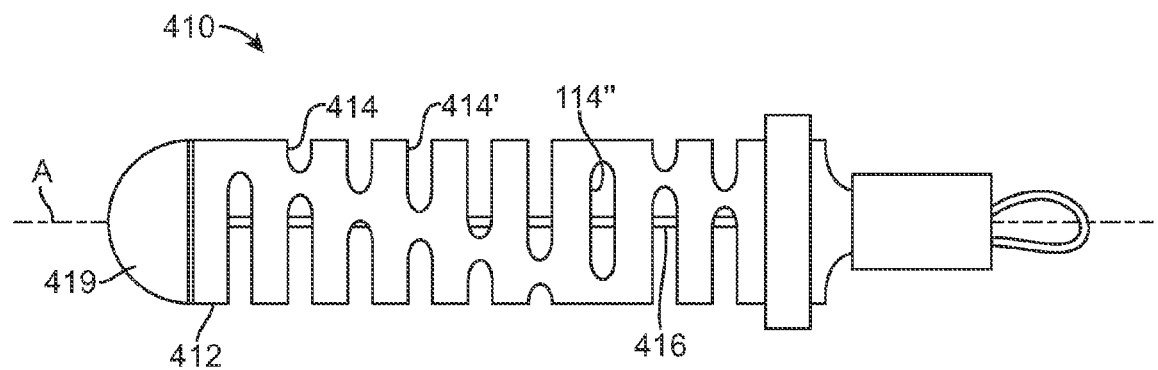
FIG. 7 illustrates a lung volume reduction device according to another aspect of the invention.

FIG. 7 illustrates yet another lung volume reduction device 410 according to another aspect of the invention. In this embodiment, the tubular member 412 has notches 414, 414', 414" configured in a spiral pattern along its length. As a result, when the actuation element 416 is pulled proximally toward the user, the device bends to form a spiral as illustrated below.

Figure 8:
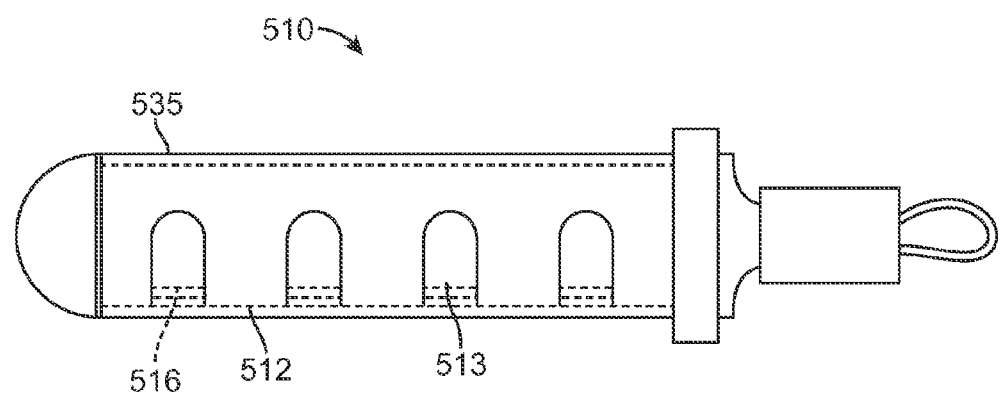
FIG. 8 illustrates a lung volume reduction device encased in a sheath.

FIG. 8 illustrates a lung volume reduction device 510 encased in a sheath 535. The sheath can be a polymeric elastic membrane, such as silicone. The sheath can prevent material from a body cavity from entering the lumen 513 of the tubular member 512. An actuation member 516 is provided within the lumen 513 of the tubular member 512.

FIGS. 9A-D illustrate yet another lung volume reduction device 610 according to another aspect of the invention, with FIGS. 9B-D being cross-sections taken along the lines B-B, C-C, and D-D of FIG. 9A, respectively. The lung volume reduction device 610 in this embodiment is comprised of individual segments 612, 612', 612". The segments can be configured, for example, to have identical asymmetrical configurations such that a compressible space 614 is between each segment before the device is actuated by activating the actuator element 616. Each of the segments can further comprise a detent on a first surface which opposes a mating indentation on a surface of an opposing segment. As will be appreciated, a variety of components of devices disclosed herein can be configured to provide locking or mating mechanisms to facilitate actuation and operation. When the actuation element 616 is activated, the compressible space is reduced and the opposing surfaces of two adjacent segments come together to reduce or eliminate the space between them, depending upon the desired outcome. Where the segments have identical or nearly identical configurations, the device will evenly arc around an axis point. Where the segments do not have identical configurations, a variety of configurations can be achieved upon deployment depending on the configurations of the segments selected and the organization of the segments in the device. As with previous embodiments, the actuator element 616 is secured at one end, e.g., the distal end, by a cap 619. The segments can be formed as hypotubes or can be formed as injection molded or solid pieces. Use of segments can avoid fatigue on the device because the surfaces come in contact with one another during compression. Material selection can also prevent biometallic corrosion. Further, the segment design is conducive for mass production and maintenance of consistence for final shape and operation.

FIGS. 10A-B illustrate segments 712, 712' suitable for use in configuring a lung volume reduction device according to an aspect of the invention. The segments, as depicted, can be generally cylindrical with a pair of surfaces that are either parallel or non-parallel each other at either end. To achieve the operation described above, a first surface 713 could be perpendicular to the elongated tubular sides 715 of the element, while the opposing surface 717 is not perpendicular to the sides of the element (or parallel to the opposing first surface). A detent 721 can be provided on one surface that is configured to mate with an indentation 723 the second surface of another. Other configurations, such as a key: keyway combination, can be used without departing from the scope of the invention. A central lumen 725 is provided through which an actuator element (described above) passes through.

Figure 11A:
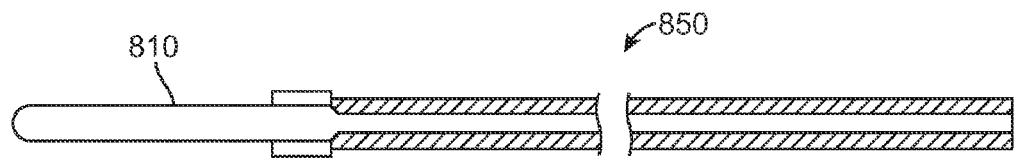
FIGS. 11A-11F illustrate a plurality of individual wires formed of shape memory material that can be deployed to form a lung volume reduction device and a delivery device.
Figure 11B:
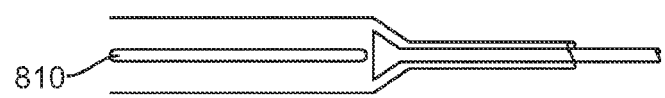
Figure 11C:
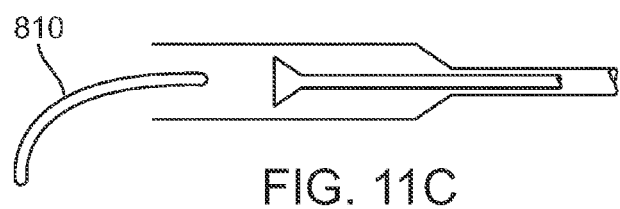
Figure 11D:
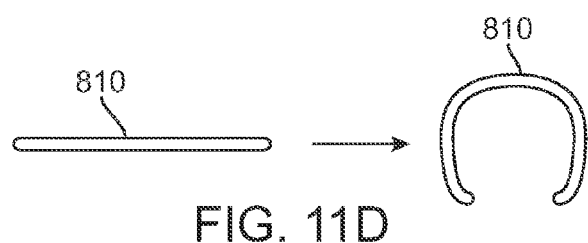
Figure 11E:
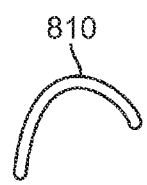
Figure 11F:
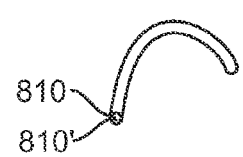

In another embodiment of the invention, as illustrated in FIGS. 11A-F, the device 810 is comprised of a plurality of individual wires formed of shape memory material that resume their shape when implanted. The wires can be heat treated to assume a specific shape, such as a C shape as described above. The wires are then individually implanted through a delivery system 850 such that when the first wire is implanted the diameter of the wire may be small enough that the wire cannot overcome the force applied by the surrounding tissue to assume its preconfigured shape. However, upon implantation of additional wires, the amount of strength available cumulatively among the wires does overcome the force applied by the tissue and the wires, together, achieve the desired shape (see. FIG. 11F). As will be apparent to those of skill in the art, the strength of a shaped wire can vary depending on how much material is used. For example, a shaped wire with a larger cross-section will have higher strength than a shaped wire with a smaller cross-section. However, a larger diameter wire may be harder to implant because it would be harder to straighten into a shape suitable for deployment. Where many small wires are used, each wire individually is more flexible and can be deployed easier, but as a larger number of wires are implanted the combined strength increases. In some embodiments, it may be useful to configure the devices 810 such that the use of, for example, 50-100 wires will have the strength to overcome pressure applied by the tissue. The wires 810 can be deployed within a flexible polymer tube to keep the wires in proximity to each other.

Figure 12:
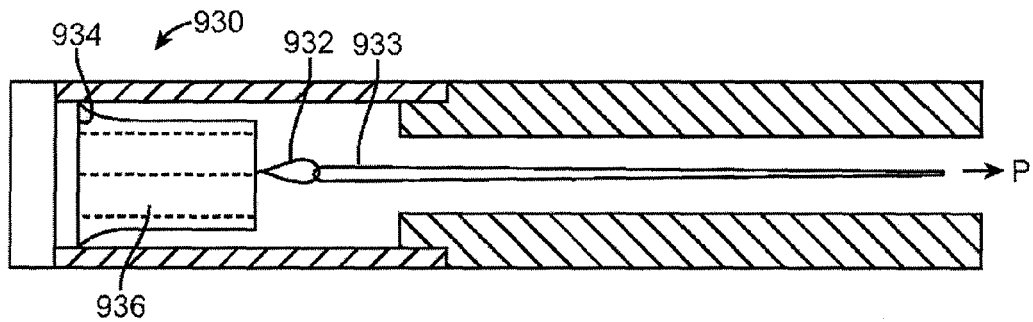
FIG. 12 illustrates a lock feature suitable for use at a proximal end of a lung volume reduction device.
Figure 13A:
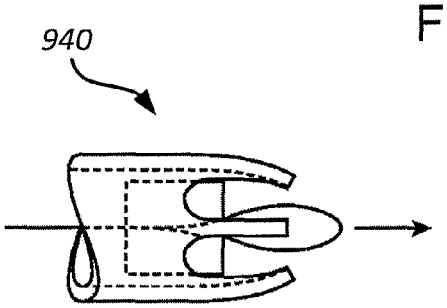
FIGS. 13A-13B illustrate a stopper adapted to hold tension on a lung volume reduction device.
Figure 13B:
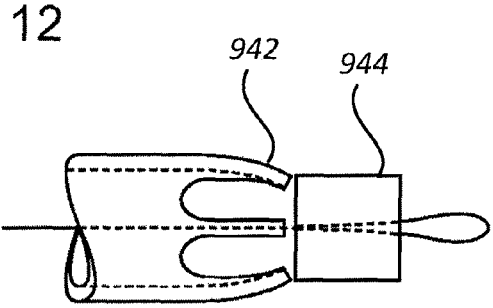

FIG. 12 illustrates a lock feature positioned at the proximal end of a lung volume reduction device such as those discussed above. The lock feature enables the deployed device to retain tension on the actuation element (e.g. 116) when the device is deployed. The lock mechanism 930 has an eyelid 932 which is adapted to engage a pull string 933. The lock feature normally rests on the inside of the implant and pops open to engage the tabs 934 when the ratchet 936 moves proximally P relative to the slotted tube. A stopper 940 can also be employed in the lung volume reduction devices. A stopper is depicted in FIG. 13. The stopper is adapted to hold the tension on the deployed device. Once the actuation element has been engaged and the desired amount of tension is applied which results in a desired shape of the device, the stopper can be deployed to maintain the tension on the device. The stopper can be configured as depicted with a slotted tube forming flanges 942 adapted to fit within a cap 944. Each of the flanges can be formed of shape memory material such that the flanges will tend to extend away from a central axis A to engage the interior surface of the cap 944.

Figure 14A:
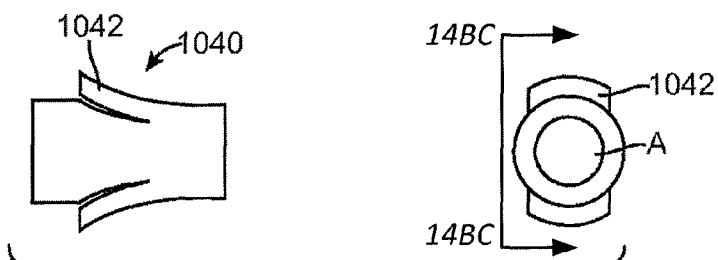
FIGS. 14A-14C illustrates a self locking mechanism suitable for use with the lung volume reduction devices of the invention.
Figure 14B:
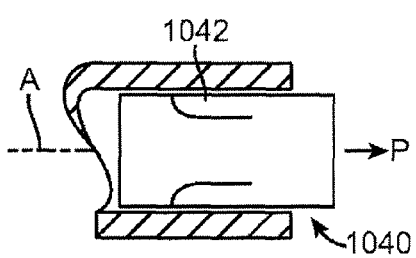
Figure 14C:
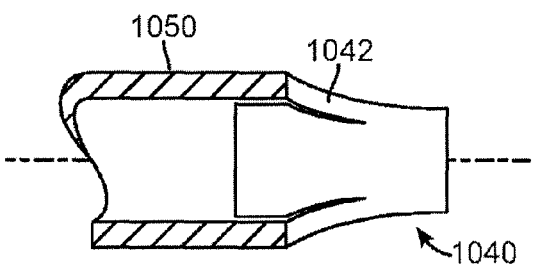

Turning now to FIGS. 14A-C, a self-locking mechanism 1040 suitable for the proximal end of a lung volume reduction device of the invention is depicted, with FIGS. 14B-C being cross-sections taken along line 14BC-14BC of FIG. 14A. One or more flanges 1042 are provided. The flanges 1042 can be configured such that the flanges deflect away from a central axis A when not constrained. Thus, as shown in FIGS. 14B-C, the flanges 1042 are positioned to engage the sides of the self locking mechanism 1040. The flanges can be configured such that they form cut-outs that extend from the device, or can be integrally formed such that the self-locking mechanism still forms a solid tube when the flanges are deployed. FIG. 14C depicts the deployed flanges withdrawn from a retaining tube 1050 of the implant. The interference between the end of the flange and the sides of the retaining tube can be used to prevent, for example, the tap or ratchet from going back into the implant.

The component depicted in FIGS. 15A-C is a ratchet design used to hold the device in place until the delivery device, e.g. catheter, is decoupled. The device is configured to provide a ratchet mechanism having a ratchet wheel and pawl within the interior surface of the proximal end of the device. A retaining sheath 1152 is provided to hold the ratchet mechanism and prevent it from opening up. The sheath is retracted and then the pull wire 1116 is pulled out. Flanges or tabs 1142 are provided that extend away from a central axis when not constrained. A pin 1154 can be provided that slides within a slot 1156 in the tube 1155 and is engaged at a widened aperture 1156. When withdrawing the pull wire 1116 the sides of the ratchet can deform away from the central axis A as shown in FIG. 15C to allow the pull wire to exit. The ratchet tube 1158 can be formed of shape memory material, such as nitinol which can heat set the ratchet to open once the sheath 1152 is removed. Alternatively, the ratchet tube can be formed from stainless steel. Use of stainless steel would require the pull wire with the peg to be pulled out. FIG. 15D is a cross-section taken along the lines D-D of FIG. 15A.

Figure 16A:
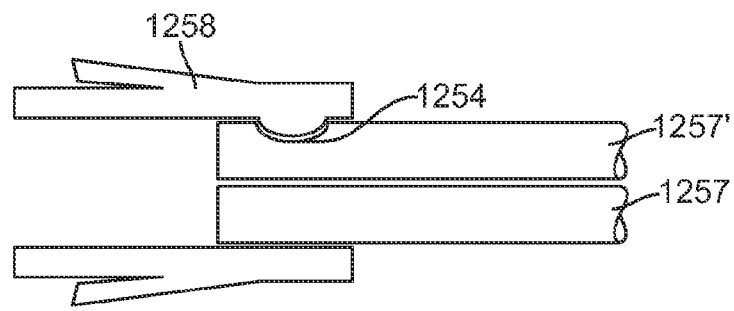
FIGS. 16A-16C illustrates a decoupling system.
Figure 16B:
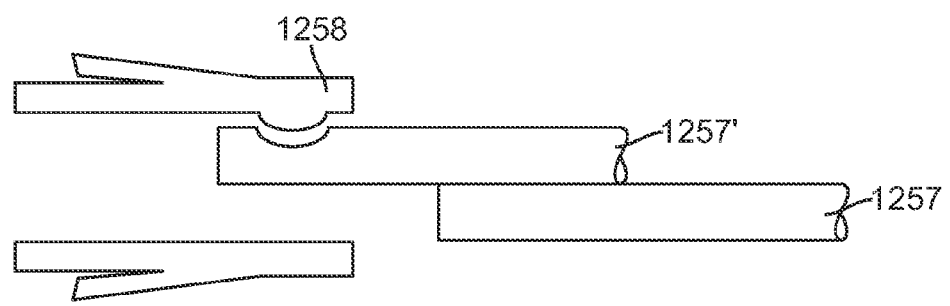
Figure 16C:
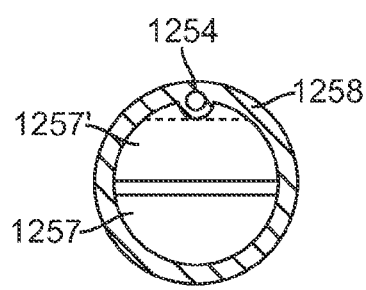

FIGS. 16A-C illustrate yet another mechanism suitable for use with the implantable devices of the invention, wherein a detent 1254 positioned on the inner surface of the ratchet tube 1258. Two tubes 1257,1257' are used to lock the device in place. Once the first tube 1257 is pulled out, the second tube 1257' can deflect away from the detent 1254, thereby unlocking the coupling. The detent 1254 can be configured in the shape of a ball as depicted in the cross-section shown in FIG. 16C. This system can be used to de-couple the delivery device.

Figure 17A:
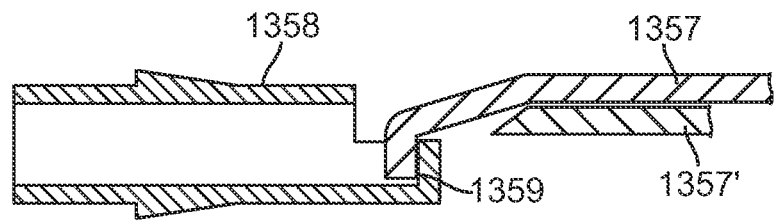
FIGS. 17A-17B depict a mechanism for decoupling the delivery device from a lung volume reduction device.
Figure 17B:
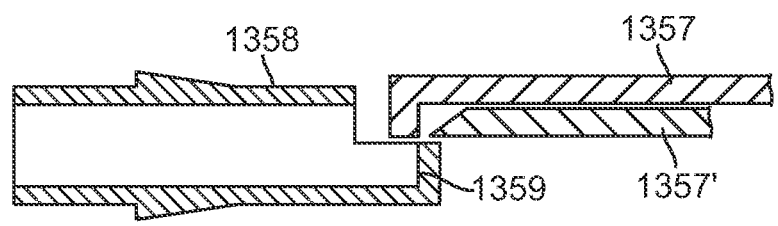
Figure 18:
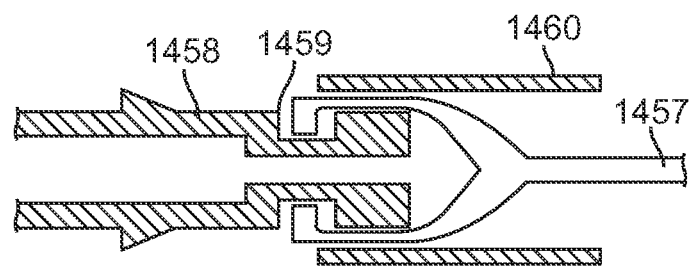
FIG. 18 illustrates another mechanism suitable for use in decoupling the delivery device from a lung volume reduction device.
Figure 19A:
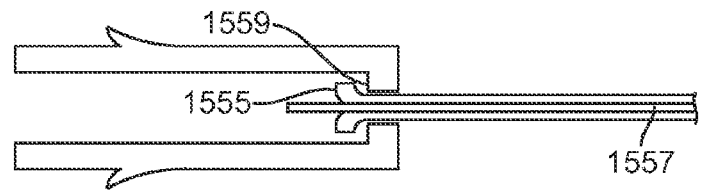
FIGS. 19A-19B illustrate yet another embodiment of a decoupling system.
Figure 19B:
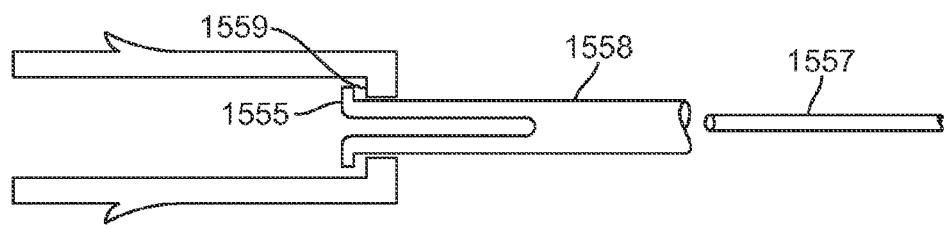
Figure 20A:
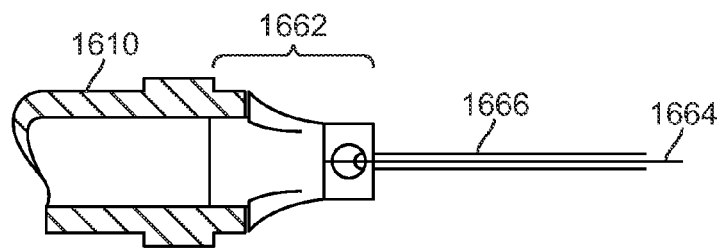
Figure 20B:
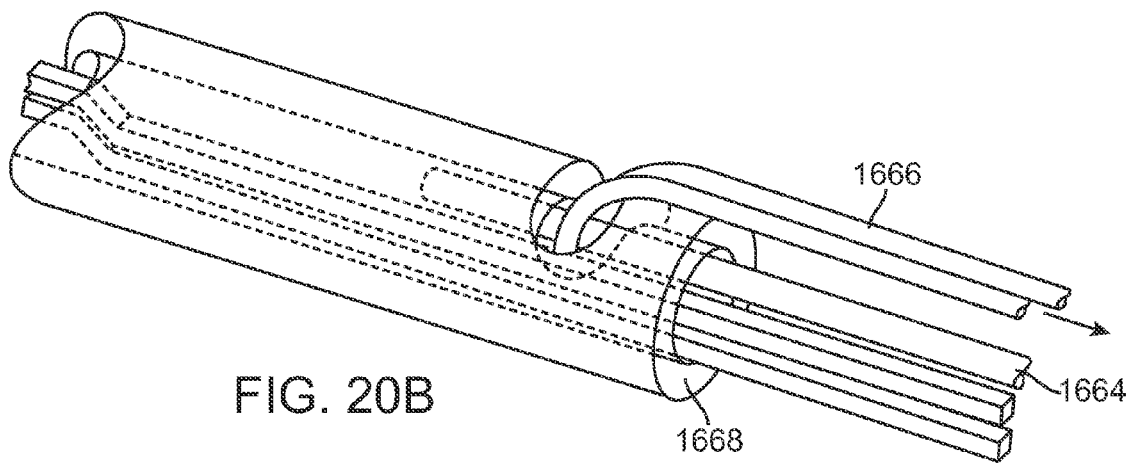

FIGS. 17A-B and 18 depict alternative mechanisms for de-coupling the delivery device. As depicted in FIGS. 17A-B, a push bar 1357' is used to push back a latch bar 1357. The latch bar is adapted to engage a lip on the interior of the device, the push bar deflects the latch bar away from the lip 1359 and enables the bar to be withdrawn as shown in FIG. 17B. In FIG. 18, a retaining sheath 1460 is employed which, when withdrawn in the proximal direction, enables the arms of the latch device 1458 to deflect away from a central axis A, and disengage from a retaining lip 1459. FIGS. 19A-B illustrates yet another embodiment. In the embodiment illustrated, a central pin 1557 is withdrawn which allows the claws 1555 to relax and withdraw away (toward a central axis) from retaining lip 1559 of latch bar 1558.

FIGS. 20A-E illustrates a hitch pin configuration useful for use in actuating and decoupling the delivery device. A portion of the lung volume reduction device 1610 is depicted with an actuation element 1616 positioned therein. A locking mechanism 1640 such as depicted in FIG. 14 engages the proximal end of the device 1610. A hitch pin de-coupling system 1662 is attached to the locking mechanism 1640. Alternatively, the hitch pin can be adapted to decouple from the ratchet mechanism. The hitch pin system 1662 has a hitch pin wire 1664 that engages a hitch pin 1666 loop wire. When the hitch pin wire is inserted it maintains the hitch pin in contact with the locking shaft 1668.

Figure 21:
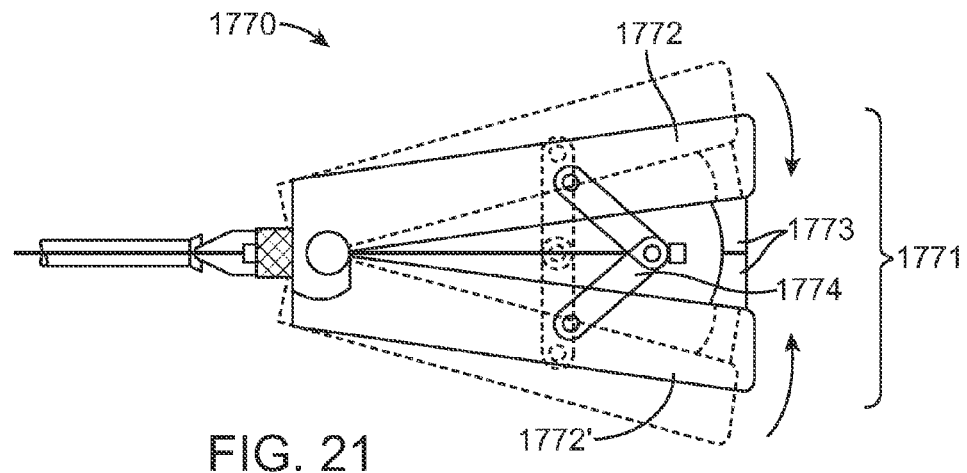
FIG. 21 illustrates an activation mechanism suitable for use with the devices of the invention.
Figure 22:
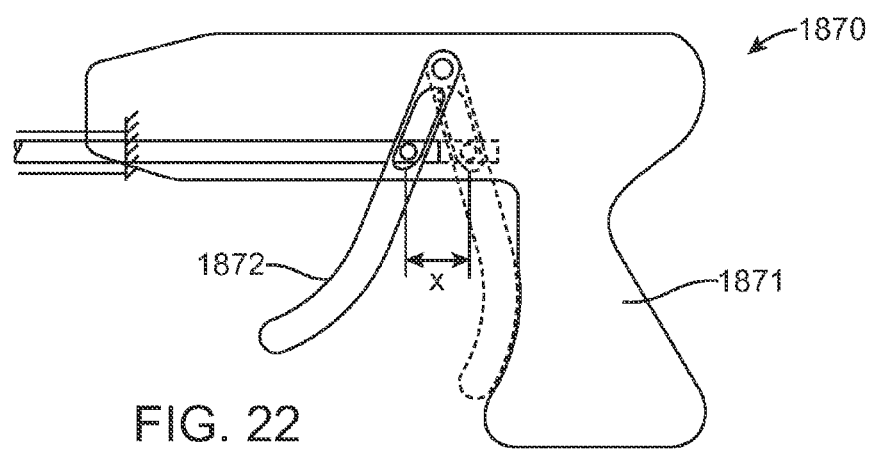
FIG. 22 illustrates an alternative mechanism for proximally controlling the deployment of the device.
Figure 23:
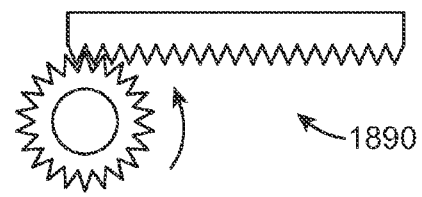
FIG. 23 illustrates a spur gear suitable for use with control mechanisms of the invention.

FIG. 21 illustrates an activation mechanism suitable for use with the invention. The activation mechanism 1770 has a handle 1771 which a user can squeeze to activate the device. Two levers 1772, 1772' of the handle will be advanced toward each other as the user squeezes the levers together. Stoppers 1773 can be provided to control or pre-set the amount of pulling the activation mechanism can achieve in a single squeeze. The amount of displacement of wire at the distal end is indicated by the displacement x from a vertical axis that occurs of hinged lever 1774 positioned between the two levers of the activation mechanism when the user squeezes the levers together. FIG. 22 illustrates an alternative mechanism for proximally controlling the deployment of the device. As illustrated in FIG. 22 a pistol actuator 1870 is provided that has a trigger 1872 which can be pulled back toward a handle 1871. The amount of displacement of the wire can be controlled by the distance x that the trigger is pulled toward the handle. A linear actuation motion can also be simulated by using spur gears 1890 having teeth machined parallel to its axis, such as that shown in FIG. 23.

Figure 24:
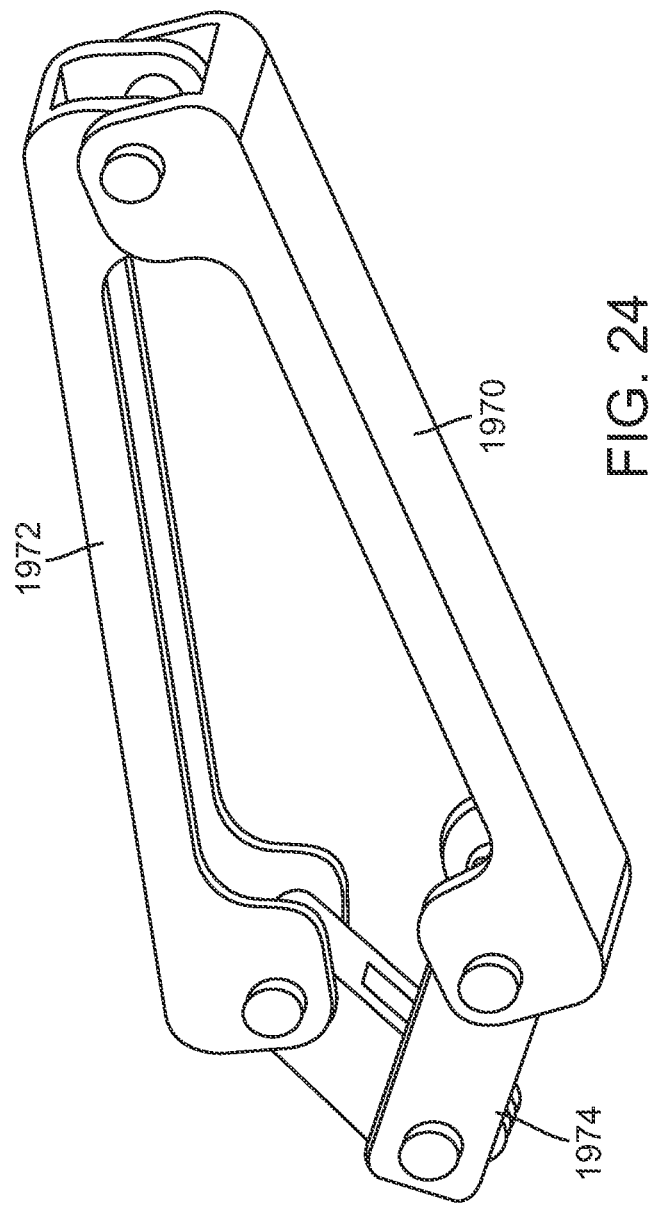
FIG. 24 illustrates a proximal control device for actuating an implant.

FIG. 24 illustrates another proximal control mechanism 1970 adapted for user control of the delivery device and implant. The control mechanism includes a hand grasper 1972, 1972' with four-bar linkages 1974. When a user presses down on the hand grasper, the device adapts its configuration from angled to flat, which pulls the catheter proximally (toward the user) to actuate the implant within the patient.

Figure 25:
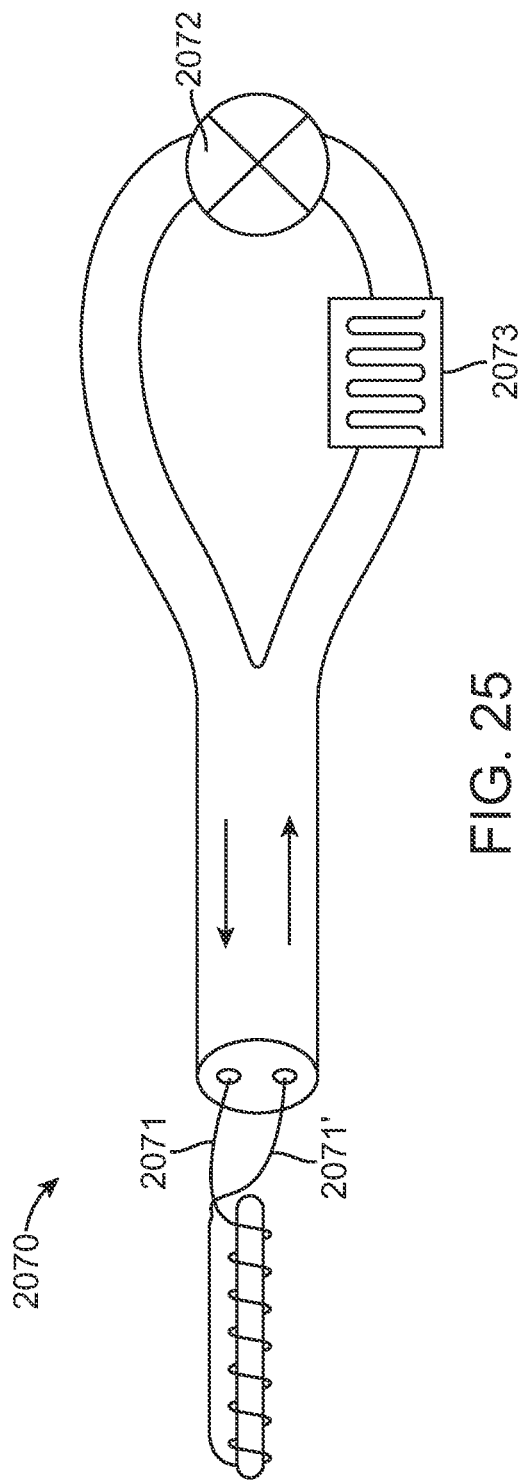
FIG. 25 illustrates another proximal control device and delivery catheter system for actuating an implant while maintaining a desired temperature at a distal end.

The device illustrated in FIG. 25 is another proximal control mechanism 2070 adapted for the user to control the temperature of a Nitinol self-recovering implant during the deployment process. In this embodiment, cold saline is advanced distally 2071 to maintain the Nitinol implant in a martensitic state (i.e., a state having a "soft" microstructure that allows deformation). A return path 2071' is provided to bring the saline back to the mechanism for cooling. Maintenance of the martensite state enables the device to remain flexible and soft during implant delivery without modifying the implant's programmed shape. Chilled saline, liquid nitrogen, liquid $CO_2$ or other suitable materials that are colder than body temperature, can be pumped 2072 or circulated to the implant. A chiller 2073 can be provided to cool down the material circulating to the device on its return path. In some embodiments, it may be desirable to control the temperature of the device, e.g., during the implantation process with a distal temperature sensor and feedback that may be transmitted via electric signal on a wire or electro-magnetic waves in a wireless fashion.

Figure 26:
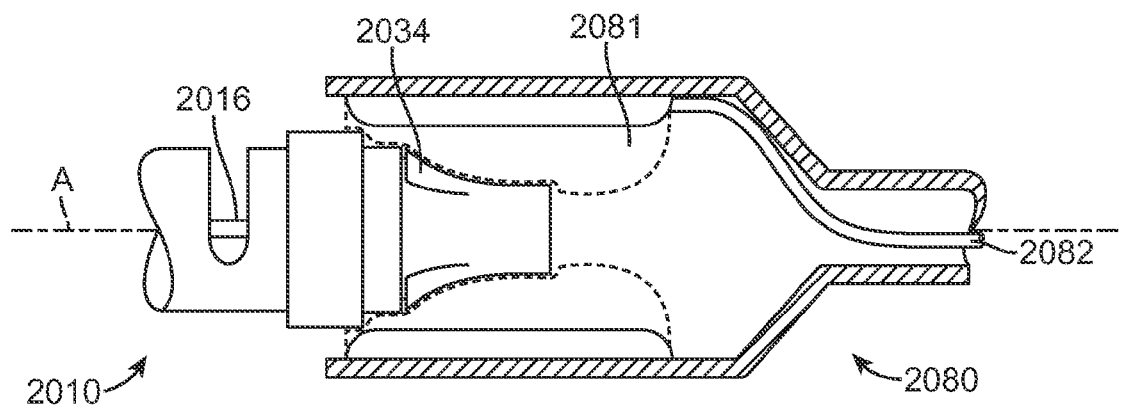
FIG. 26 illustrates yet another proximal control device for use in recapture of an implanted device.
Figure 27A:
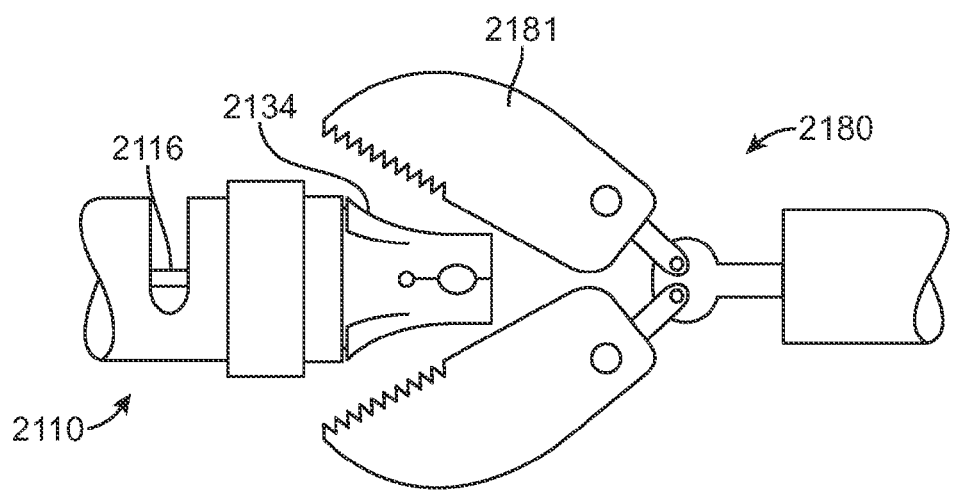
FIGS. 27A-27B illustrates an alternative embodiment of a retrieval device.
Figure 27B:
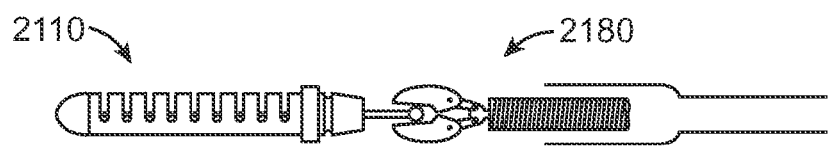

Turning now to FIG. 26, a distal configuration of a recapture device 2080 is depicted. The proximal end of the implanted device 2010 is engaged by the recapture device 2080 which is adapted to encircle the exterior of the implanted device. The device comprises a high pressure balloon 2081 adapted to engage a recovery catheter. An inflation port 2082 is provided through which, for example, cold fluid can be pumped to facilitate deflecting the nitinol tabs 2034. Once the tabs are deflected and moved toward the central axis A of the device, the lock mechanism holding the actuation wire in a curved condition can be released, the implanted device straightened and withdrawn. FIGS. 27A-B illustrates an alternative embodiment of a retrieval device 2180, where forceps are used to provide lateral force on the tabs, thus pressing the tabs in toward the central axis of the device to enable the lock mechanism holding the actuation wire to be released as described above. As illustrated in FIG. 27B, the forceps can then withdrawn the straightened device by pulling on the device.

Figure 28A:
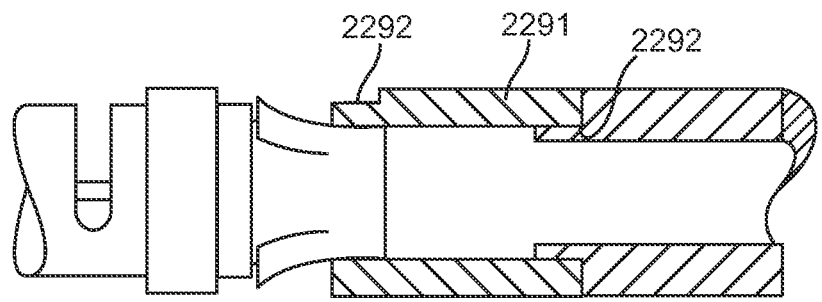
FIGS. 28A-28B illustrate device components adapted to engage each other.
Figure 28B:
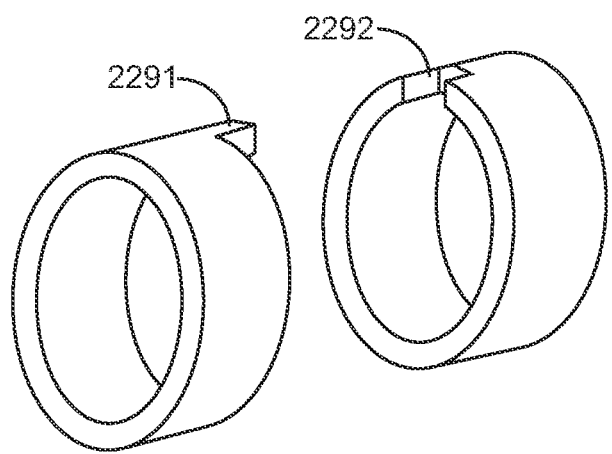

A variety of mechanisms can be used to couple the clip of the device to the catheter. As shown in FIGS. 28A-B, the implantable device 2210 has a ring with a key 2291 associated with one of the device or the delivery catheter and a keyway 2292 associated with an opposing ring associated with remaining one of the device or delivery catheter. As will be appreciated by those skilled in the art, more than one key or keyway can be provided, as desired, to control the torque. As shown in FIG. 28B, the two rings are adapted to abut each other to lock the device and allow transfer for torque between the catheter and the device. The key: keyway design illustrated in FIG. 28B can also be applied to the delivery or retrieval of devices and to the proximal end of the device.

Figure 29C:
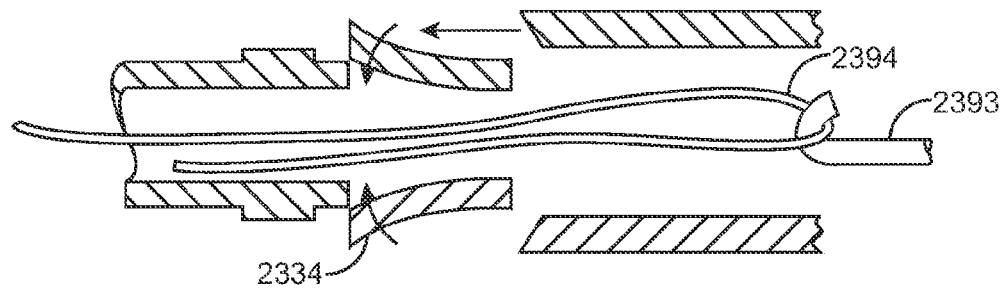
Figure 30A:
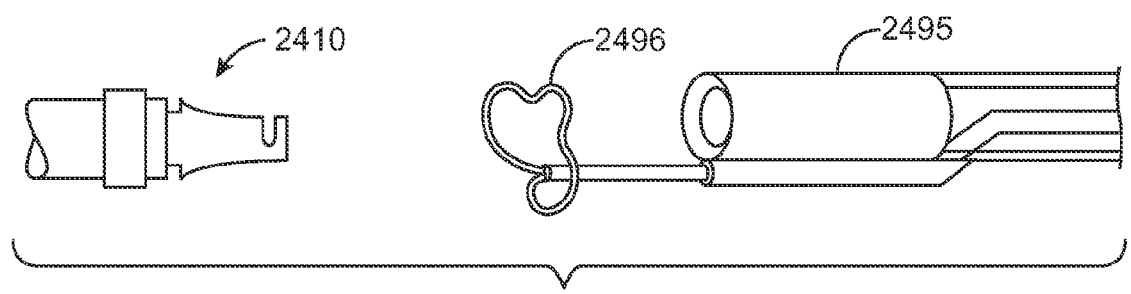
FIGS. 30A-30B illustrate a retrieval device comprising a snare wire.
Figure 30B:
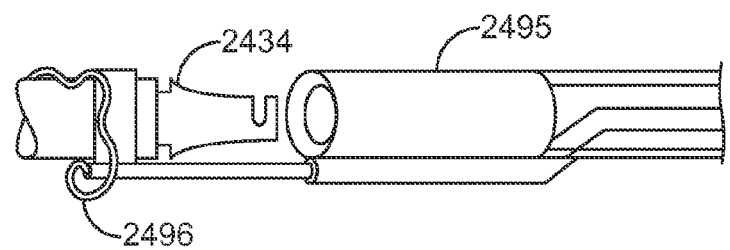

FIGS. 29A-C illustrates another retrieval mechanism 2380. The retrieval mechanism employs a hook 2393 adapted to hook into a loop 2394 at the proximal end of the device. The hook can be incorporated into the actuation mechanism 2316 such that hook 2393 extends from the actuation mechanism at the proximal end of the device 2310. Once hooked the apparatus de-activates the locking mechanism, which releases the tension on the actuator 2316. The catheter is then advanced to engage the locking flanges 2334 to push them in toward a central axis A, unlocking the device 2310 by removing tension from the actuation member 2316 and allowing the device to be withdrawn or relocated. In yet another embodiment illustrated in FIGS. 30A-B, a hypotube 2495 associated with, for example, a catheter is adapted to slide over the proximal end of the device 2410. A snare wire 2496 is configured to fit over the proximal end of the device much like a lasso. In operation, the snare wire 2496 is looped over the proximal end of the device 2410, and pulled proximally to push the hypo tube distally toward the device. This enables the combination to hold onto the implant, advance the locking hypo tube forward to unlock the tabs or flanges 2434.

Figure 31A:
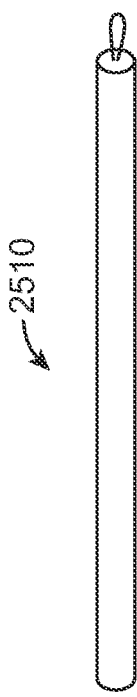
FIGS. 31A-31D illustrates devices in a variety of deployed conditions.
Figure 31B:
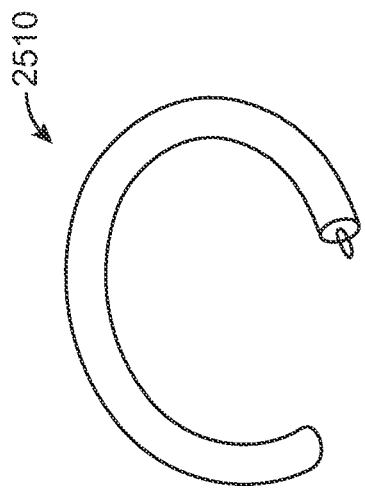
Figure 31C:
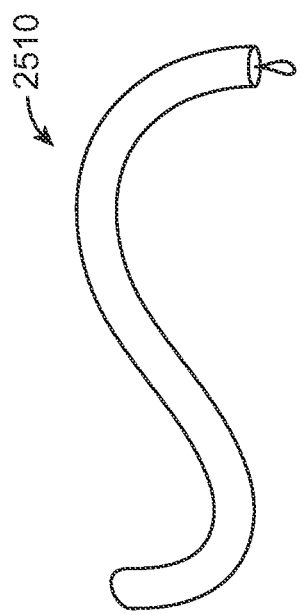
Figure 31D:
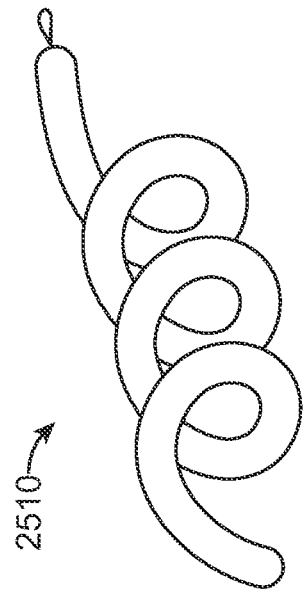

FIGS. 31A-D illustrates devices 2510 according to the invention in a variety of deployed configurations. FIG. 31A illustrates the device 2510 having a longitudinal configuration, such as the configuration assumed prior to deployment. When the device is implanted and placed in compression or tension axially, the device will preferentially bend. The actual preferential bending will vary depending upon the configuration of the device. For example, the location, depth, and orientation of the slots depicted in FIGS. 4-8; or the orientation of the walls of the segments of FIG. 9. As FIG. 31B illustrates, for example, where the device 2510 has evenly spaced c-cuts or notches along its length the device will preferentially bend such that the walls of forming the "c" or notch will approach each other, or pinch together, resulting in a deployed device that has preferentially bent into a curved "c" shape (see, FIGS. 4-5). This results because as tension is applied on the actuation device, or wire, the implant deforms and the wire takes a shorter path. FIG. 31C illustrates a device deployed into an "S" shape, such as would be achieved using a configuration like that depicted in FIG. 6. As will be appreciated, the S-shape could continue, much like a sine wave, in an many curves as desired depending upon the configuration of the device. FIG. 31D illustrates a device deployed into a spiral configuration (see, FIG. 7). As will be appreciated by those skilled in the art upon reviewing this disclosure, other configurations can be achieved by, for example, altering the size and location of the c-cuts on the tubular member, or by altering the configuration of the segments illustrated in FIGS. 9-10. Once the device preferentially bends, the device imparts a bending force on the lung tissue which results in a reduction of lung volume. As is appreciated, from the configurations shown in FIG. 31 the implant, once re-shaped, is shorter in length than the deliverable implant configuration. The shortening occurs when for example, the distance between the proximal end and the distal end is reduced. Typically, the deliverable shape of the device is such that it fits within a cylindrical space that is 18 mm in diameter or smaller. Thus, the implant can come into contact with tissue that is larger than $10^{-6}$ square inches per linear inch of the implant length. The re-shaped or deployed implant can be configured in a variety of shapes to lie within a single plane, or to adopt any other suitable configuration, such that it does not lie within a single plane. Additionally, the device can have varying rates of curvature along its length.

Figure 32:
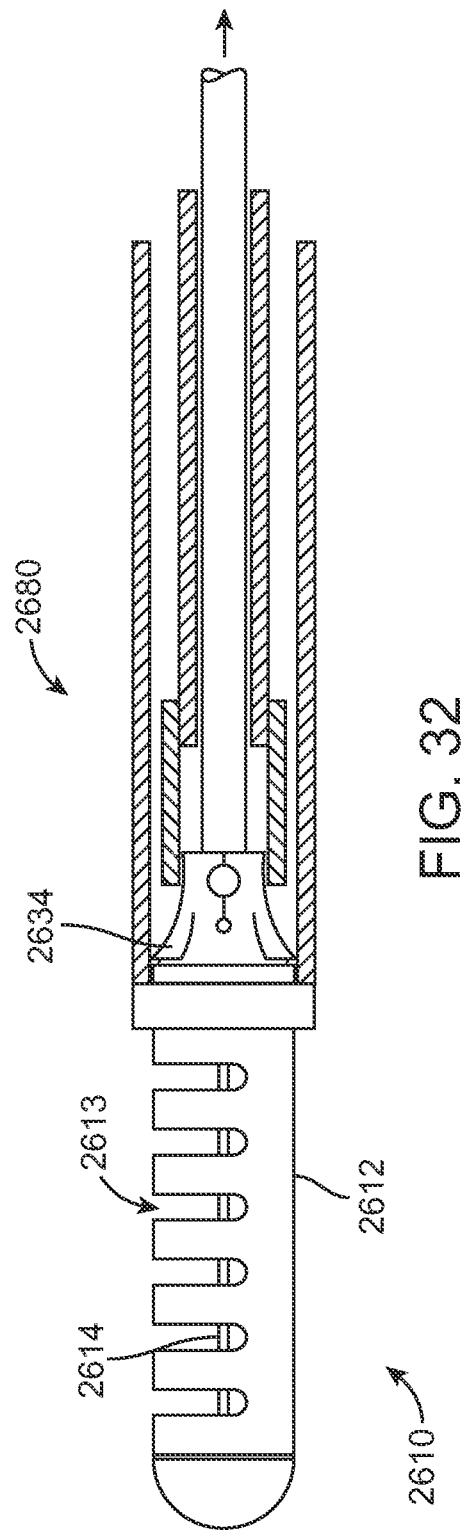
FIG. 32 illustrates a lung volume reduction device in combination with a delivery catheter.

FIG. 32 illustrates a lung volume reduction device 2610 in combination with a delivery device 2680. The device 2610 is adapted to provide a tubular member 2612 having a lumen 2613 through which an actuation element 2614 is provided. The tubular member 2612 has a series of c-cuts 2614 along its length that enable the device to preferentially bend when deployed. As will be appreciated, for purposes of illustration, a device similar to that depicted in FIG. 4 has been illustrated. Other devices can be used without departing from the scope of the invention. A device 2680 is provided that engages flanges 2634 of a lock mechanism to push the flanges in toward a central axis enabling tension applied to the actuation element 2614 to be relieved, thus enabling the device to be removed. The device can be activated by pulling the central rod in a proximal direction. The decoupler (outer rod) is then pulled in the proximal direction.

Figure 33A:
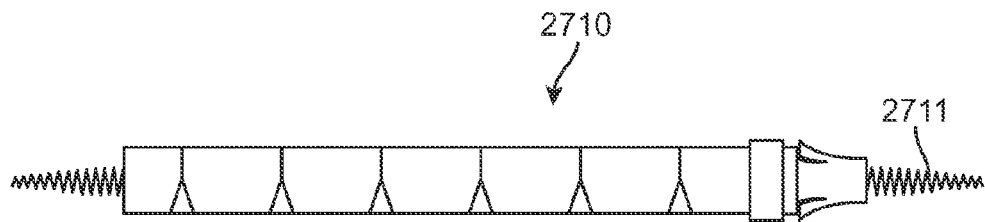
FIGS. 33A-33C illustrate a variety of device configurations with atraumatic tips.
Figure 33B:
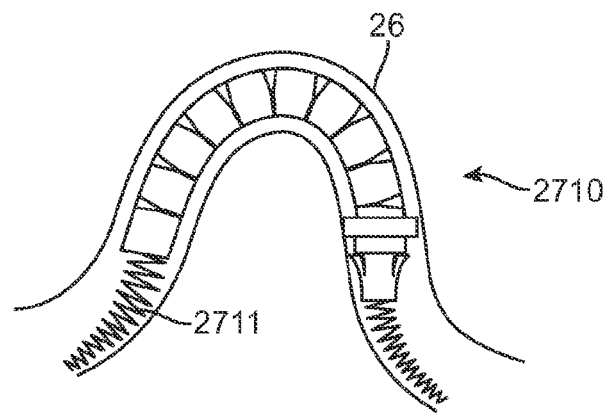
Figure 33C:
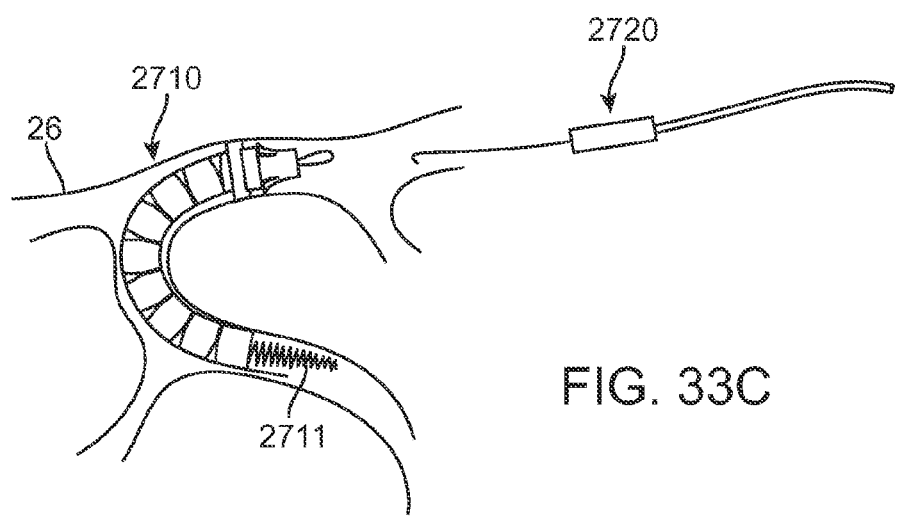

FIGS. 33A-C illustrates devices 2710 according to the invention implanted within, for example, a bronchiole 26. The device 2710 depicted in FIG. 33A is configured to provide an atraumatic tip 2711 on either end of the device. When the device 2710 is activated within the bronchiole 26 the device curves and imparts a bending force on the lung tissue. As a result of the bending pressure, the tissue curves and compresses upon its self to reduce lung volume. Additionally, deployment of the device can result in the airway becoming bent. As illustrated in FIG. 33C the device can also be configured with a single atraumatic tip so that the deployment mechanism 2720 can easily interface with the proximal end of the device.

Figure 34A:
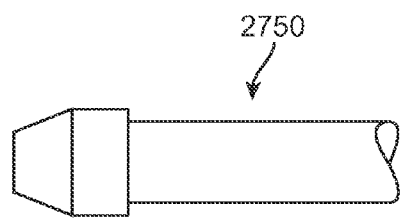
FIGS. 34A-34B illustrate a withdrawal system having a blade to separate the device from the surrounding tissue.
Figure 34B:
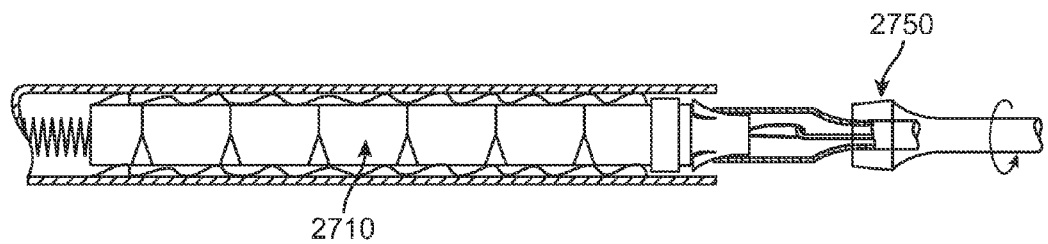

In some instances, where the device has been implanted for a length of time sufficient for tissue in-growth to occur, a torquable catheter 2750 having a sharp blade (not shown) within its lumen can be advanced along the length of the device 2710 to enable tissue to be cut away from the implant prior to withdrawal such as shown in FIGS. 34A-B. This enables the device to be cut away from the airway wall in order to facilitate withdrawal.

Figure 35A:
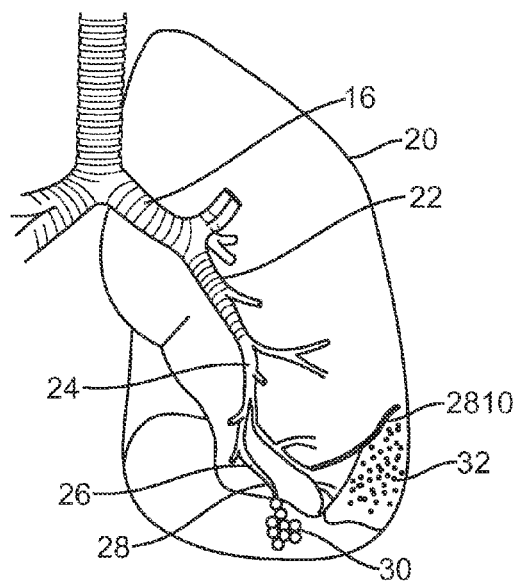
FIGS. 35A-35C illustrate a device implanted within the lungs.
Figures 35B, 35C:
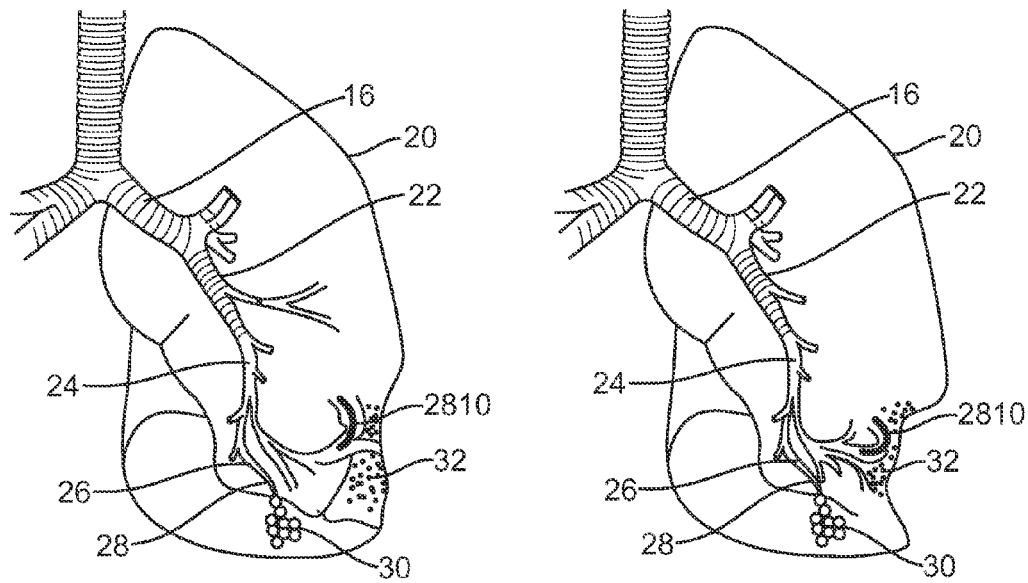

FIG. 35A-C illustrates the process of implanting the device within a lung. As is evidence, the device 2810 is advanced is a configuration where the device adapts to the anatomy of the lungs through the airways and into, for example, the bronchioles until it reaches a desired location relative to the damaged tissue 32. The device is then activated by engaging the actuation device, causing the device to curve and pull the lung tissue toward the activated device (see, FIG. 35B). The device continues to be activated until the lung tissue is withdrawn a desired amount, such as depicted in FIG. 35C. As will be appreciated by those skilled in the art, withdrawing the tissue can be achieved by, for example, curving and compressing a target section of lung tissue upon deployment of one of the configurable devices disclosed herein. Once activated sufficiently, the deployment device is withdrawn from the lung cavity.

Figure 36A:
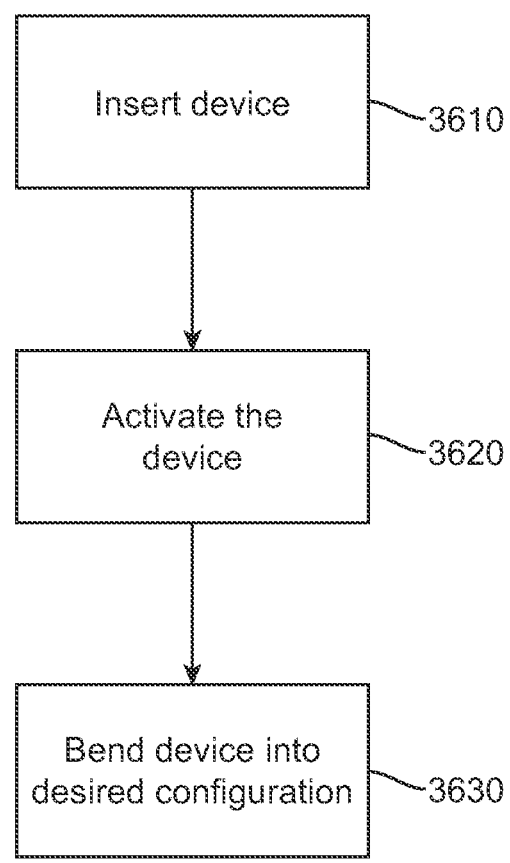
FIG. 36A illustrates a method steps for implanting the device.

A variety of steps for performing a method according to the invention would be appreciated by those skilled in the art upon review of this disclosure. However, for purposes of illustration, FIG. 36A illustrates the steps including, insertion of the device 3610, activating the device 3620, such as by activating an actuator; bending the device into a desired configuration 3630 and locking the device into a deployed condition. As will be appreciated the step of bending the device can be achieved by activating the actuator, as described above, or by the implant being restored into a preconfigured shape.

In one embodiment, the device operation includes the step of inserting a bronchoscope into a patient's lungs and then inserting an intra-bronchial device or lung volume reduction device into the bronchoscope. The intrabronchial device is then allowed to exit the distal end of the bronchoscope where it is pushed into the airway. A variety of methods can then be used to verify the positioning of the device to determine if the device is in the desired location. Suitable methods of verification include, for example, visualization via visualization equipment, such as fluoroscopy, CT scanning, etc. Thereafter the device is activated by pulling the pull wire proximally (i.e., toward the user and toward the exterior of the patient's body). At this point, another visual check can be made to determine whether the device has been positioned and deployed desirably. Thereafter, the device can be fully actuated and the ratchet can be allowed to lock and hold the device in place. Thereafter, the implant is decoupled from the delivery catheter and the delivery catheter is removed.

Figure 36B:
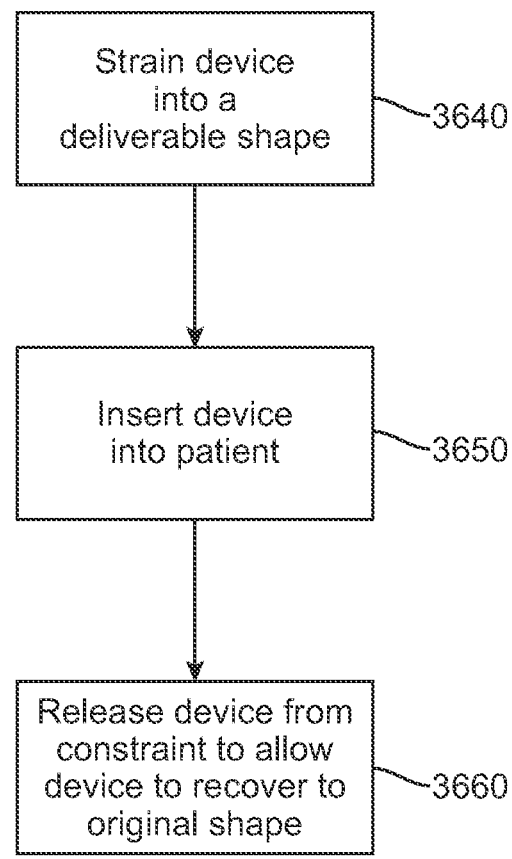
FIG. 36B illustrates a method steps for implanting the device.

Another method of tensioning the lung is shown in FIG. 36B which illustrates steps that include, applying bending loads or force to strain a device from a first shape into a deliverable shape without plastically or permanently bending the device 3640, delivering the device into the patient using the bronchoscope or other delivery system components to hold the device in a deliverable shape while it is being introduced 3650 and then removing the constraint used to hold the device to allow it to recover back to it's first shape 3660. Elastic recovery of the device will drive the device to a more bent condition that will apply force to nearby lung tissue. The bending forces locally compress tissue near the implant and apply tension on lung tissue in surrounding regions to restore lung recoil and enhance breathing efficiency. The first shape is adapted to be elastically constrained by a delivery device to a deliverable configuration whereby removal of the delivery device allows the implant to recoil and be reshaped closer to its first shape.

FIG. 37 shows an example of an implantable device 3703 made from Nitinol metal wire 3701. Nickel-Titanium, Titanium, stainless steel or other biocompatible metals with memory shape properties or materials with capabilities to recover after being strained 1% or more may be used to make such an implant. Additionally, plastics, carbon based composites or a combination of these materials would be suitable. The device is shaped like a French horn and can generally lie in a single plane. The ends are formed into a shape that maximizes surface area shown in the form of balls 3702 to minimize scraping or gouging lung tissue. The balls may be made by melting back a portion of the wire, however, they may be additional components that are welded, pressed or glued onto the ends of wire 3701.

A Nitinol metallic implant, such as the one illustrated in FIG. 37, may be configured to be elastic to recover to a desired shape in the body as any other type of spring would or it can be made in a configuration that may be thermally actuated to recover to a desired shape. Nitinol can be cooled to a martensite phase or warmed to an austenite phase. In the austenite phase, the metal recovers to its programmed shape. The temperature at which the metal has fully converted to an austenite phase is known as the Af temperature (austenite final). If the metal is tuned so that the Af temperature is at body temperature or lower than body temperature, the material is considered to be elastic in the body and it will perform as a simple spring. The device can be cooled to induce a martensite phase in the metal that will make the device flexible and very easy to deliver. As the device is allowed to heat, typically due to body heat, the device will naturally recover its shape because the metal is making a transition back to an austenite phase. If the device is strained to fit through a delivery system, it may be strained enough to induce a martensite phase also. This transformation can take place with as little as 0.1% strain. A device that is strain induced into a martensite phase will still recover to its original shape and convert back to austenite after the constraints are removed. If the device is configured with an Ar temperature that is above body temperature, the device may be heated to convert it to austenite and thermally activate its shape recovery inside the body. All of these configurations will work well to actuate the device in the patient's lung tissue. The human body temperature is considered to be 37 degrees C. in the typical human body.

FIG. 38 illustrates a cutaway view of a delivery cartridge system 3800 that constrains the implant device 3703 in a deliverable shape. The device 3801 may be shipped to the intended user in such a system or it may be used as a tool to more easily load the implant into a desired shape before being installed into the patient, bronchoscope or a catheter delivery device. The cartridge may be sealed or terminated with open ends or one or more hubs such as the Luer lock hub 3802 that is shown. The implant should be constrained to a diameter that is the same or less than 18 mm diameter because anything larger than that will be difficult to advance past the vocal cord opening.

FIG. 39 illustrates another implant device 3901 that is shaped in a three dimensional shape similar to the seam of a baseball. The wire is shaped so that proximal end 3902 extends somewhat straight and slightly longer than the other end. This proximal end will be the end closest to the user and the straight section will make recapture easier. If it were bent, it may be driven into the tissue making it hard to access.

FIG. 40 is an illustration of another implant system 4001. It is similar to that shown in FIG. 39 with the addition of a wire frame 4002 surrounding the device. The wire frame may be used, for example, to increase the bearing area that is applied to the lung tissue. By increasing the bearing area, the pressure born by the tissue is reduced along with a reduction in the propensity for the device to grow through lung structures or cause inflammatory issues. Small wires that apply loads in the body tend to migrate so we believe that the device should be configured to possess more than 0.000001 ($1^{-6}$ in$^2$) square inches of surface area per linear inch of the length of the device. The frame is one of many ways to provide a larger surface area to bear on the tissue.

FIG. 41 shows yet another example of a device 4101 according to the invention. The device 4101 features a covering to increase bearing area 4102. In this example, the main wire 3902 is covered by a wire frame and a polymeric covering 4102. The covering may be made of any biocompatible plastic, thermoplastic, fluoropolymer, Teflon®, urethane, metal mesh, coating, silicone or other resilient material that will reduce the bearing pressure on the lung tissue. The ends of the covering 4103 may remain sealed or open as shown to allow the user to flush antibiotics into and out of the covering.

FIG. 42 illustrates another configuration of the implant device 4201 showing a covering 4205 with perforations 4203 adapted and configured to allow the device to be flushed. The ends 4202 of the covering are sealed to the ends of the device to keep the two components fixed and prevent sliding of one or the other during deployment. The covering may be thermally bonded, glued or shrunk to a tight fit.

Figure 43:
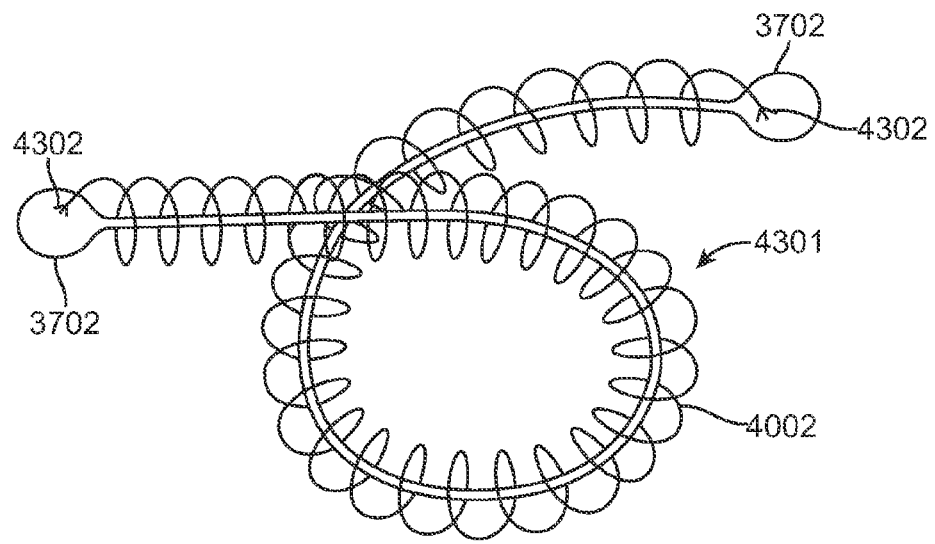
FIG. 43 illustrates a device configuration with an attached wire support frame.

FIG. 43 illustrates a device 4301 that has the wire frame 4002 joined to the ball ends 3702 at a junction 4302. The balls may be melted from the wire stock and the wire frame may be incorporated into the ball at that time. It may also be glued, pressed together, welded or mechanically locked together.

Figure 44:
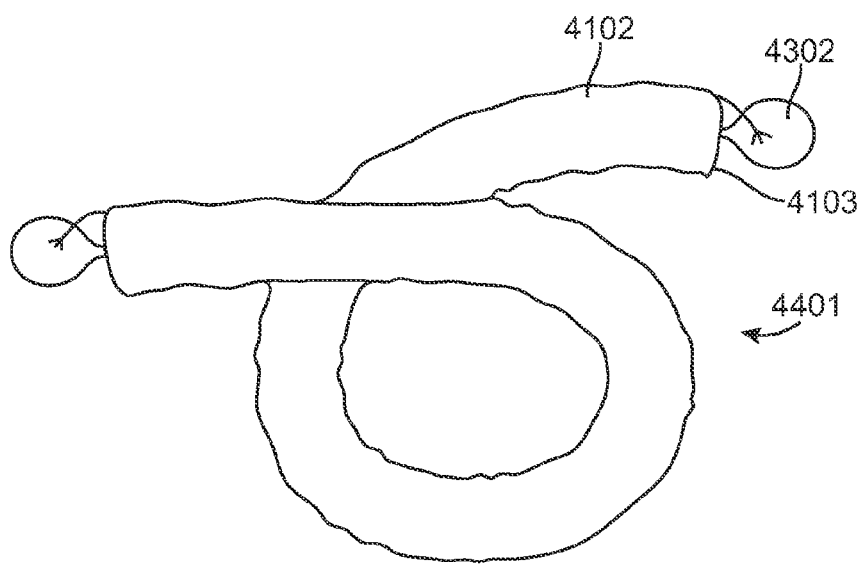
FIG. 44 illustrates a device configuration with an attached frame and covering.

FIG. 44 illustrates another implant device 4401 with an attached wire frame 4302, main wire 4103 and a covering 4102.

Figure 45:
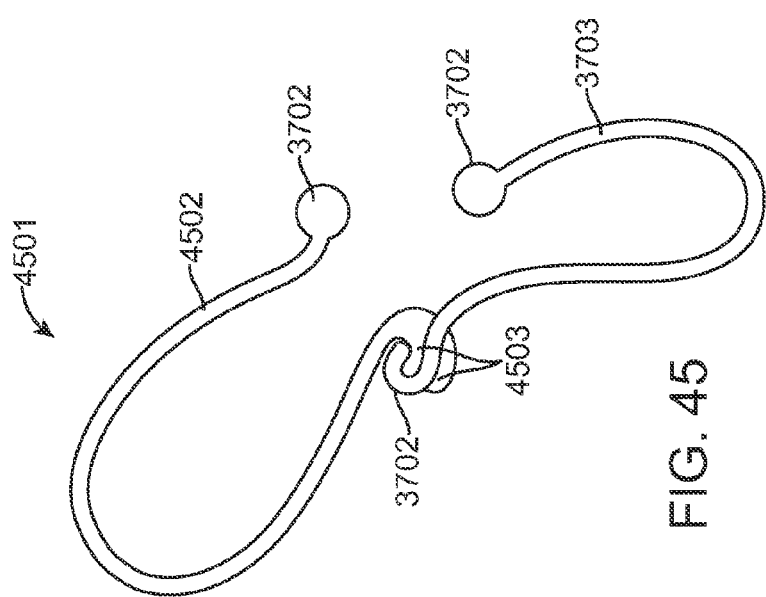
FIG. 45 illustrates a device configuration that is coupled to a second device.

FIG. 45 illustrates a system of one or more devices that can be hooked together 4501. The device 3703 is configured such that it terminates on both ends, for example, with blunt ball shaped ends 3702. The device 4502 is terminated on one end with an open cup and slot shape 4503 that allows the devices to be coupled together. These devices may be delivered together or coupled in-situ. Devices may be installed into a single duct in the lung or in different locations that may be linked together.

Figure 46:
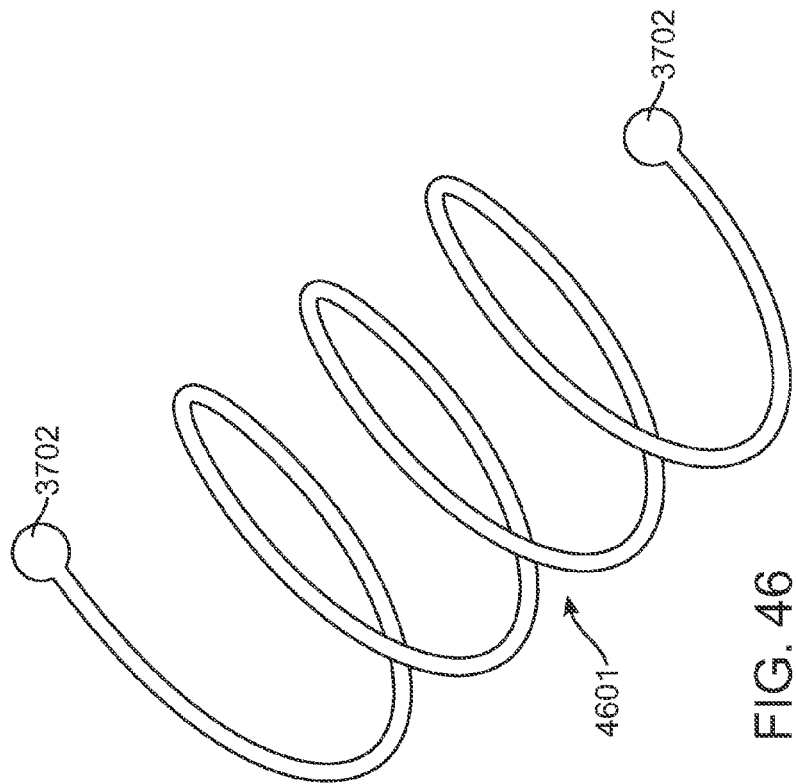
FIG. 46 illustrates a device configuration in a coil shape.

FIG. 46 illustrates another three dimensional device 4601 made in the form of a coil with ball terminations 3702.

Figure 47:
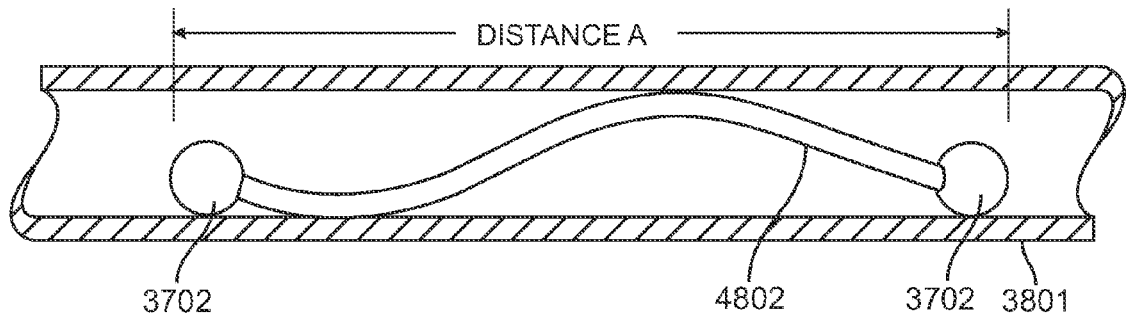
FIG. 47 illustrates a length change from delivery to deployed.
Figure 48:
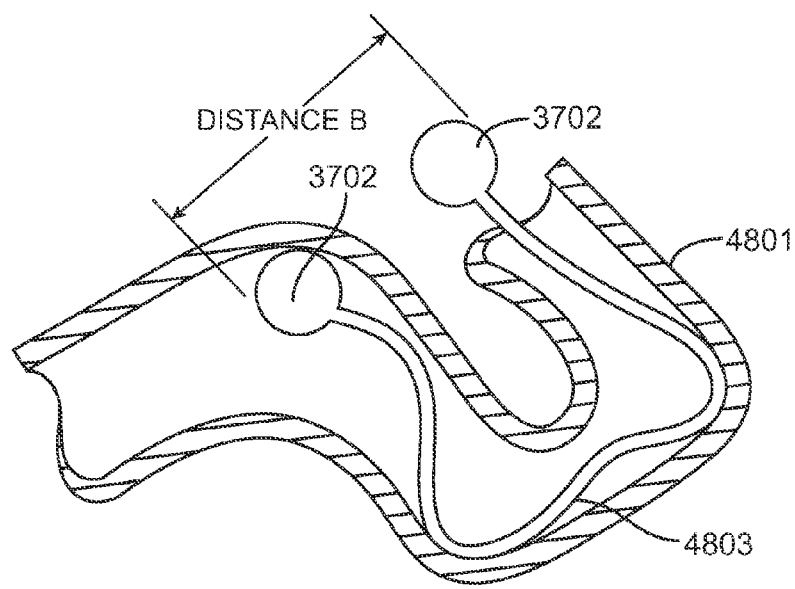
FIG. 48 illustrates a system with bronchoscope, catheter, dilator, wire steering handle.

FIGS. 47 and 48 illustrate how the device length is reduced when the device is deployed in-situ. The device shown in the delivery configuration 4802 in FIG. 47 is also shown in the deployed configuration 4803 in FIG. 48. The distance A between the device ends 3702 is large while the device is constrained by the constraining cartridge device 3801. Distance A is similar when the device is constrained by a loading cartridge, catheter or bronchoscope. FIG. 48 shows the same device in a deployed configuration 4803 in an airway 4801 that has been deformed by the shape recovery of the implant device. FIG. 48 shows that the distance B between the device ends 3702 is substantially shorter after the device is deployed.

As with previous embodiments, the embodiments depicted in FIGS. 37-48 are adapted and configured to be delivered to a lung airway of a patient in a delivery configuration and to change to a deployed configuration to bend the lung airway. The devices are characterized in that the devices have a delivery configuration that is resiliently bendable into a plurality of shapes, such as the ones depicted in the Figures. The design of the devices can be such that strain relief is facilitated on both ends of the device. Further the ends of the device in either the delivery or deployed state are more resilient.

The devices can have any suitable length for treating target tissue. However, the length typically range from, for example, 2 cm to 10 cm, usually 5 cm. The diameter of the device can range from 1.00 mm to 3.0 mm, preferably 2.4 mm. The device is used with a catheter which has a working length of 60 cm to 200 cm, preferably 90 cm.

In operation the devices shown in FIGS. 37-48 are adapted and configured to be minimally invasive which facilitates easy use with a bronchoscope procedure. Typically, there is no incision, and no violation of the pleural space of the lung during deployment. Furthermore, collateral ventilation in the lung does not affect the effectiveness of the implanted device. As a result, the devices are suitable for use with either homogeneous and heterogeneous emphysema.

Each of the devices depicted in FIGS. 37-48 are adapted and configured to impart bending force on lung tissue. For example, a spring element can be provided, as illustrated in FIG. 40 that imparts bending force on lung tissue. The implantable spring element that can be constrained into a shape that can be delivered to a lung airway and unconstrained to allow the element to impart bending force on the airway to cause the airway to be bent.

Embodiments of the lung volume reduction system can be adapted to provide an implant that is constrained in a first configuration to a relatively straighter delivery configuration and allowed to recover in situ to a second configuration that is less straight configuration. Devices and implants can be made, at least partially, of spring material that will fully recover after having been strained at least 1%, suitable material includes a metal, such as metals comprising Nickel and Titanium. In some embodiments, the implant of the lung volume reduction system is cooled below body temperature in the delivered configuration. In such an embodiment, the cooling system can be controlled by a temperature sensing feedback loop and a feedback signal can be provided by a temperature transducer in the system. The device can be configured to have an Af temperature adjusted to 37 degrees Celsius or colder. Additionally, at least a portion of the metal of the device can be transformed to the martensite phase in the delivery configuration and/or can be in an austenite phase condition in the deployed configuration.

Lung volume reduction systems, such as those depicted in FIGS. 37-48, comprise an implantable device that is configured to be deliverable into a patient's lung and which is also configured to be reshaped to make the lung tissue that is in contact with the device more curved. Increasing the curvature of the tissue assists in reducing the lung volume of diseased tissue, which in turn increases the lung volume of healthier tissue. In some instances, the devices are configured to be reshaped to a permanent second configuration. However, as will be appreciated by those skilled in the art, the devices can also be adapted and configured to have a first shape and is configured to be strained elastically to a deliverable shape.

As will be appreciated by those skilled in the art, the devices illustrated in FIG. 37-48 are can be configured to be deliverable into a patient's lung and configured to reshape lung tissue while allowing fluid to flow both directions past the implant.

Figure 49:
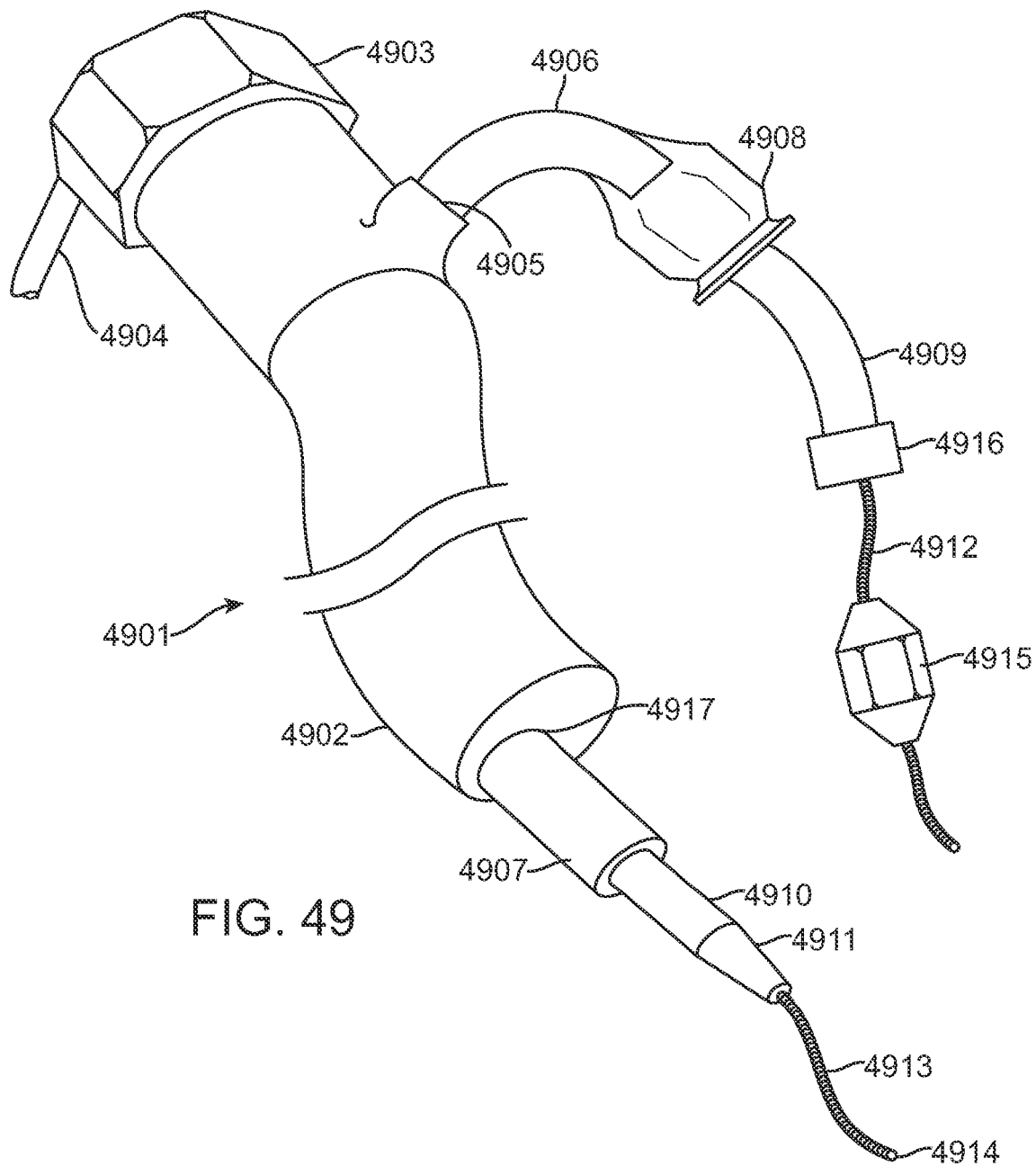
FIG. 49 illustrates a system in an airway with device ready to deliver.

FIG. 49 illustrates a system 4901 that may be used to deliver the implant device. The many components of the system may be needed to guide the bronchoscope 4902 to a site that is appropriate for implant delivery. The airway guide wire has a distal floppy section 4913 that can be steered into any desired airway by rotating the slight curve at the distal tip to the appropriate trajectory at airway bifurcations. To apply torque to the wire, devices such as a locking proximal handle 4915 may be attached to the proximal end of the wire 4912. The wire tip may be blunt such as the ball tip shown 4914. In some embodiments, the wire may be adapted and configured to pass through a dilator catheter 4909 that is shaped to provide a smooth diameter transition from the wire diameter to the delivery catheter 4906 diameter. The distal tip of the dilator 4910 should be tapered 4911 as shown. The dilator prevents the open end of the delivery catheter 4906 to dig into lung tissue in an unintended way. The dilator hub 4916 may be made as a Y-fitting to allow the user to couple a syringe and inject radiopaque dye through the dilator lumen to increase the visibility of the airways, which facilitates the use of an x-ray guidance system, such as fluoroscopy or computed tomography. The delivery catheter may be used without the wire and dilator. The catheter 4906 is designed to constrain the device in a deliverable shape while it is advanced through the system and into the patient. The distal end 4907 may be configured from a floppier polymer or braid than the proximal end 4906 and the distal tip may further include a radiopaque material associated with the tip, either integral or adjacent, to identify the position of the tip relative to other anatomical locations, such as bones. Providing one or more radiopaque markers facilitates using x-ray guidance system to position the distal end of the device in situ relative to a target anatomy. The proximal termination of the delivery catheter 4908 may further be adapted to incorporate a lockable hub to secure the loading cartridge 3801 with a smooth continuous lumen. The delivery catheter 4906 is shown introduced into the bronchoscope side port 4905 and out the distal end of the scope 4917. A camera 4903 is shown attached to the end of the scope with a cable 4904, or other delivery mechanism, to transmit the image signal to a processor and monitor. The loading cartridge, delivery catheter, dilator, guide wire and wire steering handle may be made from any material identified in this specification or materials well known to be used for similar products used in the human vascular tract by radiologists.

Figure 50:
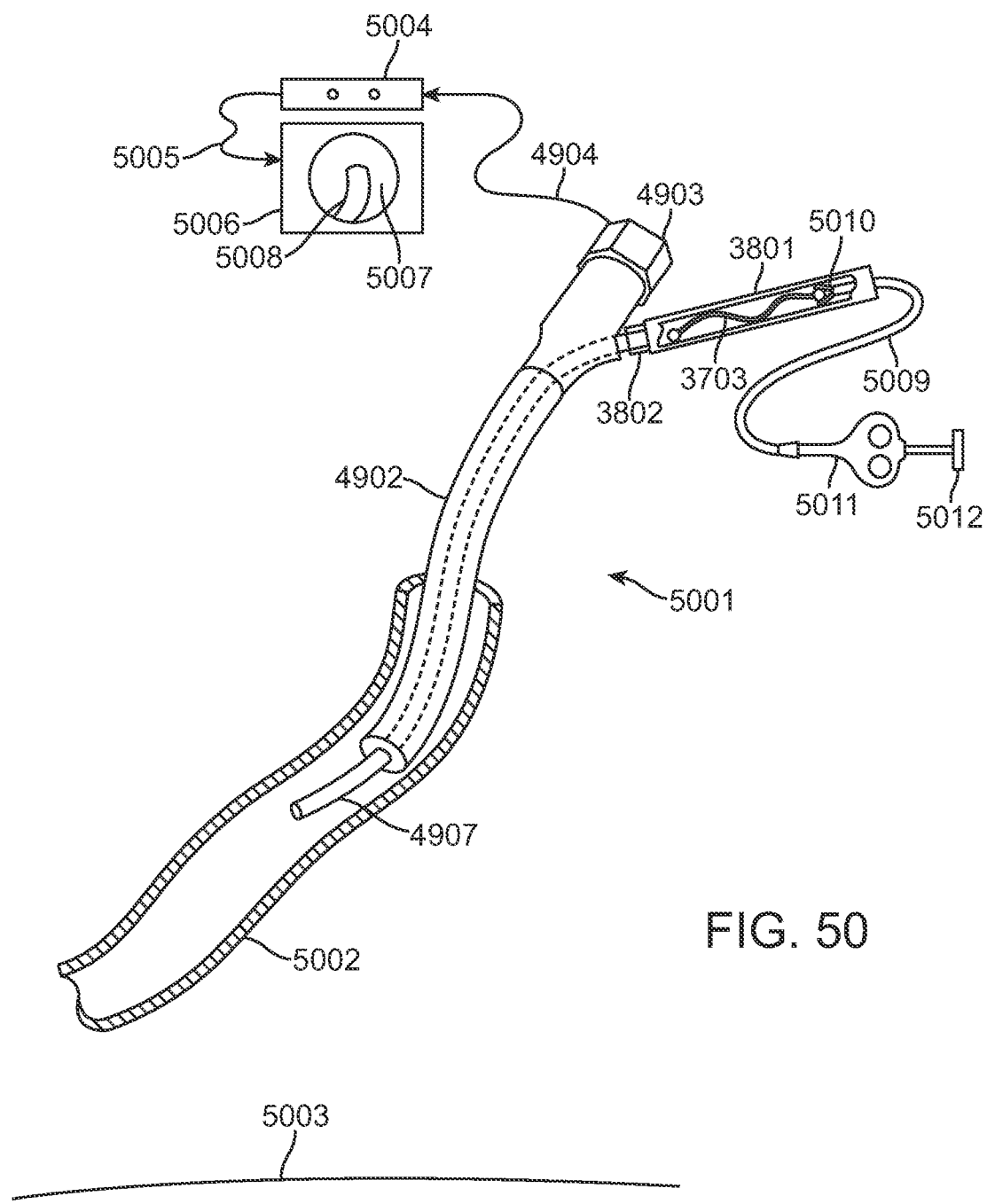
FIG. 50 illustrates a system in an airway delivering the device.

FIG. 50 illustrates a delivery system 5001 that has been placed into a human lung. The bronchoscope 4902 is in an airway 5002. The scope camera 4903 is coupled to a video processor 5004 via a cable 4904. The image is processed and sent through a cable 5005 to a monitor 5006. The monitor shows a typical visual orientation on the screen 5007 of a delivery catheter image 5008 just ahead of the optical element in the scope. The distal end of the delivery catheter 4907 protrudes out of the scope in an airway 5002 where the user will place an implant device 3703. The implant 3703 is loaded into a loading cartridge 3801 that is coupled to the proximal end of the delivery catheter via locking hub connection 3802. A pusher grasper device 5009 is coupled to the proximal end of the implant 3703 with a grasper coupler 5010 that is locked to the implant using an actuation plunger 5012, handle 5011 and pull wire that runs through the central lumen in the pusher catheter. By releasably coupling the pusher to the implant device and advancing pusher/grasper device 5009, the user may advance the implant to a position in the lung in a deployed configuration. The user can survey the implant placement position and still be able to retrieve the implant back into the delivery catheter, with ease, if the delivery position is less than ideal. The device has not been delivered and the bottom surface of the lung 5003 is shown as generally flat and the airway is shown as generally straight. These may both be anatomically correct for a lung with no implant devices. If the delivery position is correct, the user may actuate the plunger 5012 to release the implant into the patient.

Figure 51:
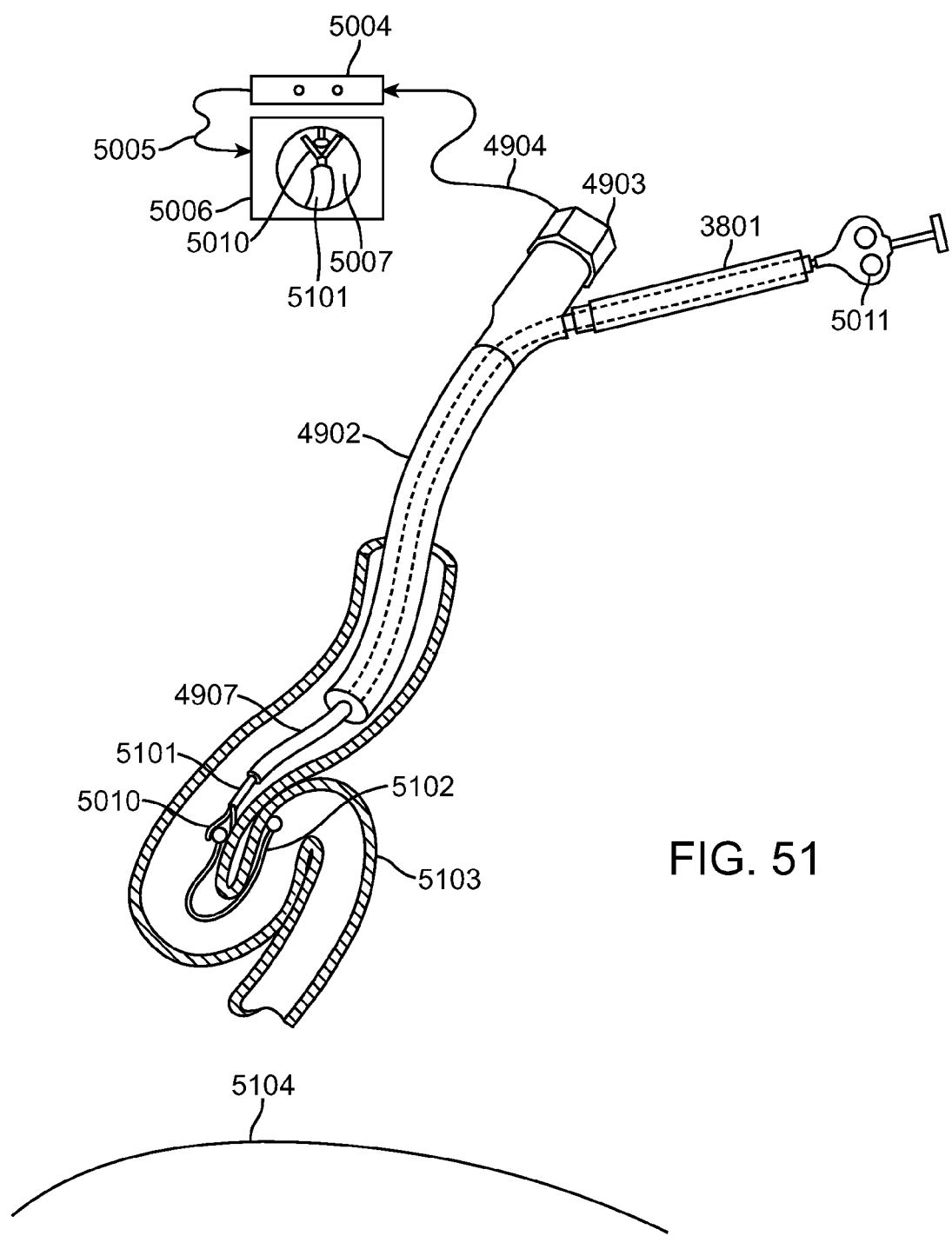
FIG. 51 illustrates a system in an airway with the device delivered.

FIG. 51 illustrates generally the same system after the implant has been deployed into the airway 5103. The implant 5102 and pusher 5101 has been advanced through the delivery catheter 4907 to a location distal to the scope 4902. The pusher grasping jaws 5010 are still locked onto the proximal end of the implant 5102 but the implant has recovered to a pre-programmed shape that has also bent the airway 5103 into a folded configuration. By folding the airway, the airway structure has been effectively shortened within the lung and lung tissue between portions of the implant has been laterally compressed. Since the airways are well anchored into the lung tissue, the airway provides tension on the surrounding lung tissue which is graphically depicted by showing the pulled (curved inward) floor of the lung 5104. The image from the camera 4903 is transmitted through the signal processor 5004 to the monitor 5006 to show the distal tip of the delivery catheter 5101, distal grasper of the pusher 5010 and proximal end of the implant 3703. The grasper may be used to locate, couple to and retrieve devices that have been released in the patient. The implant performs work on the airways and lung tissue without blocking the entire lumen of the airway. This is a benefit in that fluid or air may pass either way through the airway past the implant device.

Figure 52:
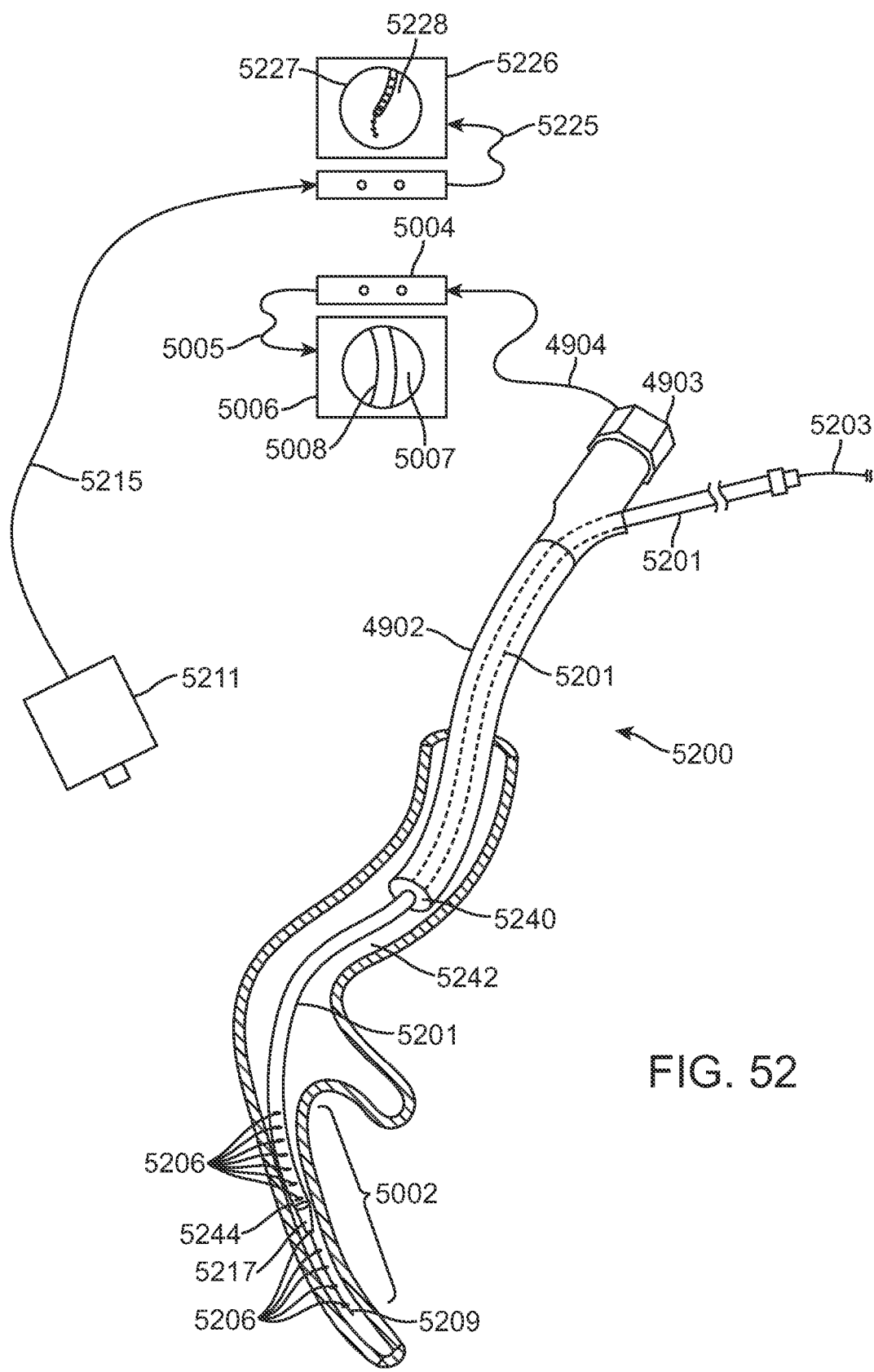
FIG. 52 illustrates a system with a bronchoscope, catheter, dilator, and guidewire.

FIG. 52 illustrates delivery system 5200 as placed into a patient body, and particularly into a human lung. Delivery system 5200 may be generally similar to system 4901 or 5001 described above. The distal end 5240 of bronchoscope 4902 extends into an airway system toward an airway portion or axial region 5002, sometimes referred to as an axial segment. The scope camera 4903 is coupled to a video processor 5004 via a cable 4904. The image is processed and sent through a cable 5005 to a monitor 5006. Monitor 5006 shows on screen 5007 a portion of a delivery catheter image 5008 just ahead of the optical image capture element in the scope. In some embodiments, the scope may be constrained by a relatively large cross-section to advancement only to a "near" region of the lung adjacent the major airways. Hence, the optical image has a viewfield that extends only a limited distance along the airway system, and it will often be desirable to implant some, most, or all of the implant beyond a field of view 5242 of scope 4902.

Guidewire 5203 is threaded through bronchoscope 4902 and through the airway system to (and through) airway 5002. As described above, guidewire 5203 may optionally have a cross-section significantly smaller than that of the scope and/or the delivery catheter. Alternative embodiments may use a relatively large diameter guidewire. For example, rather than relying on a tapering dilator between the guidewire and the delivery catheter, the guidewire may instead be large enough to mostly or substantially fill the lumen of the delivery catheter, while still allowing sliding motion of the guidewire through the lumen. Suitable guidewires may have cross-section in a range from about 5 Fr to about 7 Fr, ideally being about 5½ Fr, while the delivery catheter may be between about 5 Fr and 9 Fr, ideally being about 7 Fr. A distal end 5209 of the guidewire 5203 may be angled as described above to facilitate steering. Still further variations are also possible, including delivery of the implant directly thru a working lumen of an endoscope (with use of a separate delivery catheter). In particular, where a cross-sectional size of a bronchoscope allows the scope to be advanced to a distal end of the target airway region, the bronchoscope itself may then be used as a delivery catheter, optionally without remote imaging.

A fluoroscopic system, an ultrasound imaging system, an MRI system, a computed tomography (CT) system, or some other remote imaging modality having a remote image capture device 5211 allows guidance of the guidewire so that the guidewire and/or delivery catheter 5201 can be advanced beyond the viewing field of bronchoscope 4902. In some embodiments, the guidewire may be advanced under remote image guidance without the use of a scope. Regardless, the guidewire can generally be advanced well beyond the near lung, with the distal end of the guidewire often being advanced to and/or through the mid-lung, optionally toward or to the small airways of the far lung. When a relatively large guidewire is used (typically being over 5 Fr, such as a 5½ Fr guidewire), the cross-section of the guidewire may limit advancement to a region of the airway having a lumen size appropriate for receiving the implants described above. The guidewire may have an atraumatic end, with exemplary embodiments having a guidewire structure which includes a corewire affixed to a surrounding coil with a resilient or low-column strength bumper extending from the coil, the bumper ideally formed by additional loops of the coil with separation between adjacent loops so as to allow the bumper to flex axially and inhibit tissue damage. A rounded surface or ball at the distal end of the bumper also inhibits tissue injury. A distal end 5244 of laterally flexible delivery catheter 5201 can then be advanced through the lumen within bronchoscope 4902 and over guidewire 5203 under guidance of the imaging system, ideally till the distal end of the delivery catheter is substantially aligned with the distal end of the guidewire.

The distal portion of guidewire 5203 is provided with indicia of length 5206, the indicia indicating distances along the guidewire from distal end 5209. The indicia may comprise scale numbers or simple scale markings, and distal end 5244 of catheter 5201 may have one or more corresponding high contrast markers, with the indicia of the guidewire and the marker of the catheter typically visible using the remote imaging system. Hence, remote imaging camera 5211 can identify, track or image indicia 5206 and thus provide the length of the guidewire portion extending between (and the relative position of) the distal end of the bronchoscope and the distal end 5209 of guidewire 5203. Indicia of length 5206 may, for example, comprise radiopaque or sonographic markers and the remote imaging modality may comprise, for example, an x-ray or fluoroscopic guidance system, a computed tomography (CT) system, an MRI system, or the like. Exemplary indicia comprise markers in the form of bands of high-contrast metal crimped at regular axial intervals to the corewire with the coil disposed over the bands, the metal typically comprising gold, platinum, tantalum, iridium, tungsten, and/or the like. Note that some of the indicia of the guidewire are schematically shown through the distal portion of the catheter in FIG. 52. Indicia of length 5206 thus facilitate using a guidance system to measure a length of airway 5002 or other portion of the airway system beyond the field of view of the scope, thereby allowing an implant of appropriate length to be selected.

Remote imaging modality 5221 is coupled to imaging processor 5224 via cable 5215. Imaging processor 5224 is coupled to a monitor 5226 which displays an image 5228 on screen 5227. Image 5228 shows the indicia of lengths 5205 and 5206 of delivery catheter 5201 and guidewire 5203, respectively. As described above, when a small-diameter guidewire is used a dilator 5217 may be advanced through the lumen of the catheter so that the distal end of the dilator extends from the distal end of delivery catheter 5201 when the catheter is being advanced. Dilator 5217 atraumatically expands openings of the airway system as delivery catheter 5201 advances distally. Dilator 5217 tapers radially outwardly proximal of the distal tip of guidewire 5203, facilitating advancement of the catheter distally to or through the mid-lung toward the far lung. Once the catheter has been advanced to the distal end of airway portion 5002 targeted for delivery (optionally being advanced over the guidewire to the distal end of the guidewire when a large diameter guidewire is used to identify a distal end of a target region for an implant, or as far as the cross-section of the catheter allows the catheter to be safely extended over a smaller diameter guidewire), the length of the airway (optionally between the distal end of the guidewire and the distal end of the bronchoscope) is measured. The dilator 5217 (if used) and guidewire 5203 are typically withdrawn proximally from deliver catheter 5201 so as to provide an open lumen of the delivery catheter from which a lung volume reduction device or implant can be deployed.

Figure 53A:
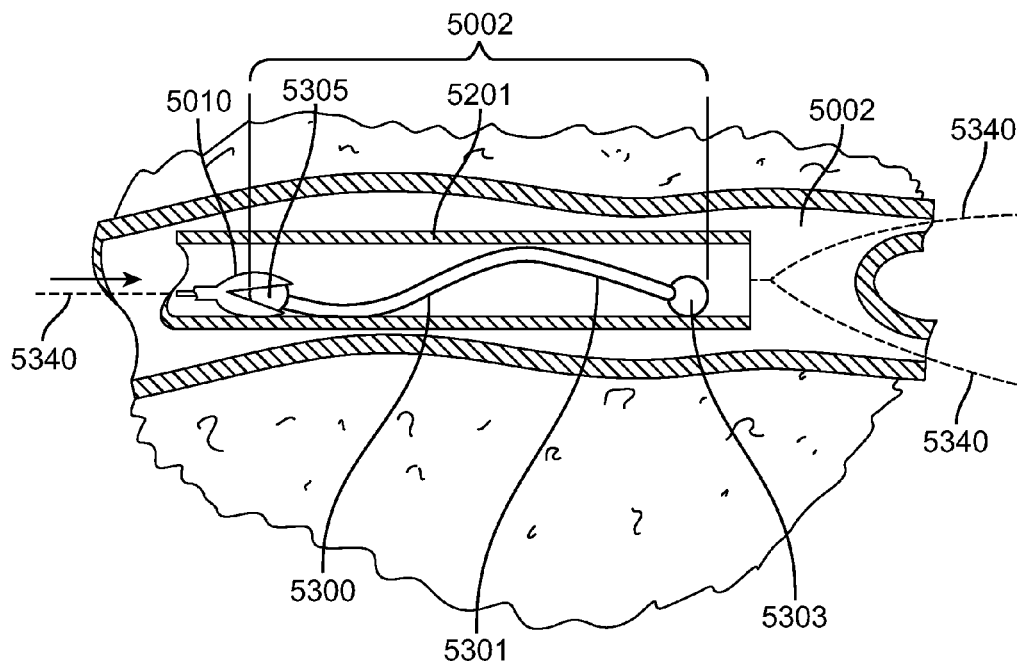
FIGS. 53A-53B illustrate the delivery of the device.
Figure 53B:
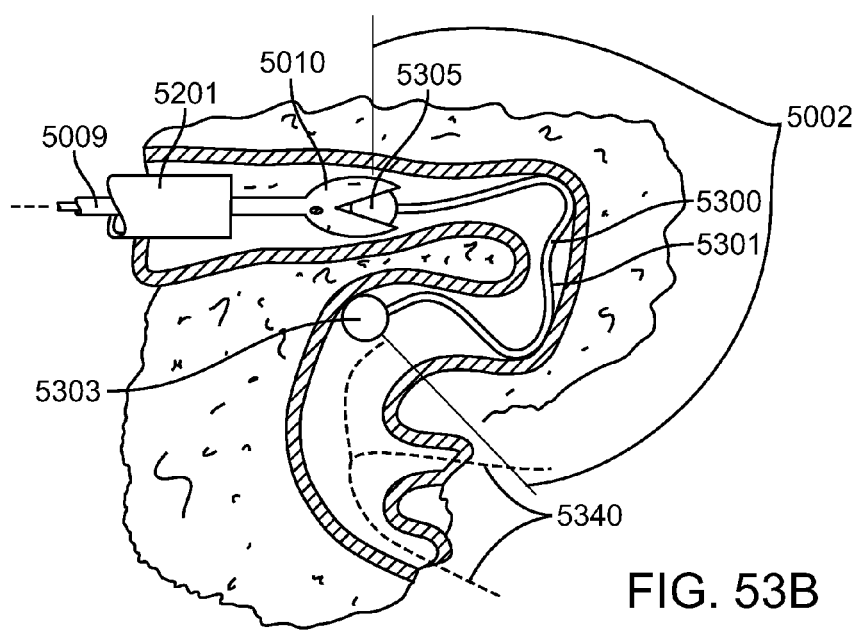

FIGS. 53A and 53B show an implant 5300 for treating airway 5002 of a lung. As described above, airway 5002 comprises a portion of a branching airway system, and the airway targeted for deployment will typically define an airway axis 5340. Implant 5300 comprises an elongate body 5301, a distal end 5303, and a proximal end 5305. Elongate body 5301 is biased to bend to a bent deployed configuration as described above and as shown in FIG. 53B. A pusher grasper device 5009 is coupled to the proximal end 5305 with a grasper coupler 5010 that is locked to implant 5300 using an actuation plunder 5012, handle 5011, and pull wire that runs through the central lumen in the pusher catheter. Prior to deployment, implant 5300 may be loaded into a tubular loading cartridge, for example, cartridge 3801, and advanced from the loading cartridge into the lumen of catheter 5301. Pusher grasper device 5009 can advance implant 5300 through delivery catheter 5201. As shown in FIG. 53A, when restrained within delivery catheter 5201, elongate body 5301 is maintained in a straightened configuration which defines a long axis between the distal end 5303 and proximal end 5305. As shown in FIG. 53B, when pusher grasper device 5009 axially restrains implant 5300 and catheter 5201 is pulled proximally from airway axial region 5002, implant 5300 resiliently returns to a bent deployed configuration to bend the airway 5002. More specifically, the airway axis 5340 goes from a relatively straight configuration to a highly bent configuration, with lateral movement of the elongate body and surrounding airway structure thereby compressing adjacent tissue. Once catheter 5201 has been withdrawn from over elongate body 5301, the deployment can be evaluated. The user may axially restrain the implant 5300 while catheter 5201 is advanced axially so as to recapture the implant if the deployment does not appear satisfactory, or the user may actuate plunger 5012 to release implant 5300. Implant 5300 may be loaded into a tubular loading cartridge, for example, cartridge 3801, and advanced from the loading cartridge into the lumen of catheter 5301.

Figure 54:
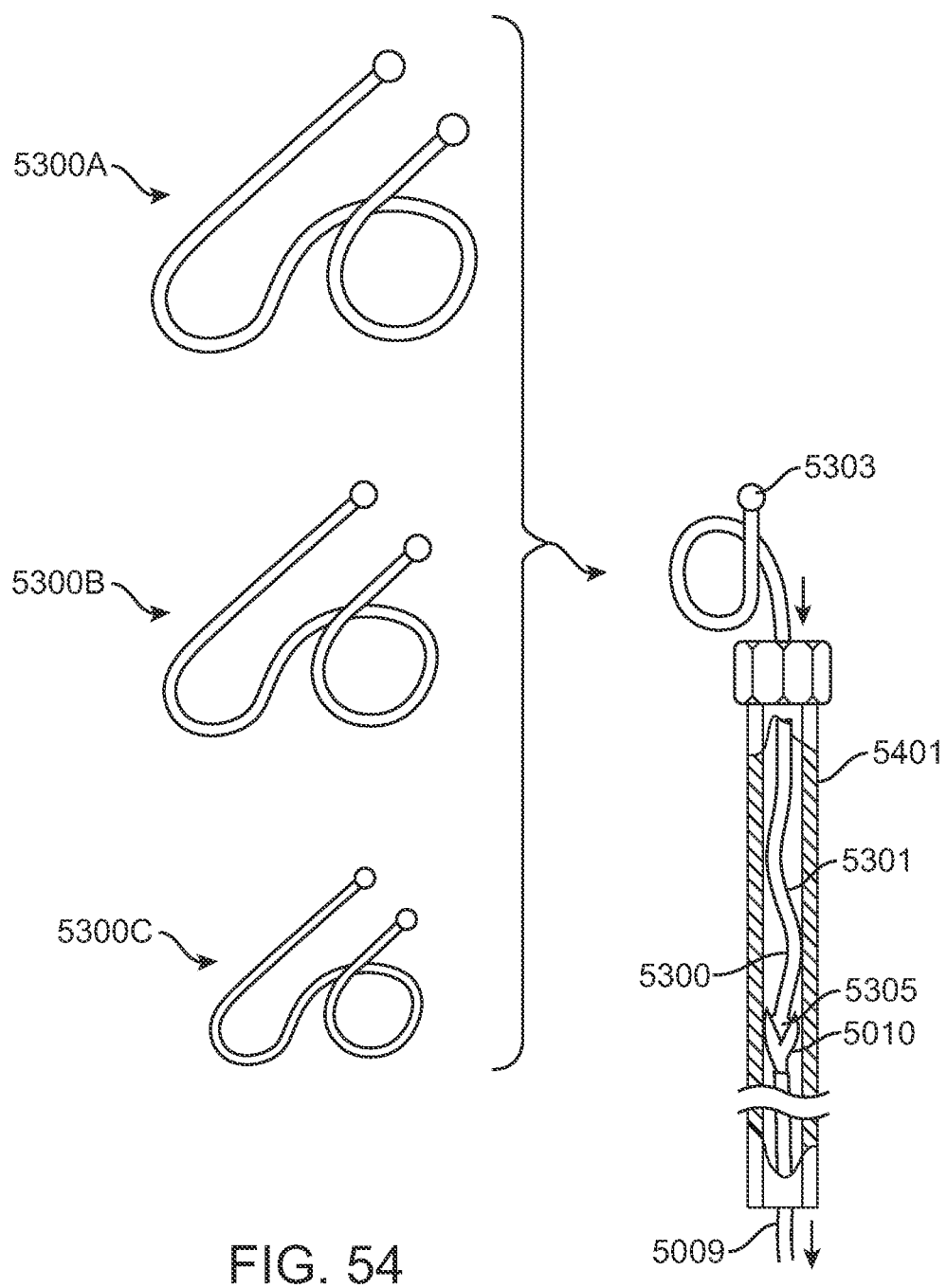
FIG. 54 schematically illustrates selection from among a plurality of alternative devices with different lengths, and loading of a device into a cartridge so that the device can be advanced into a delivery catheter.

FIG. 54 shows a plurality of implants including implant 5300A, 5300B, and 5300C. Each of these implants may have different sizes, lengths, and shapes from each other. When using delivery system 5200, guidewire 5203 may be advanced to a target region near the distal end of the airway system. Guidewire 5203 may be advanced distally until further distal advancement is limited by the distal end of the guidewire being sufficiently engaged by the surrounding lumen of the airway system. Delivery catheter 5201 can then be advanced so that a distal end of catheter 5201 is adjacent a distal end of the guidewire. The distance along the indicia of length 5205 from the bronchoscope to the distal end of guidewire 5203 may be used to select an implant having an elongate body 5301 with a desired length. The desired length may be lesser, greater or about the same as the distance between the distal end of delivery catheter 5201 and distal end of the bronchoscope as indicated by the indicia 5206. The elongate body 5301 having the selected length may be advanced and deployed into the lung via the airway system and using pusher grasper 5009 as described above. To provide a desirable implant shelf life and/or a desirable deployment force for compressing tissues using self-deploying elongate bodies (including those using resilient materials and/or using superelastic materials such as Nitinol™ or the like), it may be advantageous to store the various implants of various sizes in a relaxed state. Once the desired implant geometry or other characteristics have been identified, the selected implant 5300 may be loaded into a loading cartridge 5401 (and subsequently into the lumen of delivery catheter 5201) using pusher grasper device 5009. Pusher grasper device 5009 may be tensioned proximally and/or loading cartridge 5401 may be pushed distally so that elongate body 5301 straightens axially. The loading cartridge 5401 and implant 5300 can then be coupled to the other components of the delivery system, and the implant advanced into the airway as described above.

In exemplary embodiments, the pusher grasper 5009 moves distally while the catheter 5201 is retracted proximally from over the implant during deployment. The selected implant may have a length greater than the measured distance between the distal end of the guidewire (and hence the end of the delivery catheter) and the distal end of the scope. This can help accommodate recoil or movement of the ends of the implant toward each during delivery so as to avoid imposing excessive axial loads between the implant and tissue. Distal movement of the pusher grasper 5009 and proximal end of the implant during deployment also helps keep the proximal end of the implant within the field of view of the bronchoscope, and enhances the volume of tissue compressed by the implant. Exemplary implants may be more than 10% longer than the measured target airway axial region length, typically being from 10% to about 30% longer, and ideally being about 20% longer. Suitable implants may, for example, have total arc lengths of 125, 150, 175, and 200 mm.

Figure 55A:
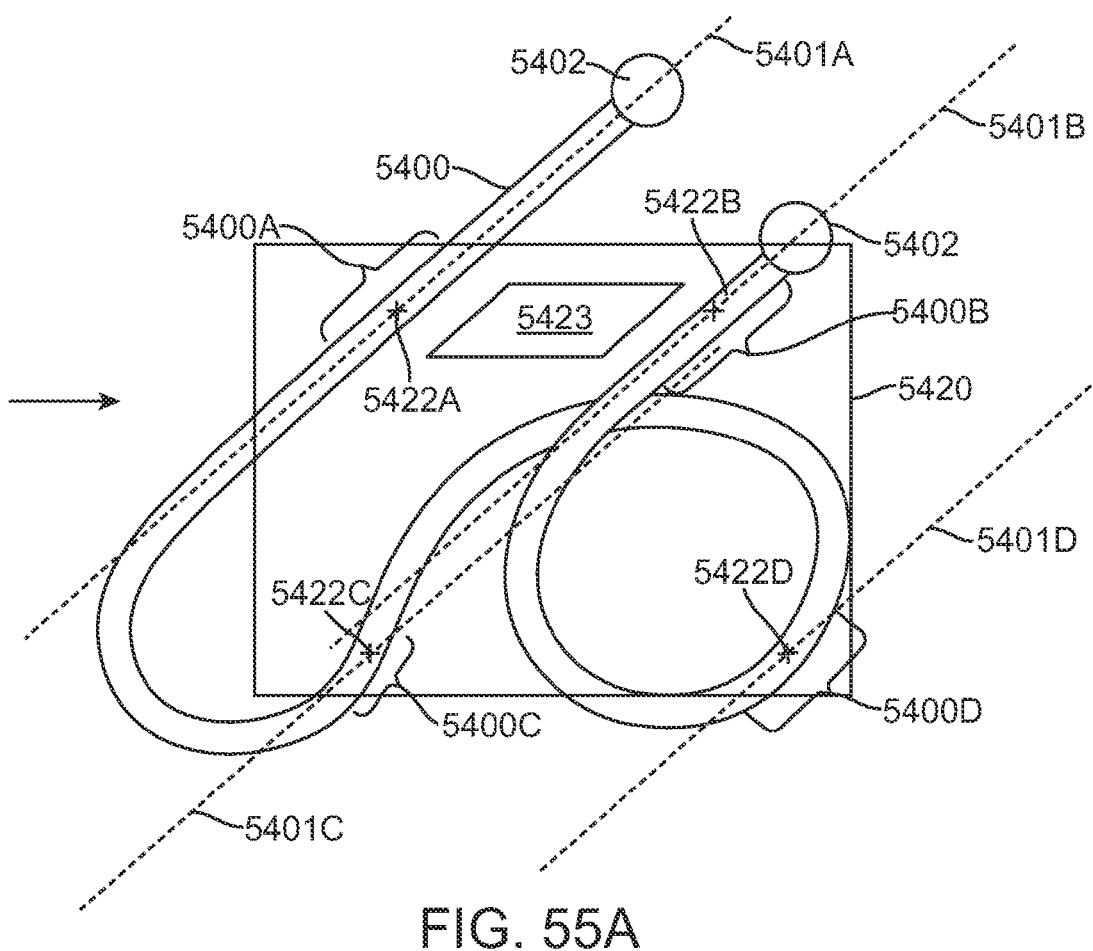
FIGS. 55A-55C illustrate lateral compression of tissue between portions of the deployed device.

FIG. 55A shows an implant 5400 for treating an airway of the lung. Implant 5400 comprises an elongate body having a first or proximal implant portion 5400A and a second or distal implant portion 5400B. Implant 5400 further comprises a third implant portion 5400C and a fourth implant portion 5400D between proximal portion 5400A and distal portion

5400B. First portion 5400A of implant 5400 defines a first local axis 5401A. Second portion 5400B defines a second local axis 5401B. Third portion 5400C defines a third local axis 5401C. Fourth portion 5400D defines a fourth local axis 5401D. Note that the portion of the elongate body advanced along the local axis can optionally be straight but will often be curved. Nonetheless, an elongate portion can be seen to extend along the local axis, presenting an elongate bearing surface to engage and press against the surrounding airway. The ends of implant 5400 are formed into a shape that engages a surrounding luminal surface with an autramatic surface area shown in the form of balls 5402 to minimize perforation through the airway luminal wall. The balls may be made by melting back a portion of implant 5400, however, they may be additional components that are welded, pressed or glued onto the ends of implant 5400.

Figure 55B:
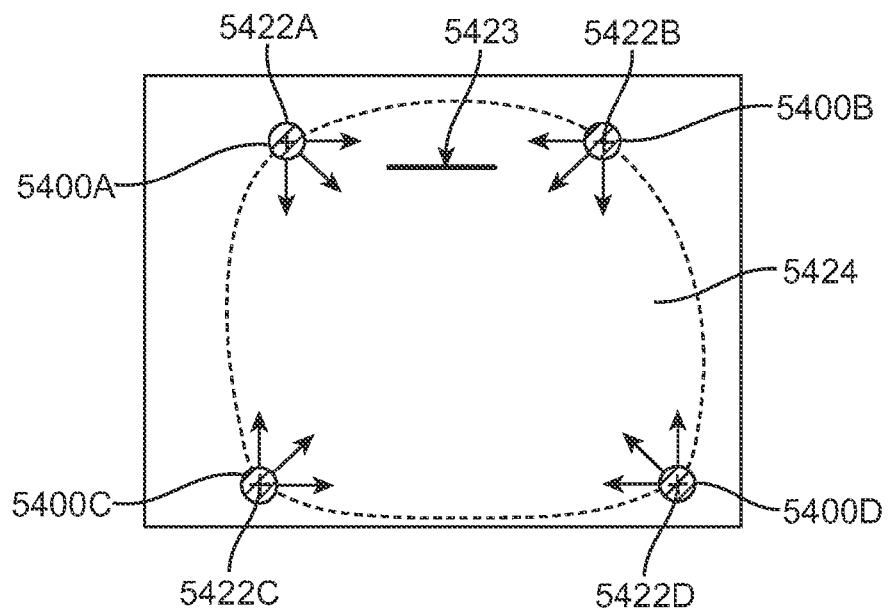

As shown in FIGS. 55A-B, first portion 5400A, second portion 5400B, third portion 5400C, and fourth portion 5400D may traverse a plane 5420, and FIG. 55B illustrates the orientation of compressive forces applied by the local portions of the elongate body in plane 5420. First portion 5400A may intersect plane 5420 at a first point 5422A. Second portion 5400B may intersect plane 5420 at a second point 5422B. Third portion 5400C may intersect plane 5420 at third point 5422C. Fourth portion 5400D may intersect plane 5420 at fourth point 5422D. Intermediate portions 5425 of the elongate body disposed between portions 5400A, 5400B, 5400C, and 5400D may be biased so that when implant 5400 is placed in an airway in a straight configuration, and when implant 5400 bends from the straight configuration to a bent configuration, first portion 5400A, second portion 5400B, third portion 5400C, and/or fourth portion 5400D are urged toward each other. More specifically, and looking at just two of the portions as shown in FIGS. 55A and 55B, first portion 5400A and second portion 5400B will often define a surface therebetween, such as compression plane 5423 (particularly where the portions are relatively flat). The first and second portions compress tissue disposed between them and near compression plane 5423, so that an implant that remains substantially planer can compress a volume of tissue. However, by also compressing tissue using portions of the elongate body that are significantly offset from compression plane 5423 (such as third portion 5400C and forth portion 5400D), a larger volume of lung tissue may be compressed. Compressed area 5424 may be representative of a cross-section of the compressed volume of lung tissue, showing how the use of additional portions of the implant that are not co-planar can enhance compression efficacy. While the above description references a compression plane for simplicity, as can be understood with reference to the illustrations of the three dimensional implants of FIGS. 31D, 39-42, 46, and the like, the implant can be configured with shapes that compress roughly spherical volumes, roughly cylindrical volumes, or other desired shapes.

Figure 55C:
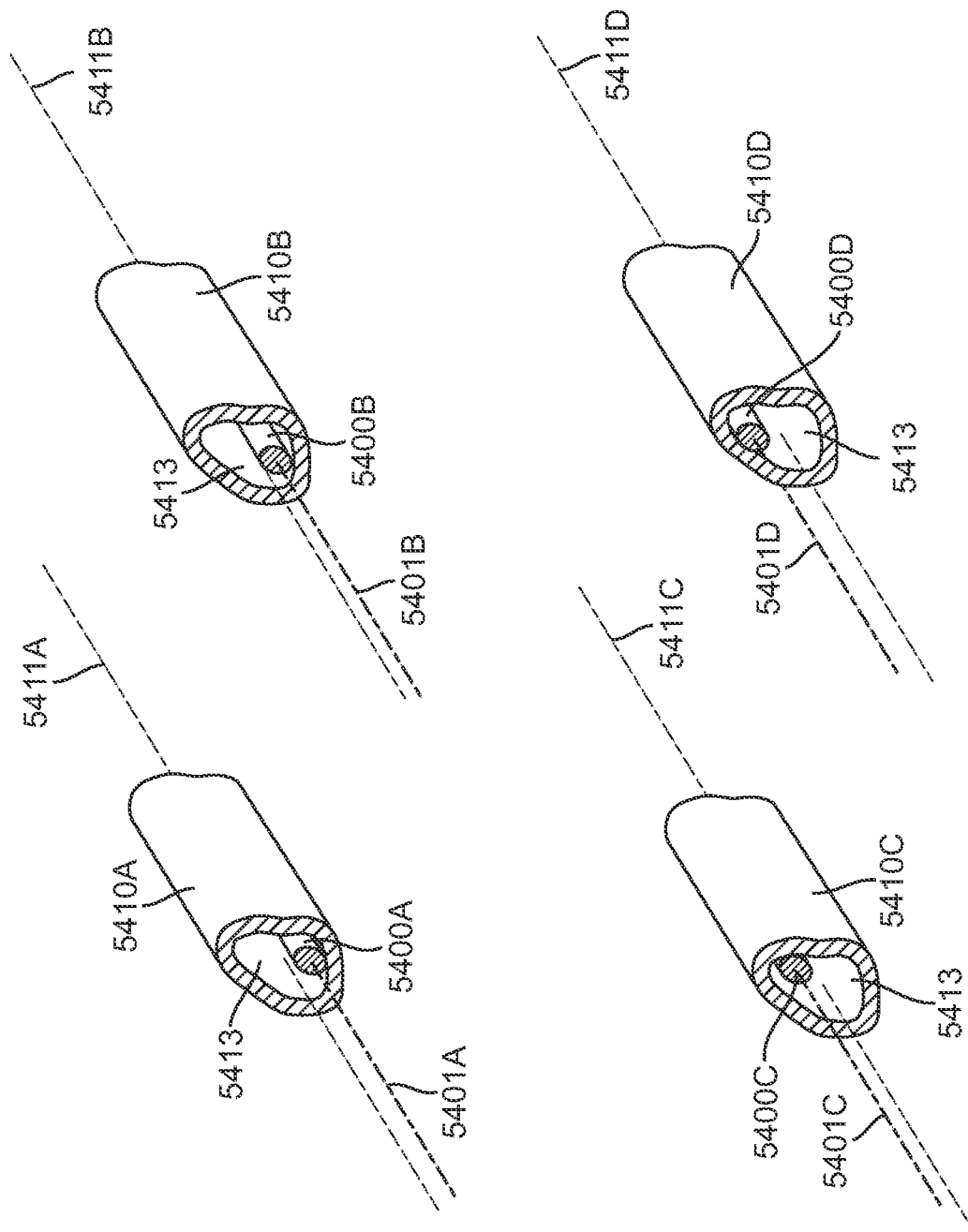

FIG. 55C shows implant 5400 placed into an airway, with only portions of the implant and airway shown for simplicity. The airway comprises a first proximal airway axial region 5410A, a second distal airway axial region 5410B, and a third airway axial region 5410C and a fourth airway axial region 5410D between the first airway axial region 5410A and second airway axial region 5410D. First airway axial region 5410A defines a first local airway axis 5411A. Second airway axial region 5410B defines a second local airway axis 5411B. Third airway axial region 5410C defines a third local airway axis 5411C. Fourth airway axial region 5410D defines a fourth local airway axis 5411D. First airway axial region 5410A, second airway axial region 5410B, third airway axial region 5410C, and fourth airway axial region 5410D each have inner luminal surfaces 5413. First airway axial region 5410A, second airway axial region 5410B, third airway axial region 5410C, and fourth airway axial region 5410D are coupled together axially. First implant portion 5400A of implant 5400 can engage with first airway axial region 5410A. Second implant portion 5400B of implant 5400 can engage with second airway axial region 5410B. Third implant portion 5400C of implant 5400 can engage with third airway axial region 5410C. Fourth implant portion 5400D of implant 5400 can engage with fourth airway axial region 5410D. Implant 5400 can urge first airway axial region 5410A, second airway axial region 5410B, third airway axial region 5410C, and/or fourth airway axial region 5410D laterally toward each other by having respective implant portions urging against inner luminal surfaces 5413, thereby imposing a bend in the airway system and compressing the volume of lung tissue disposed between first airway axial region 5410A, second airway axial region 5410B, third airway axial region 5410C, and/or fourth airway axial region 5410D. The compressed volume of lung tissue may be sufficiently large and may be compressed sufficiently to increase tension in an uncompressed volume of the lung such that lung function of the lung is increased.

Figure 56:
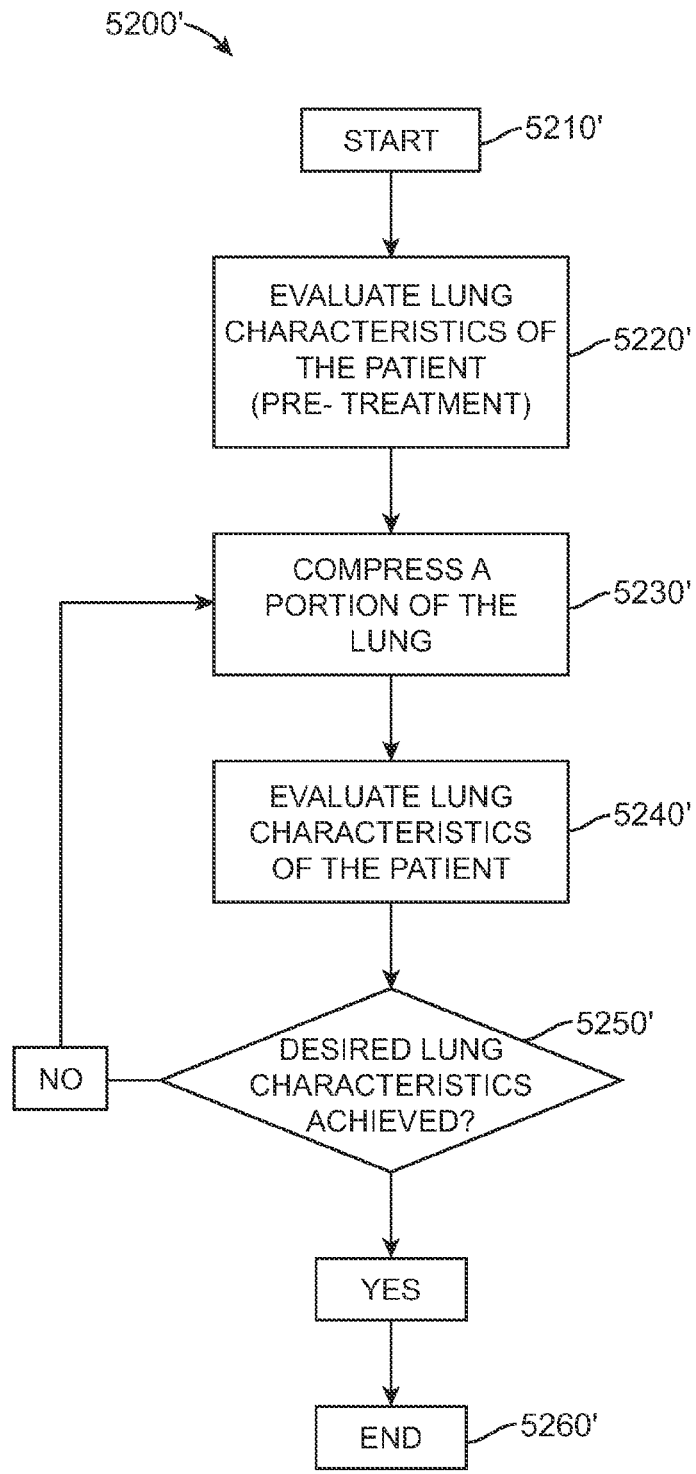
FIG. 56 shows a flow chart illustrating a method for treating a lung of a patient according to embodiments of the invention.

FIG. 56 shows a flow chart illustrating a method 5200' of treating a lung according to embodiments of the invention. A step 5210' starts the treatment procedure. A step 5220' evaluates lung characteristics of the patient prior to treatment. The lung characteristics may be evaluated, for example, by using a ventilator attached to the patient, using one or more imaging modality, using a blood oxygen sensor, using treadmill or other stress tests, or the like. Some of these evaluation devices, and particularly an oxygen sensor, ventilator, and/or imaging system may optionally be used to both evaluate pre-treatment lung function and re-evaluate or monitor one or more lung characteristics during the procedure.

A ventilator can provide useful information regarding lung function, which may comprise patient lung parameters such as pressure, volume, and/or flow. These patient parameters may be compared with each other or tracked over time, e.g., by generating data and/or curves showing pressure versus time, pressure versus volume, volume versus time. The patient parameters may be integrated to identify other related patient parameters, and the measurements may be obtained while the ventilator is operated in a pressure controlled mode, a volume controlled mode, or the like. Advantageously, the ventilator may pressurizing the lung so as to provide signals which indicate airway resistance or obstruction of the lung. Such signals can be highly beneficial for evaluation of patients suffering from chronic obstructive pulmonary disease, particularly before and/or during a lung treatment procedure.

In some embodiments, the thoracic cavity, including the lungs and the diaphragm, can be imaged to evaluate and/or verify the desired lung characteristics, which may also comprise a shape, curvature, position and orientation of the diaphragm, localized density or a density distribution map, and/or the like. The thoracic cavity may be imaged by using fluoroscopy, X-rays, CT scanners, PET scanners, MRI scanner or other imaging devices and modalities. The pre-treatment image data may be processed to provide qualitative or quantitative data for comparison to those from measurements taken during and after the procedure. Additional data may also be obtained, including blood oxygen content and the like.

A portion of the lung, e.g., a diseased portion, is identified and a step 5230' compresses that portion (or any other portion suitable to provide the desired therapeutic effect). Any of the lung volume reduction devices described herein may be used to compress the portion of the lung. Alternative embodiments may combine such devices with other lung treatment structures, or may rely entirely on lung treatment structures other than the embodiments described herein. A step 5240' evaluates the lung characteristics after the portion of the lung has been compressed, for example, to determine the efficacy of the treatment thus far. A step 5250' determines whether or not desired lung characteristics have been achieved.

In some embodiments, the desired lung characteristics have not been achieved if for example, evaluation of the lung characteristics indicate an improvement of less than about 8% from a pre-treatment forced expiratory volume in one second (FEV1) to an FEV1 after compression of the portion of the lung. Preferably, FEV1 improvements will be at least 5% or more before the therapy is terminated, and implants may continue for improvements of less than 10% or even improvements of less than 15%, 20%, 50% or even 75%. In some embodiments, for example, implantation of compression devices may continue when the prior implantation provided an improvement in one or more evaluation parameters (including FEV1 and other evaluation parameters identified herein, other evaluation parameters known for evaluation of COPD patients, and/or other evaluation parameters that are developed) which is significant or above some minimum threshold. Total FEV1 improvements may be between 10 and 30% or more, optionally being between 75% and 150% when the treatment is complete. Note that the FEV1 may be directly measured in some embodiments, but many embodiments will determine whether additional implants should be deployed based on other measurements, with those other measurements being indicative that a desired improvement in FEV1 may have been achieved or has more likely than not been achieved.

Along with (or instead of) evaluations indicative of minimum desired improvements in FEV1, a range of alternative metrics or criteria may be employed in step 5250'. Alternative embodiments of the treatment may continue with additional implant deployments whenever the evaluation of the lung characteristics 5240 indicates an improvement of less than about 6% from a pre-treatment residual volume to a residual volume after compression of the portion of the lung. Other embodiments may continue with improvements in residual lung volume of less than 10% or even less that 15%, 20%, 30%, or even 50% and the completed therapy may provide improvements of 30% or more (optionally being 15-30% or even up to about 95%). In some embodiments, implant deployment may continue when the evaluation of the lung characteristic indicates an improvement of less than about 10% from a pre-treatment six minute walk distance to a six minute walk distance after compression of the first portion of the lung. Alternative walk distance improvement thresholds may be 8% or less, or 12% or less, and the total improvement may be about 15% or more. Once again, the evaluation will often rely on imaging-based data rather than actual walk distance measurements, but those evaluations may still indicate the presence or absence of the desired characteristic.

Still further evaluation criteria may be employed, including continuing to deploy additional implants where the evaluation of the lung characteristic comprises an increase of less than about 1% in oxygen saturation from a pre-treatment measurement of blood oxygen to a measurement of blood oxygen after compression of the first part of the lung. In some embodiments, additional implants may continue so long as the prior implant provided an improvement of at least 0.1% in measured oxygen saturation Total improvements in oxygen saturation when the procedure is completed may be, for example, between 1% and 10% or more, possibly being as high as 45%. In some embodiments, additional implants may continue, for example, when the evaluation of the lung characteristic indicates that airways of the lung outside the first portion remain subject to collapse due to lack of tension in adjacent lung tissue. Achievement of desired lung characteristics may be verified by imaging the thoracic cavity to determine a desired change in the curvature of the diaphragm. For example, when the patient, prior to treatment, has a diaphragm which sags caudally or downward, devices may be implanted until the diaphragm is flattened or curved more upwardly. In some embodiments, implants may continue to be deployed when the interface between the diaphragm and the lung is not yet concave (or sufficiently concave) relative to the lung, so that that the total treatment ideally effects a change from a convex shape (with a lower surface of the lung bulging outwardly away from the center of the lung prior to treatment) to a concave shape (with the lung surface curved inwardly toward the center of the lung). Advantageously, blood oxygen content and diaphragm shape may be determined during the treatment using readily available sensors and imaging systems. If the desired lung characteristics have been achieved, a step 5260; ends the treatment procedure. If the desired lung characteristics have not been achieved, steps 5230', 5240' and 5250' are repeated, for example, for another portion of the lung. Steps 5230', 5240' and 5250' may be initiated or completely repeated within just a few breathing cycles of the patient (such as within 15 breathing cycles) 6 hours of the prior iteration of those steps.

Figure 57:
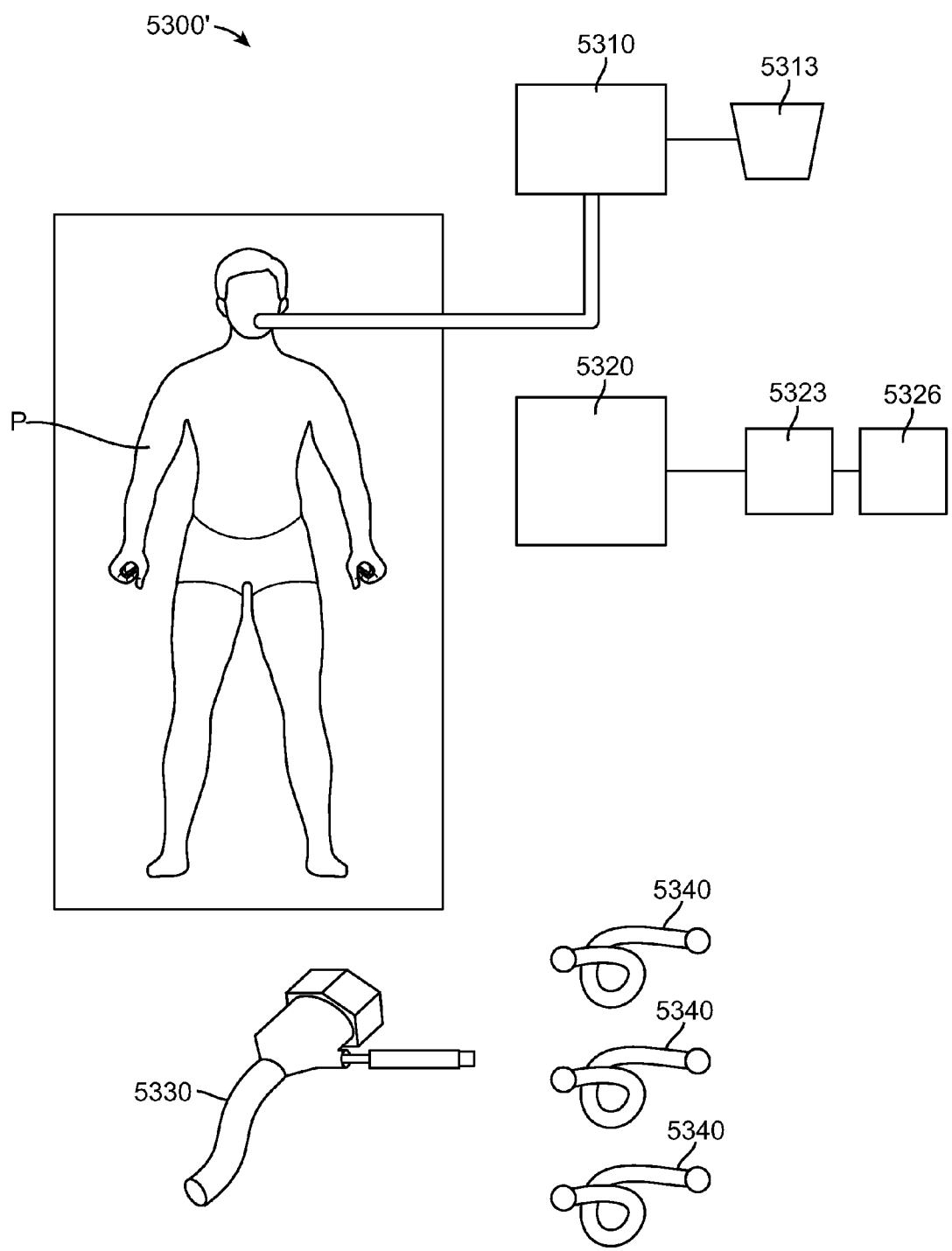
FIG. 57 illustrates a system used to perform the method of FIG. 56.

FIG. 57 shows a system 5300' which can perform the above-described method 5200 to treat a lung of a patient P. System 5300' comprises a ventilator 5310, an imaging device 5320, a delivery system 5330 (ideally including a bronchoscope, delivery catheter, pusher/grasper, and other components described above), and lung volume reduction devices 5340. Patient P may be connected to ventilator 5310, either intermittently or continuously during the treatment. Ventilator 5310 may be coupled to a display 5313 which may show patient parameters such as pressure, volume, and flow and may compare these parameters with each other or versus time, e.g., pressure versus time, pressure versus volume, volume versus time. Imaging device 5320 may be coupled to an image processor 5323 which may be coupled to an imaging display 5326. Image processor 5323 may enhance or post-process the images taken by 5320 of the thoracic cavity of patient P and imaging display 5326 may show these enhanced images. Bronchoscope 5330 may be used to visualize the interior of the airways of the lung and may be used to facilitate insertion of lung volume reduction devices 5340.

Figure 58A:
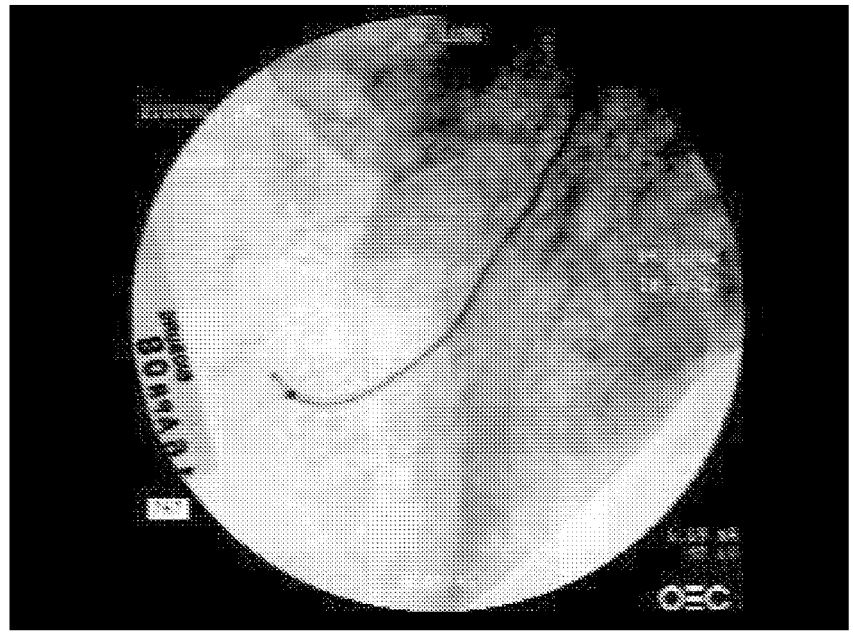
FIGS. 58A and 58B are images of human lung tissue before and after a portion of the lung tissue is compressed from within an airway by an embodiment of an implant.
Figure 58B:
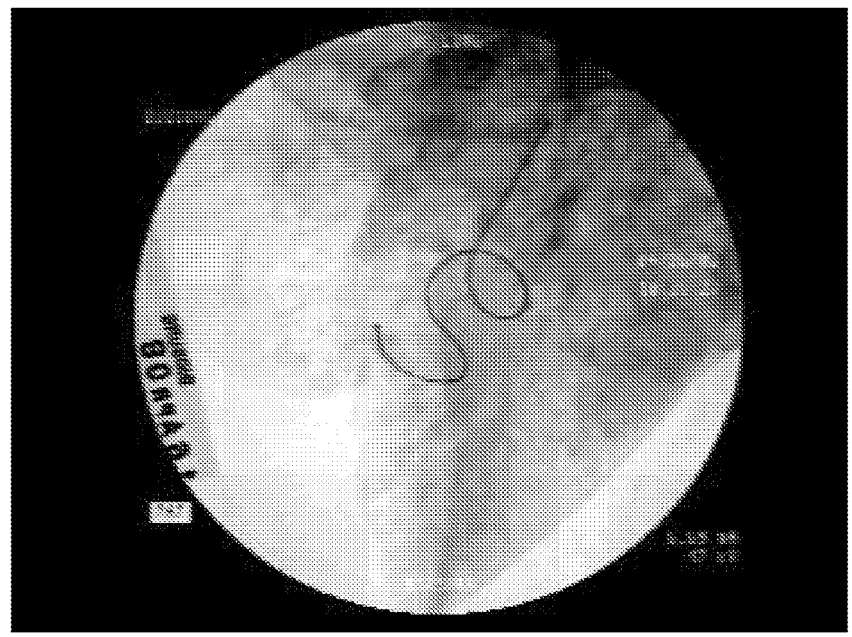

FIGS. 58A and 58B show two photos of a human lung in a chest cavity simulator. The lungs were explanted from a person who expired due to chronic obstructive pulmonary disease (COPD). The cavity is sealed with the lung's main stem bronchi protruding through a hole in the cavity wall. The bronchi has been sealed to the hole so a vacuum can be applied to aspirate the air from the space between the cavity interior and the lung. This allows the lung to be drawn to a larger expanded condition with vacuum levels that are physiologic (such as 0.1 to 0.3 psi, similar to that of the typical human chest cavity). FIG. 58A illustrates a 175 mm long implant that has been delivered to a distal end of a delivery catheter as described above. The catheter is substantially constraining the implant in a straightened delivery configuration.

FIG. 58B shows the implant after the catheter has been retracted from the implant to allow the implant to return toward its relaxed configuration. The implant has recovered to its original shape by means of elastic recoil and possibly a Nitinol metal compositional phase change substantially back to austenite. The delivery grasper has been unlocked to release the implant in the airway. By comparing the lung tissue in FIGS. 58A and 58B, the regions of the lung that are compressed by the implant during the process of shape recovery (changing from a delivered shape to a deployed shape) can be identified. The compressed regions are visualized in the fluoroscopic images by distinct increases in darkness or darker grey shades of the images. Darker regions identify more dense regions and lighter identify less dense regions. The implant can be seen to compress regions as it recovers to cause areas of the lung to become darker. Other regions can be seen to be strained or stretched and this can also be seen as regions that are converted to a lighter region.

The implant can be placed in pathologic regions in the lung that provide limited or no exchange of gas to and from the blood stream because the alveolar walls used to do so have been degraded and destroyed by disease. These are typically the most degraded regions that have lost mechanical strength and elasticity. In an inhaling COPD patient these degraded areas fill with air first, at the expense of gas filling in regions that could better help the patient, because the weakened tissue presents little to no resistance to gas filling. By implanting the devices in these areas, resistance is provided so the gas is filled in regions that still can effectively exchange elements to and from the blood stream. Viable regions have structure remaining so resistance to gas filling is present as this is a normal physiologic property. The implant advantageously provides more gas filling resistance in the destroyed regions than the normal physiologic resistance in the viable regions so gas flows to viable tissue. This eliminates or reduces the counterproductive "preferential filling" phenomenon of the most diseased lung tissue prior to treatment.

In some embodiments, an implant is deployed in a straight configuration with the use of a catheter, e.g., catheter 5201, to contain it in a generally straight shape. Alternative embodiments may use the working lumen of the bronchoscope directly so that the bronchoscope is used as a delivery catheter. Upon removal of the constraining catheter, the implant recoils to a deployed shape that can be easily identified by the fact that the distance from one end to the second is reduced. The proximal end of the implant may be grasped, e.g., with pusher grasper device 5009, and held so that the distal end of the implant remains engaged against the desired airway tissue as the length of the implant is progressively unsheathed (by withdrawing the catheter proximally). High tensile forces might be generated between the distal portion of the implant and the airway tissue if the proximal end of the implant is held at a fixed location throughout deployment, as the implant is biased to recoil or bring the ends together when released. Hence, it can be advantageous to allow the proximal end of the implant to advance distally during release, rather than holding the implant from recoiling, as these forces may be deleterious. For example, the distance and tissue thickness between the distal end of the implant and the lung surface is short, there may be little strain relief on the tissue and the risk of rupture may be excessive. Additionally, the implant might otherwise tend to foreshortened after it is released by the grasper. When foreshortening occurs, the proximal end of the implant may travel distally beyond the viewing field of the bronchoscope and the user can have difficulty retrieving the implant reliably.

Figure 59A:
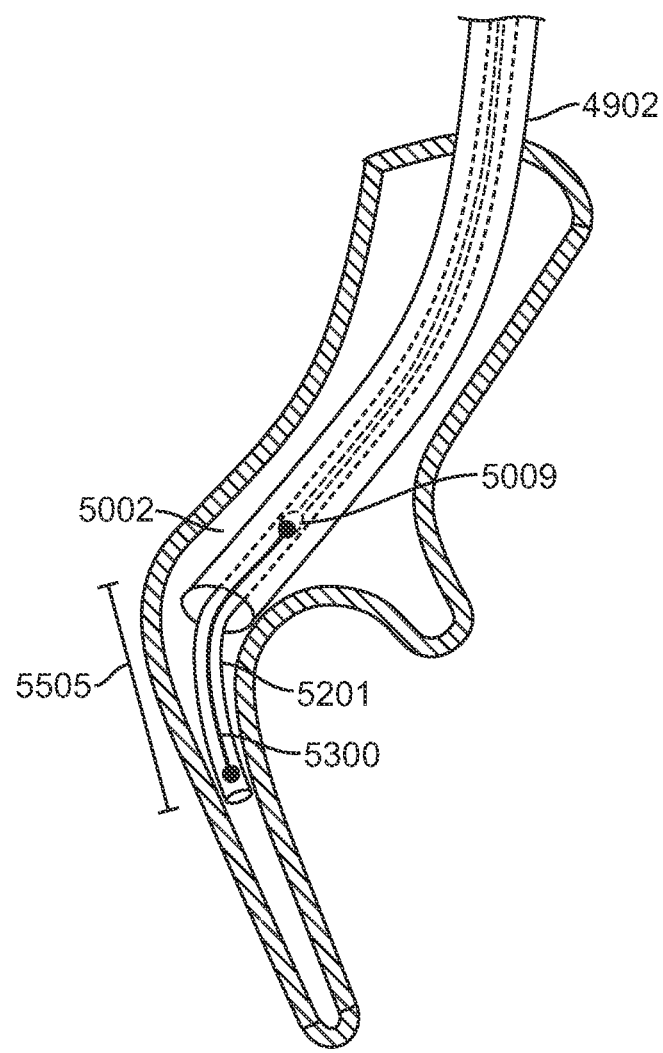
FIGS. 59A-59C illustrate the delivery of a lung volume reduction device according to embodiments of the invention.
Figure 59B:
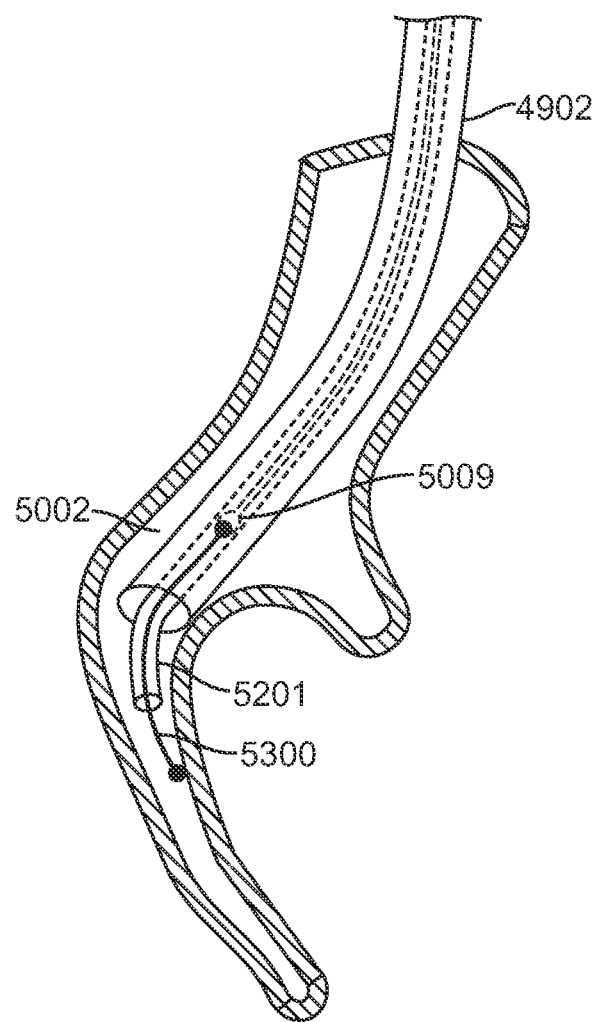
Figure 59C:
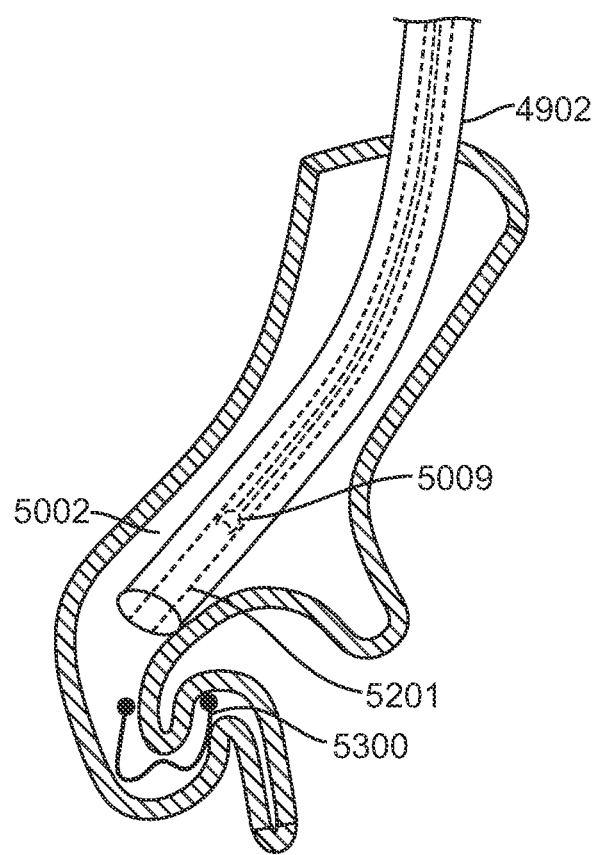

Thus, as schematically shown in FIGS. 59A-59C, an implant 5300 having a length longer than that of the target axial region 5505 may be selected to be deployed in some cases. As described above, a guidewire may be advanced distally from the bronchoscope until the guidewire advancement is inhibited by engagement with the surrounding airway, with the guidewire optionally being relatively large in cross-section (such having a size of between about 5 F and 7 F, ideally having a size of about 5½ F). This allows the guidewire to be advanced to (but not excessively beyond) a target site for the distal end of the implant (which may have an atraumatic ball surface with a diameter from about 1 to about 3 mm, ideally being about 1.5 mm). As shown in FIG. 59A, catheter 5201 is advanced distally from the distal end of bronchoscope 4902 over the guidewire until the distal end of catheter 5201 is aligned with the distal end of the guidewire or till the distal end of the catheter limits further distal advancement due to the distal end of catheter 5201 being similarly sufficiently engaged by the surrounding lumen of the airway system 5002. A length 5505 of the target axial region of the airway is measured. Length 5505 may be the distance between the distal end of the advanced catheter 5201 and the distal end of the bronchoscope 4902, and the guidewire can be withdrawn proximally after the measurement. An implant 5300 having a length greater than the measured length 5505 is selected and distally advanced through catheter 5201 using pusher grasper 5009 as previously described. Implants having a length of at least 10% more, preferably about 20% more, than the measured target axial region may be selected.

FIG. 59B shows the deployment of implant 5300. Implant 5300 is advanced through the lumen of catheter 5201 to adjacent its distal end and the catheter 5201, the distal end of the implant is (at least initially) held axially in place, and the catheter is withdrawn proximally from over a distal portion of the implant. As catheter 5201 is withdrawn, implant 5300 bends laterally and compresses a portion of airway 5002. As shown in FIG. 59B, a larger portion airway 5002 can be compressed by implant 5300 once catheter 5201 is fully withdrawn such that it no longer restrains implant 5300. As the catheter is progressively withdrawn, the proximal end of the implant moves distally relative to the surrounding bronchoscope and airway tissue. The proximal end of implant 5300 may also be released by pusher grasper 5009 after implant 5300 has foreshortened (when measured along the axial center of the airway) gradually throughout its release.

By using a longer implant 5300, the proximal end of implant 5300 can also be fed into the airway while the potential energy of the implant is being freed to apply work on the lung tissue (while the catheter is being pulled off of the implant). The lung airways can be distorted so the airway cross section is pushed to a more oval shape. Longer implants can tend to zigzag back and forth across the airway lumen so that implants that are significantly longer than the measured airway length can be introduced. For example, a 150 mm long (arc length) implant can be deployed into a 100 mm long airway. The greater length of the implant may minimize the uncontrolled recoil that may cause the proximal end to be lost in the patient upon release. Greater implant length can also allow the user to feed the implant into the patient while the catheter is removed without over stressing the lung tissue. Additionally, should foreshortening of the longer implant occur, the proximal end of the implant can still remain within the viewing field of the bronchoscope and the user can thus retain the ability to retrieve the implant reliably. It should be understood that the length of the implant relative to the diameter of the airway may be much greater than the schematic illustration of FIGS. 59A-59C, that the implant may have more complex three dimensional curvature to effect volumetric compression of the lung tissue, and the like.

As will be appreciated by those skilled in the art, the device can be manufactured and deployed such that it is deliverable through a bronchoscope. When actuated, the device can be adapted and configured to bend or curl which then distorts lung tissue with which the device comes in contact. Lung tissues that may be beneficially distorted by the device are airways, blood vessels, faces of tissue that have been dissected for introduction of the device or a combination of any of these. By compressing the lung tissue, the device can result in an increase in elastic recoil and tension in the lung in at least some cases. Additionally, in some instances, lung function can be at least partially restored regardless of the amount of collateral ventilation. Further, the diaphragm may, in some instances, move up once greater tension is created which enables the lung cavity to operate more effectively.

Devices according to the invention have a small cross-section, typically less than 10 F. The flexibility of the device prior to deployment facilitates advancement of the device through the tortuous lung anatomy. Once deployed, the device can remain rigid to hold and maintain a tissue deforming effect. Further, the device design facilitates recapture, de-activation and removal as well as adjustment in place.

Candidate materials for the devices and components described herein would be known by persons skilled in the art and include, for example, suitable biocompatible materials such as metals (e.g. stainless steel, shape memory alloys, such a nickel titanium alloy (nitinol), titanium, and cobalt) and engineering plastics (e.g. polycarbonate). See, for example U.S. Pat. Nos. 5,190,546 to Jervis for Medical Devices Incorporating SIM Memory Alloy Elements and 5,964,770 to Flomenblit for High Strength Medical Devices of Shape Memory Alloy. In some embodiments, other materials may be appropriate for some or all of the components, such as biocompatible polymers, including polyetheretherketone (PEEK), polyarylamide, polyethylene, and polysulphone.

Polymers and metals used to make the implant and delivery system should be coated with materials to prevent the formation and growth of granular tissue, scar tissue and mucus. Many of the drugs used with stent products to arrest hyperplasia of smooth muscle cells in blood vessels after deploying metallic stents will work very well for these devices. Slow release drug eluting polymers or solvents may be used to regulate the release of drugs that include any substance capable of exerting a therapeutic or prophylactic effect for a patient. For example, the drug could be designed to inhibit the activity of smooth muscle cells. It can be directed at inhibiting abnormal or inappropriate migration and/or proliferation of smooth muscle cells to inhibit tissue mass buildup. The drug may include small molecule drugs, peptides or proteins. Examples of drugs include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin$_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co. of Stamford, Conn.), docetaxel (e.g. Taxotere®, from Aventis S. A. of Frankfurt, Germany) methotrexate, azathioprine, vincristine, vinblastine, fluorouracil, doxorubicin hydrochloride (e.g. Adriamycin® from Pharmacia & Upjohn of Peapack N.J.), and mitomycin (e.g. Mutamycin® from Bristol-Myers Squibb). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein Hh/IIIa platelet membrane receptor antagonist antibody, recombinant hirudin, and thrombin inhibitors such as Angiomax™ (Biogen, Inc. of Cambridge, Mass.). Examples of such cytostatic or antiproliferative agents include angiopeptin, angiotensin converting enzyme inhibitors such as captopril (e.g. Capoten® and Capozide® from Bristol-Myers Squibb), cilazapril or Hsinopril (e.g. Prinivil® and Prinzide® from Merck & Co., Inc. of Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which jtnay be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis of New York, N.Y.), 40-O-(3-hydroxy)propyl-rapamycin, 40-O-[2-(2-hydroxy)ethoxy]ethyl-rapamycin, and 40-O-tetrazole-rapamycin.

Other polymers that may be suitable for use in some embodiments, for example other grades of PEEK, such as 30% glass-filled or 30% carbon filled, provided such materials are cleared for use in implantable devices by the FDA, or other regulatory body. The use of glass filled PEEK would be desirable where there was a need to reduce the expansion rate and increase the flexural modulus of PEEK for the instrument Glass-filled PEEK is known to be ideal for improved strength, stiffness, or stability while carbon filled PEEK is known to enhance the compressive strength and stiffness of PEEK and lower its expansion rate. Still other suitable biocompatible thermoplastic or thermoplastic polycondensate materials may be suitable, including materials that have good memory, are flexible, and/or deflectable have very low moisture absorption, and good wear and/or abrasion resistance, can be used without departing from the scope of the invention. These include polyetherketoneketone (PEKK), polyetherketone (PEK), polyetherketoneetherketoneketone (PEKEKK), and polyetheretherketoneketone (PEEKK), and generally a polyaryletheretherketone. Further other polyketones can be used as well as other thermoplastics. Reference to appropriate polymers that can be used in the tools or tool components can be made to the following documents, all of which are incorporated herein by reference. These documents include: PCT Publication WO 02/02158 Al, to Victrex Manufacturing Ltd. entitled Bio-Compatible Polymeric Materials; PCT Publication WO 02/00275 Al, to Victrex Manufacturing Ltd. entitled Bio-Compatible Polymeric Materials; and PCT Publication WO 02/00270 Al, to Victrex Manufacturing Ltd. entitled Bio-Compatible Polymeric Materials. Still other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used as well for portions of the instrument that are desired to be radiolucent.

The implant described herein can be made of a metallic material or an alloy such as, but not limited to, cobalt-chromium alloys (e.g., ELGILOY), stainless steel (316L), "MP3SN," "MP2ON," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention. "MP35N" and "MP2ON" are trade names for alloys of cobalt, nickel, chromium and molybdenum available from Standard Press Steel Co. of Tenkintown, Pa. "MP35N" consists of 35% cobalt, 35% nickel, 20% chromium, and 10% molybdenum. "MP2ON" consists of 50% cobalt, 20% nickel, 20% chromium, and 10% molybdenum.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims presented will define the scope of the invention and that methods and structures within the scope of these claims and their equivalents be covered thereby.

What is claimed is:

1. A method for treating a lung of a patient, the lung including an airway system with a plurality of branching airways, the method comprising:
   coupling a ventilator to the patient prior to treatment of the patient for measuring lung characteristics;
   obtaining a pre-treatment forced expiratory volume in one second (FEV1) lung measurement of the patient;
   while the ventilator is coupled with the patient and measuring lung characteristics of the patient, compressing a first portion of the lung from within a first airway so as to generate an increased tension in a first uncompressed portion of the lung while permitting airflow through the first airway into the compressed first portion of the lung from the first uncompressed portion of the lung;
   evaluating a change in the ventilator measured lung characteristics of the patient with the first portion of the lung compressed, wherein the evaluation comprises measurement of FEV1 with the first portion of the lung compressed; and
   while the ventilator is coupled with the patient and measuring lung characteristics of the patient, compressing a second portion of the lung from within a second airway in response to the evaluation indicating an increase of less than an FEV1 improvement threshold from the pre-treatment FEV1 to the FEV1 after compression of the first portion of the lung, the FEV1 improvement threshold being at least 8% or more, wherein the compressing of the second portion of the lung is performed so as to generate an increased tension in a second uncompressed portion of the lung while permitting airflow through the second airway into the compressed second portion of the lung from the second uncompressed portion of the lung, the second compressed portion of the lung being different from the first compressed portion of the lung.

2. The method of claim 1, wherein the evaluation and the compression of the second portion of the lung both occur within 6 hours of the compressing of the first portion of the lung.

3. The method of claim 2, wherein the compression of the second portion of the lung is completed in the same procedure as the compression of the first portion of the lung so that the patient is not relocated therebetween.

4. The method of claim 2, wherein evaluation is initiated within a few breathing cycles of completion of the compressing of the first portion of the lung, the evaluation indicating enhanced lung function induced at least in part by mechanical compression within the lung and without requiring other tissue response-induced delay for effective determination of efficacy.

5. The method of claim 1, wherein the evaluation further comprises evaluating a change in density of lung tissue by remotely imaging the lung tissue in situ.

6. The method of claim 1, wherein the evaluation further comprises identifying a change in shape of a diaphragm along a lower surface of the lung from an overall convex shape bulging outwardly away from the lung before treatment to a surface which is not yet curving sufficiently inwardly into the lung after compression of the first portion of the lung by remotely imaging the lung tissue in situ.

7. The method of claim 1, wherein the evaluation indicates an improvement of less than 6% from a pre-treatment residual volume to a residual volume after compression of the first portion of the lung.

8. The method of claim 1, wherein the evaluation indicates an improvement of less than 10% from a pre-treatment six minute walk distance to a six minute walk distance after compression of the first portion of the lung.

9. The method of claim 1, wherein the evaluation comprises an increase of less than 1% from a pre-treatment measurement of blood oxygen to a measurement of blood oxygen after compression of the first portion of the lung.

10. The method of claim 1, wherein the evaluation indicates that airways of the lung outside the first portion of the lung remain subject to collapse due to lack of tension in adjacent lung tissue.

11. The method of claim 1, wherein the evaluation comprises imaging of an uncompressed region of distributed disease after compression of the first portion of the lung, the uncompressed region of distributed disease being separated from the first portion of the lung and the compression of the first portion of the lung increasing pre- expiration tension in distributed tissue of the lung that is healthier than the imaged uncompressed region of distributed disease.

12. The method of claim 1, wherein the increased tension in the first uncompressed portion of the lung is generated regardless of collateral flow between the compressed first portion of the lung and the first uncompressed portion of the lung.

13. The method of claim 12, wherein the increased tension in the second uncompressed portion of the lung is generated regardless of collateral flow between the compressed second portion of the lung and the second uncompressed portion of the lung.

14. The method of claim 1, wherein the increased tension in the second uncompressed portion of the lung is generated regardless of collateral flow between the compressed second portion of the lung and the second uncompressed portion of the lung.

15. The method of claim 1, wherein the FEV1 improvement threshold is within a range from 8% to 15%.

16. The method of claim 1, wherein the FEV1 improvement threshold is within a range from 8% to 20%.

17. The method of claim 1, wherein the FEV1 improvement threshold is within a range from 8% to 50%.

18. The method of claim 1, wherein the FEV1 improvement threshold is within a range from 8% to 75%.

* * * * *